(12) United States Patent
Klar et al.

(10) Patent No.: US 9,040,691 B2
(45) Date of Patent: May 26, 2015

(54) HYDROXYMETHYLARYL-SUBSTITUTED PYRROLOTRIAZINES AS ALK1 INHIBITORS

(75) Inventors: Jürgen Klar, Wuppertal (DE); Verena Vöhringer, Wolfegg (DE); Joachim Telser, Wuppertal (DE); Mario Lobell, Wuppertal (DE); Frank Süßmeier, München (DE); Volkhart Min-Jian Li, Velbert (DE); Michael Böttger, Wuppertal (DE); Stefan Golz, Mülheim an der Ruhr (DE); Dieter Lang, Velbert (DE); Karl-Heinz Schlemmer, Wuppertal (DE); Thomas Schlange, Haan (DE); Andreas Schall, Wuppertal (DE); Wenlang Fu, Florham Park, NJ (US)

(73) Assignee: BAYER INTELLECTUAL PROPERTY GMBH, Monheim (DE)

(*) Notice: Subject to any disclaimer, the term of this patent is extended or adjusted under 35 U.S.C. 154(b) by 0 days.

(21) Appl. No.: 14/130,586

(22) PCT Filed: Jun. 26, 2012

(86) PCT No.: PCT/EP2012/062366
§ 371 (c)(1),
(2), (4) Date: May 28, 2014

(87) PCT Pub. No.: WO2013/004551
PCT Pub. Date: Jan. 10, 2013

(65) Prior Publication Data
US 2014/0256718 A1 Sep. 11, 2014

Related U.S. Application Data

(60) Provisional application No. 61/503,840, filed on Jul. 1, 2011.

(30) Foreign Application Priority Data

Mar. 27, 2012 (EP) .................................... 12161547

(51) Int. Cl.
C07D 487/04 (2006.01)
C07D 401/04 (2006.01)
A61K 31/53 (2006.01)
A61K 31/4427 (2006.01)
A61P 25/02 (2006.01)
A61P 27/02 (2006.01)
A61K 31/5377 (2006.01)

(52) U.S. Cl.
CPC .......... *A61K 31/5377* (2013.01); *A61K 31/4427* (2013.01); *C07D 401/04* (2013.01); *C07D 487/04* (2013.01); *A61K 31/53* (2013.01)

(58) Field of Classification Search
CPC ..... C07D 487/04; C07D 401/04; A61K 31/53; A61K 31/4427
USPC .......................................... 544/183; 514/243
See application file for complete search history.

(56) References Cited

PUBLICATIONS

Chang et al. Surv Ophthalmol. Sep. 2012 ; 57(5): 415-429.*

* cited by examiner

*Primary Examiner* — Venkataraman Balasubramanian

(57) ABSTRACT

This invention relates to novel 5-[(hydroxymethyl)aryl]-substituted pyrrolo[2,1-f][1,2,4]triazin-4-amines of formula (I), to processes for the preparation of such compounds, to pharmaceutical compositions containing such compounds, and to the use of such compounds or compositions for treating angiogenesis-related disorders, in particular angiogenesis-related ocular disorders.

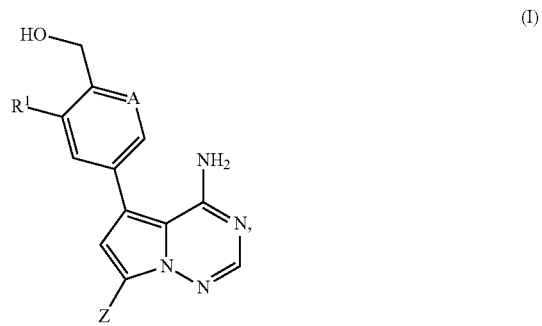

8 Claims, No Drawings

HYDROXYMETHYLARYL-SUBSTITUTED PYRROLOTRIAZINES AS ALK1 INHIBITORS

This invention relates to novel 5-[(hydroxymethyl)aryl]-substituted pyrrolo[2,1-f][1,2,4]triazin-4-amines, to processes for the preparation of such compounds, to pharmaceutical compositions containing such compounds, and to the use of such compounds or compositions for treating angiogenesis-related disorders, in particular angiogenesis-related ocular disorders.

The term angiogenesis, also called neovascularisation, signifies the process of forming new blood vessels. It is involved in normal development as well as in numerous pathological states including, for example, cancer, rheumatoid arthritis, wound healing following injury to a tissue, atherosclerosis, psoriasis, and diseases of the eye.

Various ocular disorders which are responsible for the majority of visual morbidities and blindness in the developed countries are characterized by, caused by and/or result in choroidal, retinal or iris neovascularisation or retinal edema [Campochiaro (2004), *Exp. Opin. Ther.* 4: 1395-1402].

For example, retinopathy associated with diabetes is a leading cause of blindness in type 1 diabetes, and is also common in type 2 diabetes. Another ocular disorder involving neovascularisation is age-related macular degeneration (AMD). AMD is the most common cause of vision loss in the western world in those 50 or older, and its prevalence increases with age. AMD is classified as either wet (neovascular) or dry (non-neovascular). The wet form of the disease is responsible for the most severe loss of vision.

Several other less common, but nonetheless debilitating retinopathies include choroidal neovascular membrane (CNVM), cystoid macular edema (CME, also referred to as macular edema or macular swelling), epi-retinal membrane (ERM, macular pucker), and macular hole. In CNVM, abnormal blood vessels stemming from the choroid grow up through the retinal layers. The fragile new vessels break easily, causing blood and fluid to pool within the layers of the retina. In CME, which can occur as a result of disease, injury or surgery, fluid collects within the layers of the macula, causing blurred, distorted central vision. ERM (macular pucker) is a cellophane-like membrane that forms over the macula, affecting the central vision by causing blur and distortion.

Also related are disorders like hypertrophic and atrophic changes of the retinal pigment epithelium (RPE), retinal detachment, choroidal vein occlusion, retinal vein occlusion, corneal angiogenesis following, for example, keratitis, cornea transplantation or keratoplasty, corneal angiogenesis due to hypoxia (e.g., as a result of extensive contact lens wearing), pterygium conjunctivae, subretinal edema, and intraretinal edema.

Vascular endothelial growth factor (VEGF) has been found to be an important modulator of angiogenesis and has been implicated in the pathology of a number of conditions including AMD and diabetic retinopathy. Furthermore, for AMD it was shown that intravitreal injection of an anti-VEGF inhibitor like pegaptanib, ranibizumab or aflibercept reduces choroidal angiogenesis and vascular leakage [Gragoudas (2004), *N. Engl. J. Med.* 351: 2805-2816; Rosenfeld (2006), *N. Engl. J. Med.* 355: 1419-1431; Dixon (2009), *Expert Opin. Investig. Drugs* 18: 1573-1580].

The current standard of care for AMD is lucentis (ranibizumab), an anti-VEGF therapy. However, only ⅓ of all AMD patients treated with lucentis show improvement in vision [Rosenfeld (2006), *N Engl. J. Med.* 355: 1419-1431]. Therefore new anti-angiogenic therapeutic options with a VEGF-independent mode of action have the potential to improve the current standard of care in ocular diseases like diabetic retinopathy and AMD.

ALK1 (activin receptor-like kinase-1) is a Ser/Thr kinase receptor of the TGFβ receptor family preferentially expressed in endothelial cells and involved in angiogenesis. Members of this family mediate their biological activity by ligand binding to a heterotetrameric receptor complex of type I and type II serine/threonine kinase receptors TβRI and TβRII and accessory type III receptors. TGFβ as well as the high-affinity ligands BMP9 and BMP10 can activate ALK1 in receptor complexes with BMPRII or ActRII and type III receptor endoglin [Scharpfenecker (2007), *J. Cell Sci.* 120: 964-972]. Binding of BMP9 to ALK1 in microvascular endothelial cells activates the Smad1/5/8 pathway [David (2007), *Blood* 109 (5): 1953-1961]. It was postulated that BMP9 inhibits endothelial cell migration and growth. Most studies, however, find that ALK1 receptor activation promotes endothelial cell migration, proliferation, and tube formation [Goumans (2002), *EMBO Journal* 21 (7): 1743-1753; Wu (2006), *Microvasc. Res.* 71: 12-19].

BMP9 and BMP10 activate ALK1 receptor complexes. In endothelial cells, TGFβ can also activate ALK1 while in most cell types TGFβ signals through ALK5. ALK5 activation leads to phosphorylation of Smad2/3 while ALK1 activation results in phosphorylation of Smad1/5. Each Smad signalling pathway finally results in regulation of specific sets of target genes: Smad2/3 signalling induces expression of PAI-1 and repression of Id-1, while Smad1/5 signalling induces Smad6, Smad7 and Id-1 expression and reduces PAI-1 expression [Deng (2006), *J. Cell Biol.* 134: 1563-1571; Ota (2002), *J. Cell Physiol.* 193: 299-318].

Type III receptor endoglin plays a role in fine-tuning of ALK1 and ALK5 pathways especially in endothelial cells, regulating ligand receptor interactions [ten Dijke (2008), *Angiogenesis* 11: 79-89]. Endoglin facilitates TGFβ/ALK1-interaction but reduces TGFβ/ALK5-interaction [David (2007), *Blood* 109: 1953-1961].

Mutations in endoglin and in ALK1 are linked to the autosomal dominant disorder called hereditary hemorrhagic telangiectasia (HHT1 and HHT2, respectively) with characteristics of angiogenic disturbances like arterial venous malformations and telangiectases [Fernandez-Lopez (2006), *Clin. Med. & Res.* 4: 66-78]. RIP1-Tag2 mice with only one functional copy of the ALK1 gene (ALK1$^{+/-}$) show retarded tumor progression and lower microvessel density compared to ALK1$^{wt}$ mice. Similar observations were made with the soluble ALK1-Fc receptor construct RAP-041, that inhibited tumor angiogenesis in vivo and limited tumor growth [Cunha (2010), *J. Exp. Med.* 207: 85-100].

The discovery of potent and selective ALK1 inhibitors is therefore highly desirable to further elucidate the role of ALK1 in blood vessel physiology and pathology, and to derive potential therapeutic options for diseases associated with angiogenesis and vascular remodelling.

In WO 2007/147647-A1, certain 3 pyrazolo[1,5-a]pyrimidine derivatives were described to be the first small molecule ALK1 kinase inhibitors published until then. These compounds were said to be useful for the treatment of diseases of dysregulated vascular growth, in particular of solid tumors and metastases thereof and also of angiogenesis-dependent diseases of the eye such as age-related macular degeneration.

Various pyrrolo[2,1-f][1,2,4]triazin-4-amine derivatives with distinctive inhibition profiles against a range of protein kinases have been disclosed in, inter alia, WO 00/71129-A1, WO 2005/121147-A1, WO 2007/056170-A2, WO 2007/061882-A2, WO 2007/064883-A2, WO 2007/064931-A2, WO 2007/079164-A2, WO 2008/089105-A2, WO 2009/136966-A1, and WO 2010/126960-A1. Generally, these compounds were stated to be useful for the treatment of proliferative and/or angiogenesis-related disorders such as cancer. None of these publications, however, refer to ALK1 as a potential target kinase.

Surprisingly, it has now been found that pyrrolo[2,1-f][1,2,4]triazin-4-amine derivatives having a hydroxymethylaryl substituent in 5-position exhibit potent and selective inhibition of ALK1 kinase which renders these compounds particularly useful for the treatment of angiogenesis-related ocular disorders.

Thus, in one aspect, the present invention relates to 5-[(hydroxymethyl)aryl]-substituted pyrrolo[2,1-f][1,2,4]triazin-4-amines of the general formula (I)

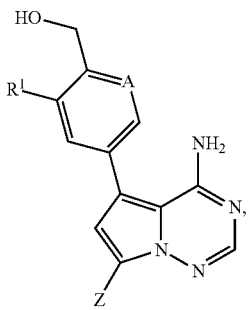

wherein

A is N or C—$R^2$, wherein $R^2$ represents hydrogen, fluoro or chloro, $R^1$ represents hydrogen, fluoro, chloro, methyl, ethyl or methoxy, and Z represents $(C_1-C_4)$-alkyl or $(C_3-C_6)$-cycloalkyl each of which may be substituted with hydroxy, or Z represents a heterocyclic group of the formula

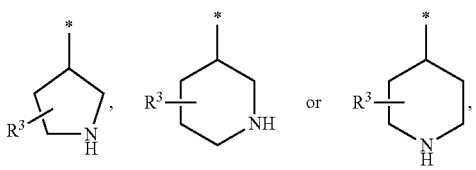

wherein * indicates the point of attachment to the pyrrolotriazine moiety, and $R^3$ represents hydrogen or hydroxy, with the proviso that when $R^3$ is hydroxy, this hydroxy is not attached to a ring carbon atom located adjacent to the ring nitrogen atom, or Z represents a thiazole group of the formula

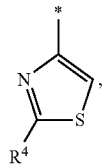

wherein * indicates the point of attachment to the pyrrolotriazine moiety, and $R^4$ represents hydrogen, methyl, ethyl, amino or aminomethyl, or Z represents a group of the formula

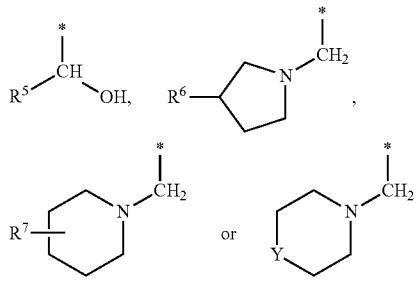

wherein * indicates the point of attachment to the pyrrolotriazine moiety, $R^5$ represents $(C_3-C_6)$-cycloalkyl, oxetanyl, tetrahydrofuranyl or tetrahydropyranyl, $R^6$ represents hydrogen or hydroxy, $R^7$ represents hydrogen or hydroxy, with the proviso that when $R^7$ is hydroxy, this hydroxy is not attached to a ring carbon atom located adjacent to the ring nitrogen atom, and Y is O, NH or $NCH_3$.

The compounds according to this invention can also be present in the form of their salts, solvates and/or solvates of the salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19). Salts which are not themselves suitable for pharmaceutical uses but can be used, for example, for isolation or purification of the compounds according to the invention are also included.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, acetic acid, propionic acid, lactic acid, tartaric acid, malic acid, citric acid, fumaric acid, maleic acid and benzoic acid.

Solvates in the context of the invention are designated as those forms of the compounds according to the invention which form a complex in the solid or liquid state by stoichiometric coordination with solvent molecules. Hydrates are a specific form of solvates, in which the coordination takes place with water. Hydrates are preferred solvates in the context of the present invention.

The compounds of this invention may, either by nature of asymmetric centers or by restricted rotation, be present in the four of isomers (enantiomers, diastereomers). Any isomer may be present in which the asymmetric center is in the (R)-, (S)-, or (R,S)-configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z-) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

Unless otherwise stated, the following definitions apply for the substituents and residues used throughout this specification and claims:

($C_1$-$C_4$)-alkyl represents a straight-chain or branched saturated hydrocarbon radical having 1 to 4 carbon atoms. Examples include methyl, ethyl, n-propyl, isopropyl, n-butyl, isobutyl, sec-butyl, tert-butyl.

($C_3$-$C_6$)-cycloalkyl represents a monocyclic saturated hydrocarbon radical having 3 to 6 ring carbon atoms. Examples include cyclopropyl, cyclobutyl, cyclopentyl, cyclohexyl.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

In a preferred embodiment, the present invention relates to compounds of general formula (I), wherein
A is C—$R^2$, wherein
  $R^2$ represents hydrogen or fluoro,
$R^1$ represents hydrogen, fluoro, chloro, methyl, ethyl or methoxy,
and
Z represents n-propyl, n-butyl or cyclohexyl each of which may be substituted with hydroxy,
or
Z represents a heterocyclic group of the formula

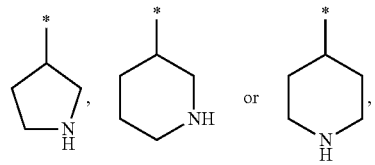

wherein * indicates the point of attachment to the pyrrolotriazine moiety,
or
Z represents a thiazole group of the formula

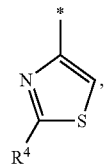

wherein * indicates the point of attachment to the pyrrolotriazine moiety,
and
$R^4$ represents methyl, ethyl, amino or aminomethyl,
or
Z represents a group of the formula

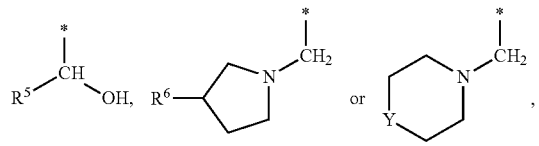

wherein * indicates the point of attachment to the pyrrolotriazine moiety,
$R^5$ represents cyclopropyl or tetrahydropyran-4-yl,
$R^6$ represents hydroxy,
and
Y is O.

In a particularly preferred embodiment, the present invention relates to compounds of general formula (I), wherein
A is C—$R^2$, wherein
  $R^2$ represents hydrogen or fluoro,
$R^1$ represents hydrogen, fluoro, methyl, ethyl or methoxy,
and
Z represents 4-hydroxybutyl or 4-hydroxycyclohexyl,
or
Z represents a heterocyclic group of the formula

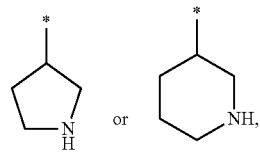

wherein * indicates the point of attachment to the pyrrolotriazine moiety, or

Z represents a thiazole group of the formula

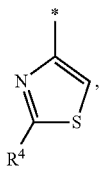

wherein * indicates the point of attachment to the pyrrolotriazine moiety, and $R^4$ represents methyl, ethyl, amino or aminomethyl, or Z represents a group of the formula

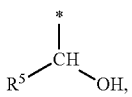

wherein * indicates the point of attachment to the pyrrolotriazine moiety, and $R^5$ represents cyclopropyl.

In a distinct embodiment, the present invention relates to compounds of general formula (I), wherein A is C—$R^2$, wherein $R^2$ represents hydrogen or fluoro.

In a further distinct embodiment, the present invention relates to compounds of general formula (I), wherein A is C—$R^2$, wherein $R^2$ represents fluoro, and $R^1$ represents fluoro.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

In another embodiment, the present invention relates to a process for preparing the compounds of general formula (I), characterized in that a bromopyrrolotriazine of formula (II)

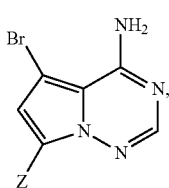

wherein Z has the meaning described above, is either

[A] coupled with an arylboronic acid or ester of formula (III)

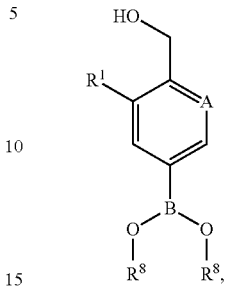

wherein A and $R^1$ have the meanings described above, and $R^8$ represents hydrogen or ($C_1$-$C_4$)-alkyl, or both $R^8$ residues are linked together to form a —$(CH_2)_2$—, —$C(CH_3)_2$—$C(CH_3)_2$—, —$(CH_2)_3$— or —$CH_2$—$C(CH_3)_2$—$CH_2$— bridge, in the presence of a suitable palladium catalyst and a base to yield the target compound of formula (I)

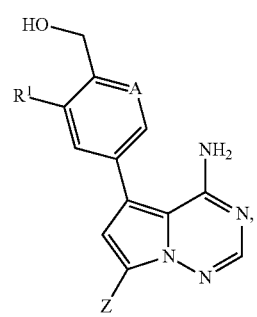

wherein A, Z and $R^1$ have the meanings described above, or

[B] first converted into the corresponding boronic acid or ester derivative of formula (IV)

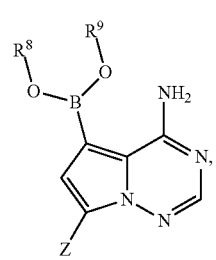

wherein Z has the meaning described above, and $R^9$ represents hydrogen or ($C_1$-$C_4$)-alkyl, or both $R^9$ residues are linked together to form a —$(CH_2)_2$—, —$C(CH_3)_2$—$C(CH_3)_2$—, —$(CH_2)_3$— or —$CH_2$—$C(CH_3)_2$—$CH_2$— bridge, which is then coupled with an aryl bromide of formula (V)

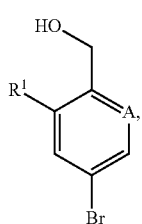

(V)

wherein A and R¹ have the meanings described above,
in the presence of a suitable palladium catalyst and a base to also give the target compound of formula (I)

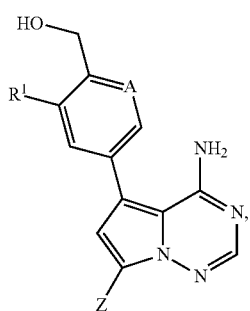

(I)

wherein A, Z and R¹ have the meanings described above,
optionally followed, where appropriate, by (i) separating the compounds of formula (I) into their respective enantiomers and/or diastereomers, preferably using chromatographic methods, and/or (ii) converting the compounds of formula (I) into their respective hydrates, solvates, salts and/or hydrates or solvates of the salts by treatment with the corresponding solvents and/or acids.

As outlined above, compounds of formula (I) can be synthesized by a coupling reaction ("Suzuki coupling") between the bromopyrrolotriazine (II) and an aryl boronate or boronic acid (III). This coupling is generally carried out at elevated temperature using a palladium catalyst, a base and an inert solvent. An overview of catalysts and reaction conditions can be found in the literature [see, for instance, S. Kotha et al., *Tetrahedron* 2002, 58, 9633-9695; T. E. Barder et al., *J. Am. Chem. Soc.* 2005, 127, 4685-4696]. The preferred catalyst in this reaction is tetrakis(triphenylphosphine)palladium(0). The preferred base is sodium carbonate employed as an aqueous solution. The reaction is carried out in organic solvents that are inert under the reaction conditions, such as 1,4-dioxane, acetonitrile, N,N-dimethylformamide (DMF) or dimethylsulfoxide (DMSO), or in water or in mixtures of these solvents. Preferably, the reaction is carried out in a mixture of 1,4-dioxane and water or acetonitrile and water. The reaction is generally performed at temperatures between +100° C. and +250° C., preferably at +120° C. to +150° C. Heating is preferably effected by a single-mode microwave device. The reactions are usually run under an inert gas atmosphere, preferably under argon.

An inverse reactivity of the reaction partners for the Suzuki coupling may sometimes be favorable. For this purpose, the bromopyrrolotriazine (II) is first converted into the corresponding boronate (IV) and then cross-coupled with an aryl bromide (V) according to one of the methods described above. The conversion of (II) to (IV) is achieved by a metal-mediated borylation reaction. The preferred method is the palladium-catalyzed "Miyaura borylation" [see, for instance, J. Takagi et al., *J. Am. Chem. Soc.* 2002, 124, 8001-8006; T. Ishiyama et al., *J. Org. Chem.* 1995, 60, 7508-7510; A. L. S. Thompson et al., *Synthesis* 2005, 547-550]. Procedures, reagents and solvents for the cross-coupling reaction (IV)+(V)→(I) are chosen from those mentioned in the previous section.

Arylboronic acids (III) [R⁸=H] and aryl boronates (III) [R⁸=alkyl, or both R⁸ are linked together to form a cyclic boronic ester, e.g., a pinacolato ester] are either commercially available, or they can be conveniently prepared from the corresponding aryl halides or aryl triflates using a metal-mediated borylation reaction (for references, see previous section). Borylation and subsequent Suzuki coupling may be carried out in two separate steps including isolation and purification of intermediate (III). Alternatively, borylation and cross-coupling may be carried out as a one-pot procedure using (III) directly without isolation and purification.

In cases where a primary or secondary amine moiety forms part of the Z group in the target compounds of formula (I), it may often be beneficial in the borylation and coupling reactions described above to use a protected derivative of this amine as the starting pyrrolotriazine (II) instead of the free amine compound. For this purpose, conventional temporary amino-protecting groups, such as acyl groups (e.g., acetyl or trifluoroacetyl) or carbamate-type protecting groups (e.g., a Boc-, Cbz- or Fmoc-group), may be employed. Preferably, a trifluoroacetyl or a Boc group is used. Similarly, the hydroxy function in the coupling components (III) and (V), respectively, may temporarily be blocked during the process, preferably as a silyl ether derivative such as a trimethylsilyl or tert-butyldimethylsilyl ether.

These protecting groups may then be cleaved off concomitantly during the aqueous work-up of the coupling reaction mixtures, or they are removed in a subsequent, separate reaction step using standard methods known in the art. The preparation of the protected intermediates described above from the corresponding free amines or alcohols of formula (II), (III) and (V), respectively, or from other precursor compounds (see section below) is also readily accomplished following general procedures described in the literature [see, for example, T. W. Greene and P. Wuts, *Protective Groups in Organic Synthesis*, Wiley, New York, 1999].

The preparation of the compounds of the invention may be illustrated by means of the following synthesis scheme:

Scheme 1

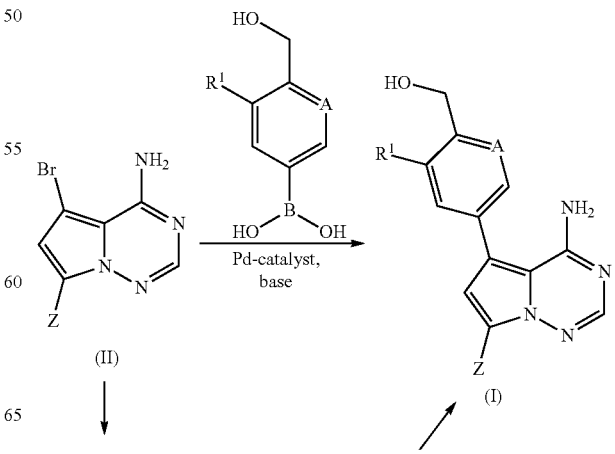

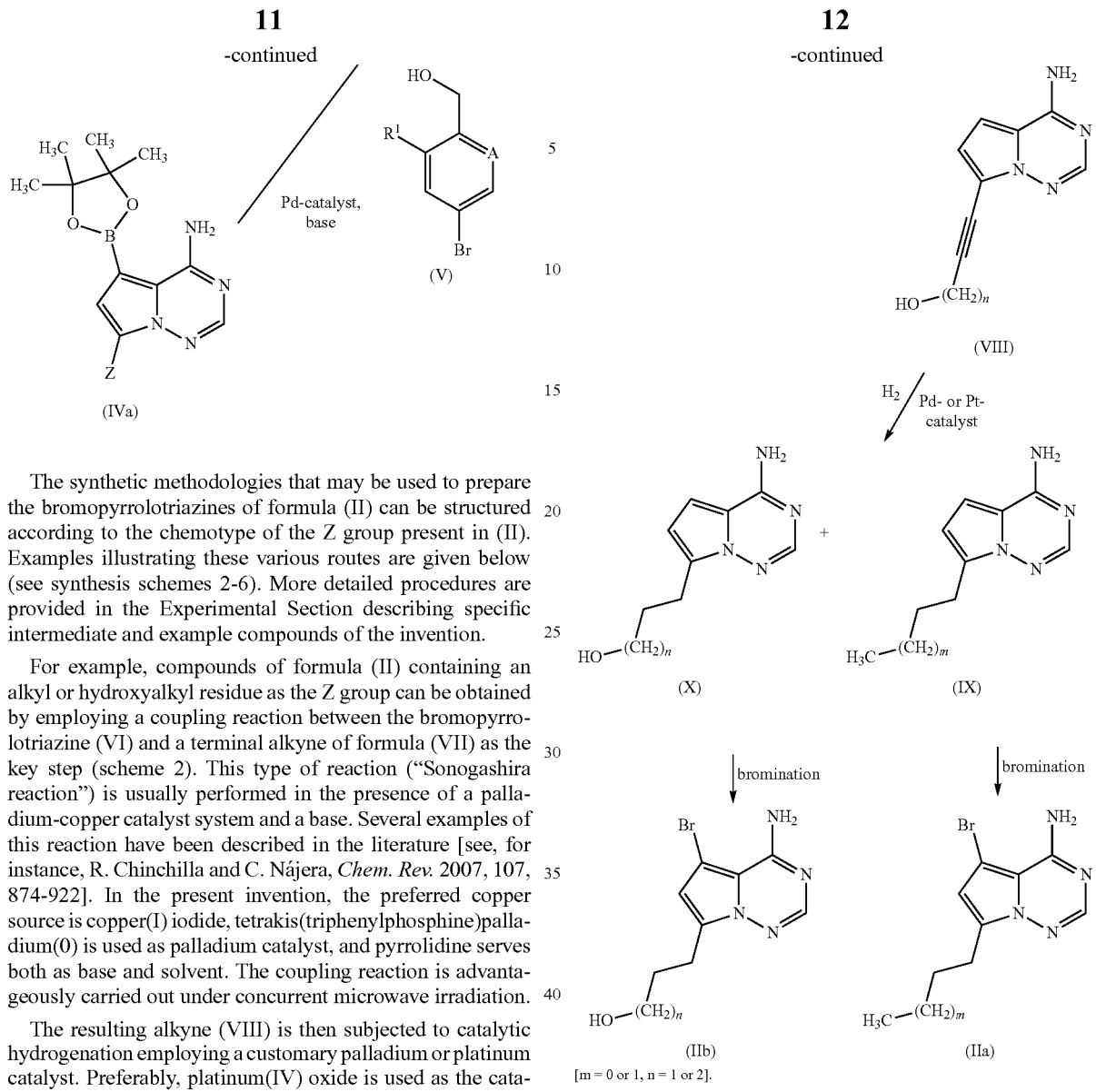

The synthetic methodologies that may be used to prepare the bromopyrrolotriazines of formula (II) can be structured according to the chemotype of the Z group present in (II). Examples illustrating these various routes are given below (see synthesis schemes 2-6). More detailed procedures are provided in the Experimental Section describing specific intermediate and example compounds of the invention.

For example, compounds of formula (II) containing an alkyl or hydroxyalkyl residue as the Z group can be obtained by employing a coupling reaction between the bromopyrrolotriazine (VI) and a terminal alkyne of formula (VII) as the key step (scheme 2). This type of reaction ("Sonogashira reaction") is usually performed in the presence of a palladium-copper catalyst system and a base. Several examples of this reaction have been described in the literature [see, for instance, R. Chinchilla and C. Nájera, Chem. Rev. 2007, 107, 874-922]. In the present invention, the preferred copper source is copper(I) iodide, tetrakis(triphenylphosphine)palladium(0) is used as palladium catalyst, and pyrrolidine serves both as base and solvent. The coupling reaction is advantageously carried out under concurrent microwave irradiation.

The resulting alkyne (VIII) is then subjected to catalytic hydrogenation employing a customary palladium or platinum catalyst. Preferably, platinum(IV) oxide is used as the catalyst, and the reaction is run in acetic acid as the solvent. In some cases, a mixture of products (IX) and (X) is obtained by this procedure which, in any event, can be separated easily by chromatographic methods. A subsequent bromination reaction, preferably using 1,3-dibromo-5,5-dimethylhydantoin as the bromine source, in an inert solvent such as THF or DMF yields the target pyrrolotriazines (IIa) and (IIb), respectively.

The preparation of the starting compound 7-bromopyrrolo[2,1-f][1,2,4]triazin-4-amine (VI) has been described previously [see WO 2007/056170-A2 (Intermediate B)].

Scheme 2

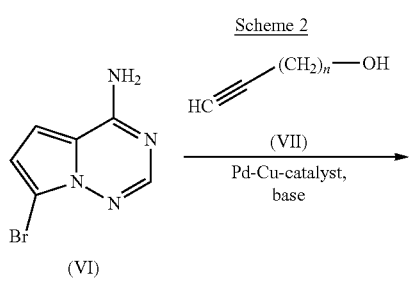

Bromopyrrolotriazine precursors of type (IIc) (scheme 3) can be prepared by metalation of compound (VI) with a metal such as magnesium or lithium or by halogen-metal exchange using an organo-magnesium or organo-lithium reagent. The preferred metal is magnesium which is introduced into (VI) by treatment with isopropylmagnesium bromide in a solvent such as THF or diethyl ether. The intermediate organo-metal species is then reacted with a cycloalkanone or heterocycloalkanone (XI) [R, R' are linked together to form a cycloalkyl or heterocycloalkyl ring] to give the tertiary alcohol (XIIa).

A complementary route leading to secondary alcohols of formula (XIIb) utilizes a Vilsmeier formylation reaction whereby aminopyrrolotriazine (XIII) is transformed into the aldehyde (XIV) (scheme 3). Side chain introduction is accomplished by subsequent addition of an appropriate Grignard reagent (XV) [R"=alkyl or cycloalkyl] in a solvent such as THF or diethyl ether. Finally, bromination of compounds (XIIa) and (XIIb), preferably using 1,3-dibromo-5,5-dimethylhydantoin, in an inert solvent such as THF or DMF provides the target pyrrolotriazines (IIc) and (IId), respectively.

The preparation of the starting compound pyrrolo[2,1-f][1,2,4]triazin-4-amine (XIII) has been described previously [see WO 2007/056170-A2 (Intermediate A)].

trifluoroacetic acid. Finally, bromination with 1,3-dibromo-5,5-dimethylhydantoin, as described above, provides the target pyrrolotriazine (IIe).

The alcohol precursors (XIIc) themselves are readily accessible by the synthetic route depicted in scheme 3 [cf. preparation of compound (XIIa)],

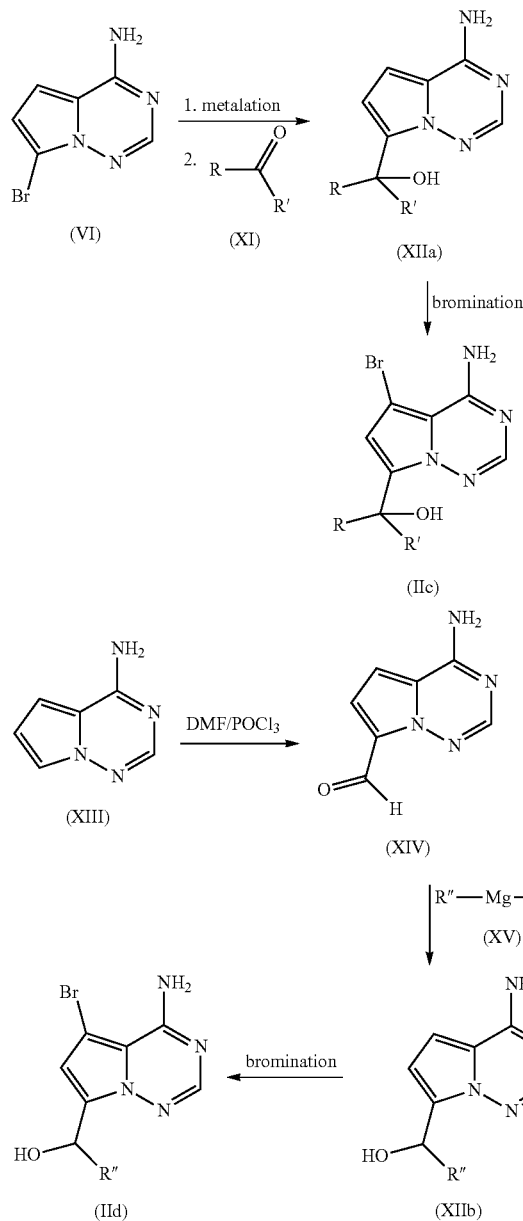

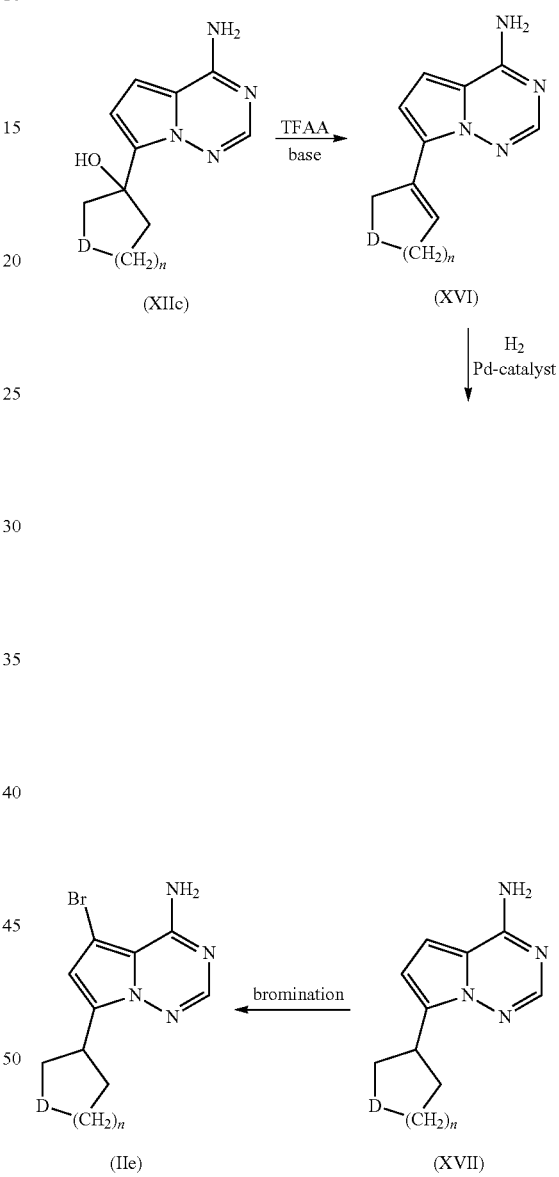

[D = e.g. CH$_2$ or N-Boc; n = 1 or 2].

Pyrrolotriazines of formula (II) wherein Z is representing an unsubstituted cycloalkyl or carbon-bonded aza-heterocyclyl group can be prepared by dehydration of a tertiary alcohol of formula (XIIc) to the unsaturated carbo- or heterocycle of formula (XVI), employing customary agents such as trifluoroacetic acid anhydride, trifluoromethanesulfonic acid anhydride, phosphorus(V) oxide, sulfuric acid or other strong acids (scheme 4). Subsequent catalytic hydrogenation using a conventional catalyst such as palladium on charcoal yields the saturated analog of formula (XVII). The hydrogenation step is preferably carried out in a solvent like methanol, ethanol or THF which contains a small amount of aqueous Pyrrolotriazines of formula (II) wherein Z is representing a 1,3-thiazol-4-yl group can be prepared by metalation of compound (VI), as described above, followed by reaction with chloroacetyl chloride to give the intermediate (XVIII), and then condensation with a thioamide or thiourea (XIX) [with R$^4$ as defined above] to yield the precursor compound (XX) (scheme 5). Bromination with 1,3-dibromo-5,5-dimethylhydantoin, as described above, finally provides the target pyrrolotriazine (IIf).

Scheme 5

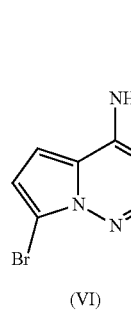
(VI)

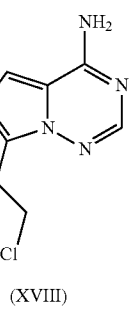
(XVIII)

(XIX)

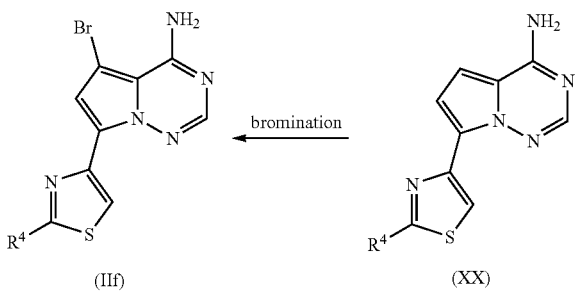
(IIf)    (XX)

Pyrrolotriazines of formula (II) wherein Z is representing an N-cyclic aminomethyl group can be obtained by reacting pyrrolotriazine (XIII) with formaldehyde and a cyclic amine of type (XXI) in an acidic solvent, such as acetic acid, or in a mixture of an acid with an organic solvent (scheme 6). Bromination of the resulting product (XXII) with 1,3-dibromo-5,5-dimethylhydantoin, as described above, then provides the target pyrrolotriazine (IIg).

Scheme 6

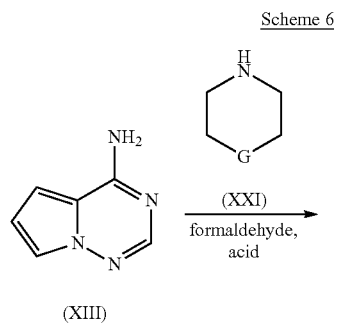
(XIII)

(XXI)

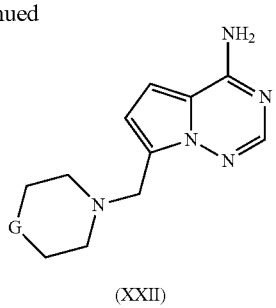
(XXII)

(IIg)

[G = e.g. CH$_2$, CH(OH), O or N-Boc].

The compounds of the formulae (V), (VII), (XI), (XV), (XIX) and (XXI) are either commercially available, known from the literature, or can be prepared from readily available starting materials by adaptation of standard methods described in the literature.

The compounds of the present invention have valuable pharmacological properties and can be used for the prevention and treatment of diseases in humans and animals.

The compounds of the present invention are potent and selective inhibitors of ALK1 kinase. They can therefore be used for the treatment and/or prevention of angiogenesis-related disorders, in particular angiogenesis-related ocular disorders.

For the present invention, the term "treatment" or "treating" includes inhibiting, delaying, relieving, mitigating, arresting, reducing or causing the regression of a disease, disorder, condition or state, the development and/or progression thereof, and/or the symptoms thereof. The term "prevention" or "preventing" includes reducing the risk of having, contracting or experiencing a disease, disorder, condition or state, the development and/or progression thereof and/or the symptoms thereof. The term prevention includes prophylaxis. Treatment or prevention of a disease, disorder, condition or state may be partial or complete.

Angiogenesis-related ocular disorders that may be treated and/or prevented with the compounds of the present invention include, but are not limited to, age-related macular degeneration (AMD), diabetic retinopathy, in particular diabetic macula edema (DME), other retinopathies such as choroidal neovascularisation (CNV), choroidal neovascular membrane (CNVM), cystoid macular edema (CME), epi-retinal membrane (ERM) and macular hole, hypertrophic changes of the retinal pigment epithelium (RPE), atrophic changes of the retinal pigment epithelium, retinal detachment, choroidal vein occlusion, retinal vein occlusion, corneal angiogenesis following, for example, keratitis, cornea transplantation or keratoplasty, corneal angiogenesis due to hypoxia (e.g., induced by extensive contact lens wearing), pterygium conjunctivae, subretinal edema, and intraretinal edema.

In the context of the present invention, the term age-related macular degeneration (AMD) encompasses both wet (or exudative, neovascular) and dry (or non-exudative, non-neovascular) manifestations of AMD.

The compounds of the present invention can additionally be used for the treatment and/or prevention of inflammatory diseases associated with angiogenesis, such as rheumatoid arthritis, psoriasis, contact dermatitis, asthma, pulmonary hypertension, multiple sclerosis, and inflammatory diseases of the bowel such as Crohn's disease. Fibrotic diseases, such as fibrosis and cirrhosis, may also be treated and/or prevented with the compounds of the present invention.

By virtue of their activity profile, the compounds of the present invention are particularly suitable for the treatment and/or prevention of ocular disorders, such as age-related macular degeneration (AMD), choroidal neovascularisation (CNV), diabetic retinopathy, and diabetic macula edema (DME).

The disorders mentioned above have been well characterized in humans, but also exist with a similar etiology in other animals, including mammals, and can be treated in these with the compounds of the present invention.

Thus, the present invention further relates to the use of the compounds according to the invention for the treatment and/or prevention of disorders, especially of the aforementioned disorders.

The present invention further relates to the use of the compounds according to the invention for preparing a pharmaceutical composition for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

Compounds of the present invention may be administered as the sole pharmaceutical agent or in combination with one or more additional therapeutic agents where the combination causes no unacceptable adverse effects. This combination therapy includes administration of a single pharmaceutical dosage formulation which contains a compound of formula (I), as defined above, and one or more additional therapeutic agents, as well as administration of a compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (i.e., concurrently) or at separately staggered times (i.e., sequentially).

In particular, the compounds of the present invention may be used in fixed or separate combination with inhibitors of VEGF-mediated angiogenesis, such as, for example, ACTB-1003, aflibercept, apatinib, axitinib, bevacizumab, bevasiranib, BMS-690514, brivanib, cediranib, CT-322, dovitinib, E7080, foretinib, KH-902, linifanib, MGCD-265, motesanib, OTS-102, pazopanib, pegaptanib, ranibizumab, regorafenib, ruboxystaurin, sorafenib, SU-14813, sunitinib, telatinib, TG-100801, tivozanib, TSU-68, vandetanib, vargatef, vatalanib and XL-184, or with inhibitors of other signaling pathways, such as, for example, ACU-4429, disulfuram, E-10030, fenretinide, mecamylamine, PF-04523655, sirolimus, sonepcizumab, tandospirone and volociximab.

Thus, in a further embodiment, the present invention relates to pharmaceutical compositions comprising at least one of the compounds according to the invention and one or more additional therapeutic agents for the treatment and/or prevention of disorders, especially of the aforementioned disorders.

The compounds of the present invention may also be utilized, as such or in compositions, in research and diagnostics, or as analytical reference standards and the like.

In another aspect, the present invention relates to pharmaceutical compositions comprising at least one of the compounds according to the invention together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary, nasal, lingual, sublingual, buccal, rectal, dermal, transdermal, conjunctival, subconjunctival, intravitreal, otic or topical routes.

The compounds according to the invention can be administered in application forms suitable for these administration routes.

Suitable for oral administration are application forms which function according to the prior art and deliver the compounds according to the invention rapidly and/or in modified fashion, and which contain the compounds according to the invention in crystalline, amorphous and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (e.g., hard or soft gelatin capsules), sugar-coated tablets, granules, pellets, powders, emulsions, suspensions, aerosols or solutions.

Parenteral administration can take place with avoidance of an absorption step (e.g., intravenous, intraarterial, intracardiac, intraspinal or intralumbar) or with inclusion of an absorption (e.g., intramuscular, subcutaneous, intracutaneous, percutaneous or intraperitoneal). Application forms suitable for parenteral administration are, inter al., preparations for injection and infusion in the form of solutions, suspensions, emulsions, lyophilisates or sterile powders.

Forms suitable for other administration routes include, for example, pharmaceutical forms for inhalation (e.g., powder inhalers, nebulizers), nasal drops, solutions or sprays, tablets or capsules for lingual, sublingual or buccal administration (e.g., troches, lozenges), suppositories, ear and eye preparations (e.g., drops, ointments), vaginal capsules, aqueous suspensions (lotions, shaking mixtures), lipophilic suspensions, ointments, creams, milk, pastes, foams, dusting powders, and transdermal therapeutic systems (e.g., patches).

The compounds according to the invention can be converted into the recited application forms in a manner known per se by mixing with inert, non-toxic, pharmaceutically suitable excipients. These excipients include, inter al., carriers (e.g., microcrystalline cellulose, lactose, mannitol), solvents (e.g., liquid polyethylene glycols), emulsifiers (e.g., sodium dodecyl sulfate), surfactants (e.g., polyoxysorbitan oleate), dispersants (e.g., polyvinylpyrrolidone), synthetic and natural polymers (e.g., albumin), stabilizers (e.g., antioxidants such as, for example, ascorbic acid), colorants (e.g., inorganic pigments such as, for example, iron oxides), and taste and/or odour masking agents.

It has generally proved advantageous to administer on parenteral administration amounts of about 0.001 to 1 mg/kg, preferably about 0.01 to 0.5 mg/kg, of body weight to achieve effective results. On oral administration, an exemplary dose range is about 0.01 to 100 mg/kg, preferably about 0.01 to 20 mg/kg, and more preferably about 0.1 to 10 mg/kg of body weight.

Nevertheless, actual dosage levels and time course of administration of the active ingredients in the pharmaceutical compositions of the invention may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit must be exceeded. It may in the event of administration of larger amounts be advisable to divide these into multiple individual doses spread over the day.

For the treatment and/or prevention of ocular disorders, as described above, the preferred route for administering the compounds of the invention is topically at the eye or by an ocular drug delivery system. Intraocular injections are another way to administer the compounds of the present invention that is suitable for such purposes.

Delivery to areas within the eye can be accomplished by injection, employing a cannula or another invasive device designed to introduce precisely metered amounts of a desired formulation to a particular compartment or tissue within the eye (e.g., posterior chamber or retina). An intraocular injection may be into the vitreous (intravitreal), under the conjunctiva (subconjunctival), behind the eye (retrobulbar), into the sclera, or under the Capsule of Tenon (sub-Tenon), and may be in a depot form. Other intraocular routes of administration and injection sites and forms are also contemplated and are within the scope of the invention.

The compounds according to the invention may be formulated in a manner known to those skilled in the art so as to give adequate delivery to the back of the eye, which may be by regular dosing, such as with eye drops, or by using a delivery system to give a controlled release, such as slow release, of the compounds according to the invention.

Preferred ocular formulations for the compounds of the present invention include aqueous solutions, suspensions or gels of these compounds in the form of drops of liquid, liquid washes, sprays, ointments or gels, in admixture with excipients suitable for the manufacture and use of such application forms. Alternatively, the compounds of the present invention may be applied to the eye via liposomes or other ocular delivery systems that are known in the art.

Appropriate dosage levels may be determined by any suitable method known to one skilled in the art of treating eye diseases. Preferably, the active substance is administered at a frequency of 1 to 4 times per day for topical administration, or less often if a drug delivery system is used. Typically, an ocular formulation intended for topical application contains the active ingredient in a concentration range of about 0.001% to 10%.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

A. Examples

Abbreviations and Acronyms:
Ac acetyl
aq. aqueous (solution)
Boc tert-butoxycarbonyl
br, broad ($^1$H NMR signal)
Cbz benzyloxycarbonyl
Celite® registered trademark of Celite Corp. brand of diatomaceous earth
conc. concentrated
DCI direct chemical ionization (MS)
DCM dichloromethane
DMF N,N-dimethylformamide
DMSO dimethylsulfoxide
e.e. enantiomeric excess
EI electron impact ionization (MS)
ent enantiomer, enantiomerically pure
eq. equivalent(s)
ESI electro-spray ionization (MS)
Et ethyl
EtOAc ethyl acetate
Fmoc (9H-fluoren-9-ylmethoxy)carbonyl
GC/MS gas chromatography-coupled mass spectroscopy
h hour(s)
Hal halogen
$^1$H NMR proton nuclear magnetic resonance spectroscopy
HPLC high performance liquid chromatography
LC/MS liquid chromatography-coupled mass spectroscopy
Me methyl
MeOH methanol
min minute(s)
MS mass spectroscopy
of th. of theory (chemical yield)
PdCl$_2$(dppf) [1,1'-bis(diphenylphosphino)ferrocene]dichloropalladium(II)
Ph phenyl
rac racemic, racemate
R$_f$ TLC retention factor
rt room temperature
R$_t$ retention time (HPLC)
satd. saturated
TBAF tetrabutylammonium fluoride
tBu tert-butyl
tert tertiary
TFA trifluoroacetic acid
TFAA trifluoroacetic acid anhydride
THF tetrahydrofuran
TLC thin layer chromatography
Preparative HPLC Purification Methods:
Method 1:
  Device: Gilson Abimed HPLC, binary pump system; column: ReproSil C18, 250 mm×30 mm; eluent A: water/1% ammonia, eluent B: acetonitrile; gradient: 0-3 min 10% B, 5.01-31 min 95% B, 31 min 95% B; flow rate: 50 mL/min; UV detection: 210 nm.
Method 2:
  Device: Gilson Abimed HPLC, binary pump system; column: Kromasil-100A C18, 5 µm, 250 mm×30 mm; eluent A: water/0.05-0.5% TFA, eluent B: acetonitrile; gradient: 0-5 min 5% B, 5.01-10 min 10% B, 10.01-20 min 40% B, 20.01-

27 min 50% B, 27.01-40 min 60% B, 40.01-45 min 90% B, 45.01-60 min 100% B; flow rate: 15-60 mL/min; LTV detection: 210 nm.

Method 3:
Device: Gilson Abimed HPLC, binary pump system; column: Grom-Sil-120 ODS-4HE, 250 mm×mm; eluent A: water, eluent B: acetonitrile; gradient: 0-3 min 10% B, 3.01-35 min 98% B, 35.01-40 min 98% B; flow rate: 50 mL/min; LTV detection: 210 nm.

Method 4:
Device: Gilson Abimed HPLC, binary pump system; column: Grom-Sil-120 ODS-4HE, 250 mm×30 mm; eluent A: water/0.5% ammonia, eluent B: acetonitrile; gradient: 0-3 min 10% B, 3.01-35 min 98% B, 35.01-40 min 98% B; flow rate: 50 mL/min; UV detection: 210 nm.

Method 5:
Device: Gilson Abimed HPLC, binary pump system; column; Chromatorex C18 10 μm, 250 mm×30 mm; eluent A: water, eluent B: acetonitrile; gradient: 0-3 min 10% B, 5.01-31 min 90% B, 31 min 90% B; flow rate: 50 mL/min; UV detection: 210 nm.

Method 6:
Device: Gilson Abimed HPLC, binary pump system; column: Chromatorex C18 10 μm, 250 mm×30 mm; eluent A: water/0.5% TFA, eluent B: acetonitrile; gradient: 0-3 min 10% B, 5.01-31 min 90% B, 31 min 90% B; flow rate: 50 mL/min; UV detection: 210 nm.

Method 7:
Device: Gilson Abimed HPLC, binary pump system; column: ReproSil C18 10 μm, 250 mm×40 mm; eluent A: water, eluent B: acetonitrile; gradient: 0-3 min 10% B, 5.01-31 min 95% B, 31 min 95% B; flow rate: 50 mL/min; UV detection: 210 nm.

Method 8:
Device: Gilson Abimed HPLC, binary pump system; column: ReproSil C18 10 μm, 250 mm×30 mm; eluent A: water, eluent B: acetonitrile; gradient: 0-3 min 10% B, 5.01-31 min 95% B, 31 min 95% B; flow rate: 50 mL/min; UV detection: 210 nm.

Method 9:
Device: Gilson Abimed HPLC, binary pump system; column: Waters Sunfire C18 5 μm, 250 mm×20 mm; eluent A: water, eluent B: acetonitrile; gradient: 0 min 20% B, 15 min 60% B, 15.01-19 min 20% B; flow rate: 25 mL/min; UV detection: 210 nm.

Analytical HPLC, LC/MS and GC/MS Methods:

Method 1 (HPLC):
Instrument: Agilent 1100 with DAD detection; column: Agilent Zorbax Eclipse XDB-C8 4.6, 150 mm×5 mm; eluent A: 0.01% TFA in water, eluent B: 0.01% TFA in acetonitrile; gradient: 0-1 min 10% B, 4-5 min 90% B, 5.5 min 10% B; flow rate: 2.0 mL/min; temperature: 30° C.; UV detection: 210 nm.

Method 2 (HPLC):
Instrument: HP 1100 with DAD detection; column: Kromasil 100 RP-18, 60 mm×2.1 mm, 3.5 μm; eluent A: 5 mL perchloric acid (70%)/L water, eluent B: acetonitrile; gradient: 0 min 2% B, 0.5 min 2% B, 4.5 min 90% B, 6.5 min 90% B, 6.7 min 2% B, 7.5 min 2% B; flow rate: 0.75 mL/min; temperature: 30° C.; UV detection: 210 nm.

Method 3 (HPLC):
Instrument: HP 1100 with DAD detection; column: Kromasil 100 RP-18, 60 mm×2.1 mm, 3.5 μm; eluent A: 5 mL perchloric acid (70%)/L water, eluent B: acetonitrile; gradient: 0 min 2% B, 0.5 min 2% B, 4.5 min 90% B, 9 min 90% B, 9.2 min 2% B, 10 min 2% B; flow rate: 0.75 mL/min; temperature: 30° C.; UV detection: 210 nm.

Method 4 (LC/MS):
Instrument: Micromass Platform LCZ with HPLC Agilent 1100 Series; column: Thermo Hypersil GOLD 3μ, 20 mm×4 mm; eluent A: 1 L water+0.5 mL 50% formic acid, eluent B: 1 L acetonitrile+0.5 mL 50% formic acid; gradient: 0.0 min 100% A→0.2 min 100% A→2.9 min 30% A→3.1 min 10% A→5.5 min 10% A; temperature: 50° C.; flow rate: 0.8 mL/min; UV detection: 210 nm.

Method 5 (LC/MS):
Instrument: Micromass ZQ with HPLC Waters Alliance 2795/HP 1100; column: Phenomenex Synergi 2.5μ MAX-RP 100A Mercury, 20 mm×4 mm; eluent A: 1 L water+0.5 mL 50% formic acid, eluent B: 1 L acetonitrile+0.5 mL 50% formic acid; gradient: 0.0 min 90% A→2.5 min 30% A→3.0 min 5% A→4.0 min 5% A; flow rate: 2 mL/min; temperature: 50° C.; UV detection: 210 nm.

Method 6 (LC/MS):
Instrument: Micromass Quattro Premier with Waters UPLC Acquity; column: Thermo Hypersil GOLD 1.9μ, 50 mm×1 mm; eluent A: 1 L water+0.5 mL 50% formic acid, eluent B: 1 L acetonitrile+0.5 ml 50% formic acid; gradient: 0.0 min 90% A→0.1 min 90% A→1.5 min 10% A→2.2 min 10% A; temperature: 50° C.; flow rate: 0.33 mL/min; UV detection: 210 nm.

Method 7 (LC/MS):
Instrument: Micromass ZQ with HPLC Waters Alliance 2795; column: Phenomenex Synergi 2.5μ MAX-RP 100A Mercury, 20 mm×4 mm; eluent A: 1 L water+0.5 mL 50% formic acid, eluent B: 1 L acetonitrile+0.5 mL 50% formic acid; gradient: 0.0 min 90% A→0.1 min 90% A→3.0 min 5% A→4.0 min 5% A→4.01 min 90% A; flow rate: 2 mL/min; temperature: 50° C.; UV detection: 210 nm.

Method 8 (GC/MS):
Instrument: Micromass GCT, GC6890; column: Restek RTX-35, 15 m×200 μm×0.33 μm; constant flow with helium: 0.88 mL/min; oven: 70° C.; inlet: 250° C.; gradient: 70° C., 30° C./min→310° C. (keep for 3 min).

Method 9 (HPLC):
Instrument: Agilent 1100 with DAD detection; column: Merck Chromolith Speed ROD, 150 mm×5 mm; eluent A: 0.01% formic acid in water, eluent B: acetonitrile; gradient: 0 min 5% B, 2.5 min 95% B, 3 min 95% B; flow rate: 5.0 mL/min; temperature: 40° C.; UV detection: 210 nm.

Method 10 (LC/MS):
Instrument: Waters Acquity SQD UPLC System; column: Waters Acquity UPLC HSS T3 1.8μ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; temperature: 50° C.; flow rate: 0.40 mL/min; UV detection: 208-400 nm.

General Synthetic Method 1:
Suzuki coupling of 5-bromopyrrolo[2,1-f][1,2,4]triazine derivatives with arylboronic acids or esters:

-continued

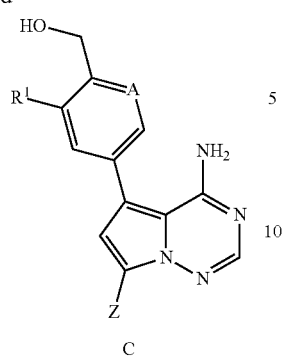

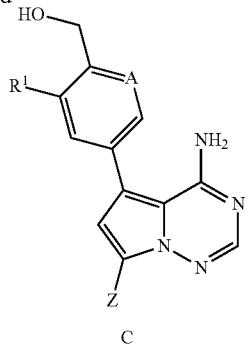

A 5-bromopyrrolo[2,1-f][1,2,4]triazine A (about 0.5 mmol), arylboronic acid B (1.2 equivalents) or a corresponding boronic ester, e.g., a dimethyl boronate or pinacolato boronate, and tetrakis(triphenylphosphine)palladium(0) (0.1 equivalents) are dissolved in a mixture of 1,4-dioxane (about 4.0 mL) and 2 M aqueous sodium carbonate solution (1.5 mL) in a microwave reactor vial. The reaction vessel is crimp-capped, and the mixture is heated to 140° C. for 1 h in a single-mode microwave device. After cooling, the reaction mixture is filtered over a pad of Celite which is rinsed with 1,4-dioxane to elute all organic material. The combined filtrate is evaporated to dryness under reduced pressure, and the residue is purified by preparative HPLC to give the target compound C.

General Synthetic Method 2:

Borylation of arylbromides and subsequent Suzuki coupling with 5-bromopyrrolo[2,1-f][1,2,4]-triazine derivatives without isolation of the intermediate arylboronic acid or ester:

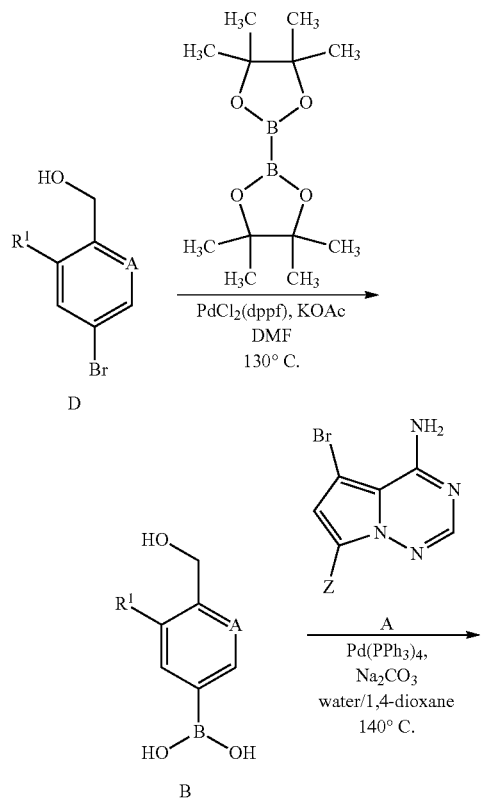

Arylbromide D (about 0.5 mmol) is dissolved in DMF (3 mL) in a microwave reactor vessel, argon is bubbled through the solution for 5 min, and [1,1'-bis(diphenylphosphino)ferrocene]dichloropalladium(II)-dichloromethane complex (0.1 equivalents), potassium acetate (3 equivalents) and bis(pinacolato)diboron (1.2 equivalents) are added. The vessel is crimp-capped, and the mixture is heated to 130° C. for 60 min in a single-mode microwave device. Then, the suspension is filtered, the filtrate is transferred to another microwave process vial, and tetrakis(triphenylphosphine)palladium(0) (0.1 equivalents), 2 M aqueous sodium carbonate solution (4 equivalents) and the 5-bromopyrrolo[2,1-f][1,2,4]triazine A (1 equivalent) are added. The vial is crimp-capped, and the mixture is heated to 140° C. for 1 h in a single-mode microwave device. The crude reaction mixture thus obtained is directly injected onto a preparative HPLC column for separation and purification of the target compound C.

Starting Materials and Intermediates

Intermediate 1A

[2,6-Difluoro-4-(4,4,5,5-tetramethyl-1,3,2-dioxaborolan-2-yl)phenyl]methanol

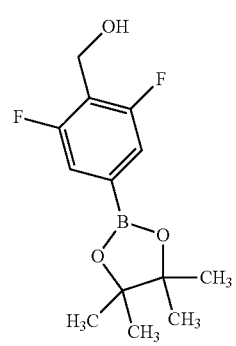 [SMILES: CC1(C)OB(c2cc(F)c(CO)c(F)c2)OC1(C)C]

(4-Bromo-2,6-difluorophenyl)methanol (1.03 g, 4.62 mmol) was dissolved in dry 1,4-dioxane (10 mL). Argon was bubbled through the solution, then [1,1'-bis(diphenylphosphino)ferrocene]-dichloropalladium-dichloromethane complex (302 mg, 0.37 mmol, 0.08 eq.), anhydrous potassium acetate (907 mg, 9.24 mmol, 2 eq.) and bis(pinacolato)diboron (1.23 g, 4.85 mmol, 1.05 eq.) were added, and the mixture was heated to 130° C. for 1 h in a single-mode microwave device. Upon cooling, the mixture was filtered, and the solvent was removed under reduced pressure. Cyclohexane (200 mL) was added to the residue, and the mixture was vigorously stirred for 30 min. Undissolved material was then removed by filtration, the cyclohexane was distilled off, and the residue was purified by flash chromatography over silica gel (dichloromethane/acetonitrile gradient). Fractions containing the product were combined and evaporated. The title compound crystallized spontaneously as a brownish solid. Yield: 790 mg (63% of th.).

GC-MS (method 8): $R_t$=5.36 min; MS (EI): m/z (%)=270.3 (15) [M]$^+$.

Intermediate 2A

[3,5-Difluoro-4-(hydroxymethyl)phenyl]boronic acid

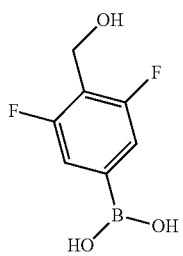 [SMILES: OCc1c(F)cc(B(O)O)cc1F]

[4-({[tert-Butyl(dimethyl)silyl]oxy}methyl)-3,5-difluorophenyl]boronic acid (19.3 g, 63.9 mmol; crude material, prepared by the method of Hattori, *Bioorg. Med. Chem.* 2006, 14, 3258-3262) was dissolved in 400 mL aqueous acetic acid (66%) and stirred at 40° C. for 5 h. The solution was then evaporated under reduced pressure, and the residue was purified by flash chromatography over silica gel (gradient elution from 0% to 2% methanol in dichloromethane) to give 3.46 g (25% of th., LC-MS purity 87%) of the title compound.

LC-MS (method 7): $R_t$=0.50 min; MS (ESIpos): m/z (%)=171.2 (100) [M+OH]$^+$, MS (ESIneg): m/z (%)=187.3 (100) [M–H]$^-$.

Intermediate 3A (4-Bromo-2-chlorophenyl)methanol

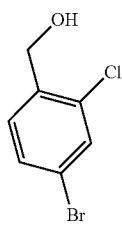

The title compound was prepared according to the procedure described in WO 2004/074270-A2 [Example A(147), step 1].

$^1$H NMR (400 MHz, CDCl$_3$): δ (ppm)=2.00 (br, 1H), 4.74 (s, 2H), 7.38 (d, 1H), 7.43 (dd, 1H), 7.53 (d, 1H).

Intermediate 4A (4-Bromo-2-methylphenyl)methanol

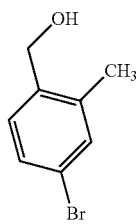

The title compound was prepared according to the procedure described in EP 1 544 208-A1 (Reference Example 14).

$^1$H NMR (400 MHz, CDCl$_3$): δ (ppm)=1.62 (t, 3H), 2.32 (s, 3H), 4.64 (d, 2H), 7.23 (d, 1H), 7.32 (s, 1H), 7.33 (d, 1H).

Intermediate 5A (5-Bromopyridin-2-yl)methanol

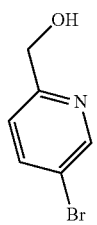

Methyl 5-bromopyridine-2-carboxylate (2.00 g, 9.27 mmol) was dissolved in ethanol (20.0 mL). Sodium borohydride (1.05 g, 27.8 mmol) was added at 0° C., and the mixture was stirred at room temperature for 18 h. The mixture was then concentrated under reduced pressure, quenched with 1 N hydrochloric acid, neutralized with solid potassium carbonate and extracted with dichloromethane. The organic layer was dried over magnesium sulfate and evaporated to give 1.57 g (90% of th.) of the title compound.

LC-MS (method 6): $R_t$=0.56 min; MS (ESIpos): m/z (%)=188.0 (100) [M–H]$^+$.

Intermediate 6A

[6-(Hydroxymethyl)pyridin-3-yl]boronic acid

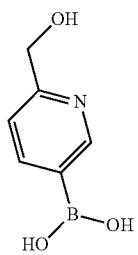 [SMILES: OCc1ccc(B(O)O)cn1]

To a solution of Intermediate 5A (1.50 g, 7.98 mmol) and bis(pinacolato)diboron (2.23 g, 8.28 mmol) in degassed DMF (120 mL) was added under an argon atmosphere 1,1'-bis (diphenylphosphino)ferrocene-palladium(II) chloride (292 mg, 0.40 mmol) and potassium acetate (2.35 g, 23.9 mmol). The mixture was heated to 80° C. for 18 h and then cooled to room temperature. The suspension was filtered, and the residue was washed with dioxane. The combined filtrates were concentrated under reduced pressure, and the oily residue was taken up in 50 mL ethyl acetate and 50 mL cyclohexane and allowed to stand at room temperature overnight. The resulting precipitate was collected by filtration and discarded. The filtrate was evaporated, and the residue was dissolved again in 100 mL ethyl acetate and extracted twice with 50 mL water. The aqueous layer was concentrated to give 690 mg (56% of th.) of the title compound which was used without further purification.

LC-MS (method 6): $R_t$=0.18 min; MS (ESIpos): m/z (%)=154.0 (100) [M+H]$^+$.

Intermediate 7A 3-(4-Aminopyrrolo[2,1-f][1,2,4]triazin-7-yl)prop-2-yn-1-ol

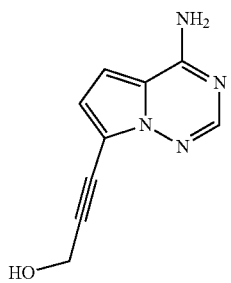 [SMILES: Nc1ncnn2c(C#CCO)ccc12]

The starting material 7-bromopyrrolo[2,1-f][1,2,4]triazin-4-amine was synthesized according to the procedure described in WO 2007/056170-A2 (Intermediate B).

7-Bromopyrrolo[2,1-f][1,2,4]triazin-4-amine (1.0 g, 4.69 mmol), copper(I) iodide (89 mg, 0.47 mmol, 0.1 eq.) and tetrakis(triphenylphosphine)palladium(0) (542 mg, 0.47 mmol, 0.1 eq.) were charged into a microwave reactor vial and evacuated for 1 h. The vessel was then vented with argon, pyrrolidine (15 mL) and 2-propyn-1-ol (2.63 g, 47 mmol, 10 eq.) were added, and the vessel was crimp-capped and heated to 85° C. for 120 min in a single-mode microwave device. After cooling, the reaction mixture was poured into 120 mL of concentrated aqueous ammonium chloride solution which was extracted twice with ethyl acetate. The combined organic layers were dried over anhydrous sodium sulfate and evaporated, and the residue was purified by flash chromatography (Biotage silica column, ethyl acetate). The resulting product (222 mg) appeared pure by LC-MS (method 6) and was used for further transformations.

HPLC (method 2): $R_t$=2.59 min;

LC-MS (method 6): $R_t$=0.28 min; MS (ESIpos): m/z (%)=189.2 (100) [M+H]$^+$.

Intermediate 8A and Intermediate 9A 3-(4-Aminopyrrolo[2,1-f][1,2,4]triazin-7-yl)propan-1-ol and 7-Propylpyrrolo[2,1-f][1,2,4]triazin-4-amine

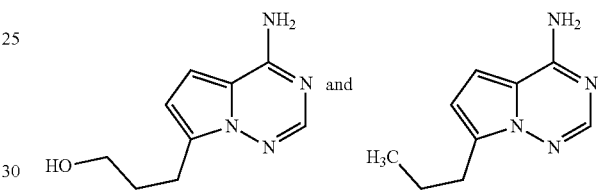

Intermediate 7A (444 mg, 2.36 mmol) was dissolved in acetic acid (18 mL) under an argon atmosphere. Platinum(IV) oxide (40 mg, 0.18 mmol, 0.08 eq.) was added, and the mixture was vigorously stirred for 3 h at room temperature under an atmosphere of hydrogen at ambient pressure. The catalyst was then removed by filtration, the solvent was distilled off, and the residue was subjected to flash chromatography (Biotage silica column, cyclohexane/ethyl acetate gradient). The Intermediates 8A (185 mg, 41% of th.) and 9A (170 mg, 41% of th.) were obtained in two distinct chromatographic fractions:

Intermediate 8A:

HPLC (method 2): $R_t$=2.68 min;

LC-MS (method 4): $R_t$=0.83 min; MS (ESIpos): m/z (%)=193.1 (100) [M+H]$^+$, MS (ESIneg): m/z (%)=191.1 (100) [M−H]$^-$.

$^1$H NMR (400 MHz, d$_6$-DMSO): δ (ppm)=1.80 (m, 2H), 2.86 (t, J=7.7 Hz, 2H), 3.45 (m, 2H), 4.49 (t. J=5.1 Hz, 1H), 6.41 (d, J=4.2 Hz, 1H), 6.69 (d, J=4.2 Hz, 1H), 7.50 (br. s, 2H), 7.78 (s, 1H).

Intermediate 9A:

HPLC (method 1): $R_t$=3.22 min;

LC-MS (method 4): $R_t$=1.23 min; MS (ESIpos): m/z (%)=177.1 (100) [M+H]$^+$, MS (ESIneg): m/z (%)=175.2 (30) [M−H]$^-$.

Intermediate 10A 3-(4-Amino-5-bromopyrrolo[2,1-f][1,2,4]triazin-7-yl)propan-1-ol

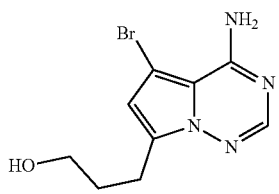 [SMILES: Nc1ncnn2c(CCCO)cc(Br)c12]

Intermediate 8A (105 mg, 0.55 mmol) was dissolved in THF (8.75 mL) and cooled to −20° C. 1,3-Dibromo-5,5-dimethylhydantoin (78.1 mg, 0.5 eq.) was added, and the mixture was stirred at −20° C. for 1 h. The reaction was then quenched with 0.5 mL concentrated aqueous sodium dithionite solution, warmed to room temperature and partitioned between ethyl acetate and water. The organic phase was dried over anhydrous sodium sulfate, and the solvent was distilled off. Yield: 145 mg (98% of th.).

HPLC (method 1): $R_t$=2.96 min; HPLC (method 2): $R_t$=2.95 min;

LC-MS (method 5): $R_t$=1.03 min; MS (ESIpos): m/z (%)=271.0 (100) and 273.0 (100) [M+H]$^+$, MS (ESIneg): m/z (%)=269.0 (99) and 271.0 (100) [M−H]$^-$.

$^1$H NMR (400 MHz, $d_6$-DMSO): δ (ppm)=1.75 (m, 2H), 2.83 (t, J=8.1 Hz, 2H), 3.43 (m, 2H), 4.50 (t, J=5.4 Hz, 1H), 6.62 (s, 1H), 7.81 (s, 1H).

Intermediate 11A

5-Bromo-7-propylpyrrolo[2,1-f][1,2,4]triazin-4-amine

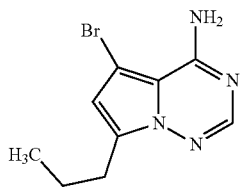

Intermediate 9A (110 mg, 0.62 mmol) was dissolved in THF (4.44 mL) and cooled to −20° C. 1,3-Dibromo-5,5-dimethylhydantoin (89 mg, 0.5 eq.) was added, and the mixture was stirred at −20° C. for 1 h. The reaction was then quenched with 0.5 mL concentrated aqueous sodium dithionite solution, warmed to room temperature and partitioned between ethyl acetate and water. The organic phase was dried over anhydrous sodium sulfate, and the solvent was distilled off. Yield: 154 mg (85% pure, 82% of th.).

HPLC (method 1): $R_t$=3.78 min;

LC-MS (method 7): $R_t$=1.55 min; MS (ESIpos): m/z (%)=255.0 (99) and 257.2 (100) [M+H]$^+$.

$^1$H NMR (400 MHz, $d_6$-DMSO): δ (ppm)=0.91 (t, J=7.3 Hz, 3H), 1.65 (m, 2H), 2.79 (t, J=7.6 Hz, 2H), 3.31 (s, 2H), 6.63 (s, 1H), 7.95 (s, 1H).

Intermediate 12A 4-(4-Aminopyrrolo[2,1-f][1,2,4]triazin-7-yl)but-3-yn-1-ol

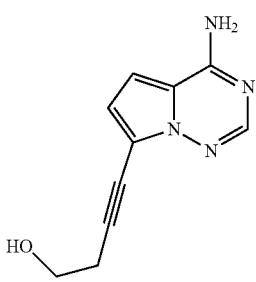 [SMILES: Nc1ncnn2c(C#CCCO)ccc12]

7-Bromopyrrolo[2,1-f][1,2,4]triazin-4-amine (1.0 g, 4.69 mmol), copper(I) iodide (89 mg, 0.47 mmol, 0.1 eq.) and tetrakis(triphenylphosphine)palladium(0) (542 mg, 0.47 mmol, 0.1 eq.) were charged into a microwave reactor vial and evacuated for 1 h. The vessel was then vented with argon, pyrrolidine (15 mL) and 3-butyn-1-ol (3.36 g, 47 mmol, 10 eq.) were added, and the vessel was crimp-capped and heated to 85° C. for 120 min in a single-mode microwave device. After cooling, the reaction mixture was poured into 120 mL of concentrated aqueous ammonium chloride solution and extracted twice with ethyl acetate. The combined organic layers were dried over anhydrous sodium sulfate and evaporated, and the residue was purified by flash chromatography (Biotage silica column, ethyl acetate). The resulting product (735 mg) was sufficiently pure (66% by HPLC) for further transformations.

HPLC (method 2): $R_t$=2.77 min;

LC-MS (method 4): $R_t$=0.96 min; MS (ESIpos): m/z (%)=203.1 (100) [M+H]$^+$, MS (ESIneg): m/z (%)=201.1 (100) [M−H]$^-$.

Intermediate 13A 4-(4-Aminopyrrolo[2,1-f][1,2,4]triazin-7-yl)butan-1-ol

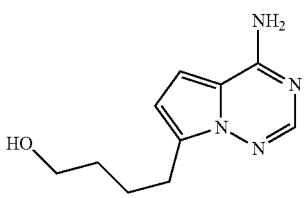 [SMILES: Nc1ncnn2c(CCCCO)ccc12]

Intermediate 12A (607 mg, 3.00 mmol) was dissolved in acetic acid (64 mL), and platinum(IV) oxide (50 mg, 0.22 mmol, 0.07 eq.) was added. The mixture was stirred under an atmosphere of hydrogen at ambient pressure for 15 h. The catalyst was then removed by filtration, the filtrate was evaporated under reduced pressure, and the residue was purified by flash chromatography (Biotage silica column, ethyl acetate). Yield: 350 mg (57% of th.).

HPLC (method 2): $R_t$=2.92 min;
LC-MS (method 4): $R_t$=0.94 min; MS (ESIpos): m/z (%)=207.1 (100) [M+H]$^+$, MS (ESIneg): m/z (%)=205.3 (100) [M−H]$^−$.

Intermediate 14A 4-(4-Amino-5-bromopyrrolo[2,1-f][1,2,4]triazin-7-yl)butan-1-ol

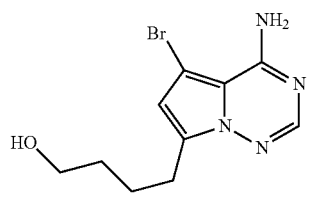 [SMILES: Nc1ncnn2c(CCCCO)cc(Br)c12]

Intermediate 13A (330 mg, 1.60 mmol) was dissolved in THF (26 mL) at −20° C., and 1,3-dibromo-5,5-dimethylhydantoin (229 mg, 0.80 mmol) was added. The mixture was stirred at −20° C. for 1 h. The reaction was then quenched with concentrated aqueous sodium sulfite solution (0.5 mL). Ethyl acetate was added, the aqueous layer was separated, and the organic layer was dried over sodium sulfate and evaporated. The crude product was subsequently purified by preparative HPLC (method 2) giving 175 mg (84% of th.) of the title compound.

HPLC (method 1): $R_t$=3.13 min;
LC-MS (method 5): $R_t$=1.23 min; MS (ESIpos): m/z (%)=285.0 (98) and 287.0 (100) [M+H]$^+$, MS (ESIneg): m/z (%)=283.0 (100) and 285.0 (98) [M−H]$^−$.
$^1$H-NMR (400 MHz, $d_6$-DMSO): δ (ppm)=1.39-1.48 (m, 2), H) 1.60-1.69 (m, 2H), 3.31 (t, J=7.3 Hz, 2H), 3.40 (m, 2H), 4.46 (br. s, 1H), 6.61 (s, 1H), 7.82 (s, 1H).

Intermediate 15A

4-Aminopyrrolo[2,1-f][1,2,4]triazine-7-carbaldehyde

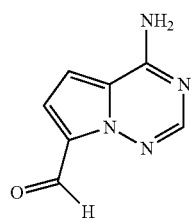 [SMILES: Nc1ncnn2c(C=O)ccc12]

The starting material pyrrolo[2,1-f][1,2,4]triazin-4-amine was synthesized according to the procedure described in WO 2007/056170-A2 (Intermediate A).

Pyrrolo[2,1-f][1,2,4]triazin-4-amine (20.5 g, 152 mmol) was dissolved in 150 mL DMF. Under ice cooling, phosphoryl chloride (31.3 mL, 336 mmol) was added dropwise at such a rate that the internal temperature did not rise above 30° C. The mixture was then heated for 2 days at 50° C. After cooling, another portion of phosphoryl chloride (14.2 mL, 152 mmol) was added, and stirring was continued for another 24 h at 50° C. After cooling, the reaction batch was slowly poured into a mixture of 2.0 L saturated aqueous sodium bicarbonate solution and 2.0 L ethyl acetate. Solid sodium bicarbonate was added until gas evolution stopped. The layers were separated, the aqueous layer was extracted with 0.5 L ethyl acetate, and the combined organic phases were dried over sodium sulfate and concentrated. The residue was suspended in 100 mL diisopropyl ether, stirred at room temperature for 10 min and then filtered. The dried residue was stirred in 6 N hydrochloric acid (500 mL) for 1 h at 50° C. and then poured into an ice/water mixture (1000 mL). The mixture was carefully neutralized with solid sodium bicarbonate, stirred for 30 min at room temperature and then filtered again. The residue was washed with water and ligroin to yield 20.6 g (83% of th.) of white crystals which were used in the next step without further purification.

Intermediate 16A

4-Amino-5-bromopyrrolo[2,1-f][1,2,4]triazine-7-carbaldehyde

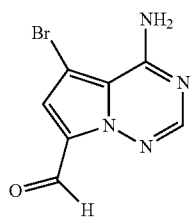 [SMILES: Nc1ncnn2c(C=O)cc(Br)c12]

Intermediate 15A (20.6 g, 127 mmol) was dissolved in 525 mL DMF. At 0° C., 1,3-dibromo-5,5-dimethylhydantoin (21.8 g, 76.2 mmol) was added, and the mixture was stirred for 1 h under ice cooling and for further 2 h at room temperature. The resulting suspension was filtered, and the residue was washed with DMF and diethyl ether. The filtrate was discarded, and the remaining hardly soluble crystals were dried to give 20.0 g (65% of th., 80% purity by HPLC) of the title compound. This material was used without further purification.

$^1$H NMR (400 MHz, $d_6$-DMSO): δ (ppm)=7.42 (s, 1H), 8.12 (s, 1H), 10.22 (s, 1H).

Intermediate 17A (4-Amino-5-bromopyrrolo[2,1-f][1,2,4]triazin-7-yl)(cyclopropyl)methanol

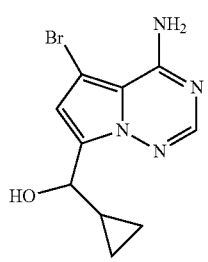 [SMILES: Nc1ncnn2c(C(O)C3CC3)cc(Br)c12]

Intermediate 16A (500 mg, 1.66 mmol) was suspended in dry THF (30 mL). At 0° C., a 0.5 M solution of cyclopropyl magnesium bromide in diethyl ether (10 mL, 5.0 mmol) was added. The mixture was stirred at room temperature for 1 h. Then, another portion of the Grignard solution (6.6 mL, 3.3 mmol) was added. After further stirring for 30 min at room temperature, the reaction was quenched with saturated aqueous ammonium chloride solution and extracted with ethyl acetate (2×20 mL). The combined organic layers were washed with brine, dried over magnesium sulfate and concentrated. The residue was purified by preparative HPLC (method 4). Yield: 0.14 g (29% of th.).

LC-MS (method 6): $R_t$=0.75 min; MS (ESIpos): m/z (%)=283.0 (100) [M+H]$^+$.

$^1$H NMR (400 MHz, d$_6$-DMSO): δ (ppm)=0.35 (m, 3H), 0.45 (m, 1.28 (m, 4.62 (t, 1H), 5.26 (d, 1H), 6.75 (s, 1H), 7.84 (s, 1H).

Intermediate 18A (4-Amino-5-bromopyrrolo[2,1-f][1,2,4]triazin-7-yl)(tetrahydro-2H-pyran-4-yl)methanol

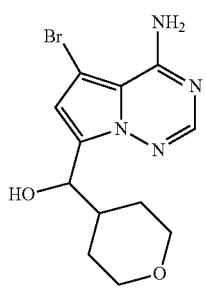 [SMILES: Nc1ncnn2c(C(O)C3CCOCC3)cc(Br)c12]

In a 50 mL three-necked flask equipped with a condenser, a thermometer and a dropping funnel, which was purged with argon, a Grignard reagent was prepared from magnesium turnings (484 mg, 19.9 mmol) and 4-chlorotetrahydropyrane (2.4 g, 19.9 mmol) in dry THF (14 mL). To this solution was added at 0° C. a suspension of Intermediate 16A (1.2 g, 3.98 mmol) in THF (20 mL), and the reaction mixture was allowed to stir for 1 h at room temperature. It was then quenched with saturated aqueous ammonium chloride solution and extracted with ethyl acetate (2×50 mL). The organic layer was washed with brine, dried over magnesium sulfate and concentrated. The residue was purified by preparative HPLC (method 3). Yield: 0.5 g (38% of th.).

LC-MS (method 6): $R_t$=0.66 min; MS (ESIpos): m/z (%)=327.0 (100) [M+H]$^+$, MS (ESIneg): m/z (%)=325.1 (100) [M–H]$^-$.

Intermediate 19A 8-(4-Aminopyrrolo[2,1-f][1,2,4]triazin-7-yl)-1,4-dioxaspiro[4.5]decan-8-ol

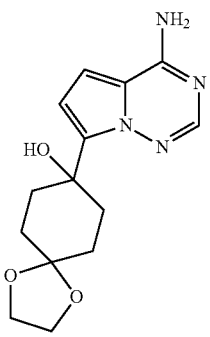 [SMILES: Nc1ncnn2c(C3(O)CCC4(CC3)OCCO4)ccc12]

The starting material 7-bromopyrrolo[2,1-f][1,2,4]triazin-4-amine was synthesized according to the procedure described in WO 2007/056170-A2 (Intermediate B).

7-Bromopyrrolo[2,1-f][1,2,4]triazin-4-amine (9.20 g, 35.41 mmol) was dissolved in THF (105 mL) under argon at room temperature. Chlorotrimethylsilane (9.08 mL, 7.77 g, 70.82 mmol, 2 eq.) was added, and the mixture was stirred at room temperature for 3 h. It was then cooled to 0° C., and 2-propyl magnesium chloride (74 mL of a 2.0 M solution in THF, 149 mmol, 4.2 eq.) was added. The mixture was stirred for further 3 h while warming up to room temperature. Then, 1,4-dioxaspiro[4.5]decan-8-one (8.38 g, 53.12 mmol, 1.5 eq.) was added, and stirring was continued for another 16 h. The reaction was quenched with a 1:1 mixture of concentrated aqueous ammonium chloride solution and ice until the pH value reached 6-7. The mixture was extracted with two portions of ethyl acetate, and the combined organic extracts were dried over anhydrous sodium carbonate and concentrated to dryness. The title compound was crystallized from diethyl ether. Yield: 6.05 g (58% of th.).

HPLC (method 1): $R_t$=2.89 min;

LC-MS (method 6): $R_t$=0.38 min; MS (ESIpos): m/z (%)=291.2 (100) [M+H]$^+$, MS (ESIneg): m/z (%)=289.4 (100) [M−H]$^−$.

Intermediate 20A 7-(1,4-Dioxaspiro[4.5]dec-7-en-8-yl)pyrrolo[2,1-f][1,2,4]triazin-4-amine

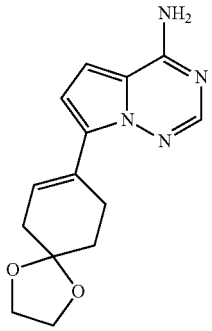 [SMILES: Nc1ncnn2c(C3=CCC4(CC3)OCCO4)ccc12]

Intermediate 19A (2.81 g, 60% purity, 5.82 mmol) was dissolved in pyridine (18 mL) at 0° C. Trifluoroacetic anhydride (2.46 mL, 3.66 g, 17.45 mmol, 3 eq.) was added slowly, and the reaction mixture was stirred at ambient temperature for 16 h. The solvent was distilled off, and the residue was partitioned between water and ethyl acetate. The organic extract was dried over sodium sulfate and evaporated. The residue was triturated with diethyl ether at 0° C. to yield 2.95 g (92% pure by HPLC, 99% of th.) of the title compound.

HPLC (method 1): $R_t$=4.55 min;

LC-MS (method 5): $R_t$=2.28 min; MS (ESIpos): m/z (%)=369.1 (100) [M+H]$^+$, MS (ESIneg): m/z (%)=367.1 (100) [M−H]$^−$.

Intermediate 21A 7-(1,4-Dioxaspiro[4.5]dec-8-yl)pyrrolo[2,1-f][1,2,4]triazin-4-amine

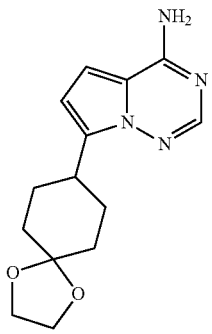 [SMILES: Nc1ncnn2c(C3CCC4(CC3)OCCO4)ccc12]

Intermediate 20A (2.95 g, 10.8 mmol) was dissolved in methanol (1.07 L) under argon. Palladium on charcoal (10%, 400 mg) was added, and the mixture was vigorously stirred for 24 h under an atmosphere of hydrogen at ambient pressure and room temperature. The catalyst was removed by filtration, and the solvent was distilled off under reduced pressure to give 2.11 g (71% of th.) of the title compound.

HPLC (method 1): $R_t$=3.14 min;

LC-MS (method 6): $R_t$=0.68 min; MS (ESIpos): m/z (%)=275.3 (100) [M+H]$^+$.

Intermediate 22A 4-(4-Aminopyrrolo[2,1-f][1,2,4]triazin-7-yl)cyclohexanone

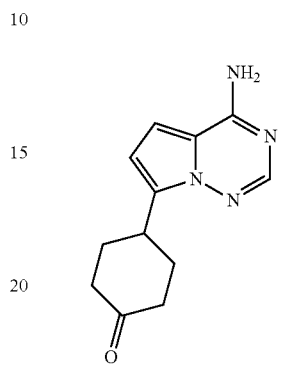

Intermediate 21A (2.11 g, 7.69 mmol) was dissolved in a mixture of 1 M hydrochloric acid (23 mL) and methanol (6.80 mL) at 0° C. and stirred under ice cooling for 3 h. Then, the pH value was adjusted to 6-7 by addition of concentrated aqueous sodium bicarbonate solution. The mixture was extracted with three portions of dichloromethane, and the combined organic extracts were dried over anhydrous sodium sulfate, filtered and evaporated. The residue (923 mg, 52% of th.) was used without further purification in the next synthetic step.

HPLC (method 2): $R_t$=3.06 min;

LC-MS (method 4): $R_t$=1.02 min; MS (ESIpos): m/z (%)=231.1 (100) [M+H]$^+$, MS (ESIneg): m/z (%)=229.2 (100) [M−H]$^−$.

$^1$H NMR (400 MHz, $d_6$-DMSO): δ (ppm)=1.86 (ddd, 2H), 2.25-2.36 (m, 4H), 2.59 (ddd, 2H), 3.59 (m, 1H), 6.45 (d, 1H), 6.82 (d, 1H), 7.60 (br. s, 1H), 7.82 (s, 1H).

Intermediate 23A trans-4-(4-Aminopyrrolo[2,1-f][1,2,4]triazin-7-yl)cyclohexanol

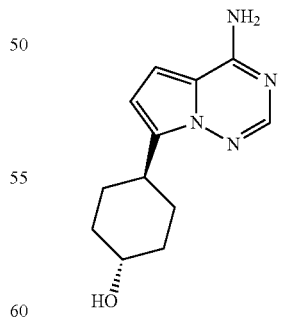

Intermediate 22A (452 mg, 1.96 mmol) was dissolved in THF (15 mL), and the solution was cooled to 0° C. Lithium aluminium hydride solution (1 M in THF, 2.94 mL, 2.94 mmol) was added dropwise. Subsequently, the solution was stirred at 0° C. for 10 min and then quenched by addition of concentrated aqueous ammonium chloride solution. The mixture was extracted with 3 portions of dichloromethane, and the combined organic extracts were dried over anhydrous sodium sulfate, filtered and evaporated. The residue (360 mg, 77% purity, 61% of th.) was used in the next synthetic step without further purification.

HPLC (method 1): $R_t$=2.62 min;

LC-MS (method 6): $R_t$=0.29 min; MS (ESIpos): m/z (%)=233.2 (100) [M+H]$^+$.

$^1$H NMR (400 MHz, $d_6$-DMSO): δ (ppm)=1.30 (m, 2H), 1.42 (m, 2H), 1.91 (m, 2H), 1.99 (m, 2H), 2.97 (tt, 1H), 3.45 (m, 1H), 4.60 (d, 1H), 6.39 (d, 1H), 6.79 (d, 1H), 7.53 (br. s, 2H), 7.80 (s, 1H).

Intermediate 24A trans-4-(4-Amino-5-bromopyrrolo[2,1-f][1,2,4]tri-azin-7-yl)cyclohexanol

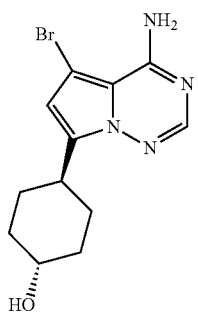 [SMILES: Nc1ncnn2c1c(Br)cc2[C@H]1CC[C@H](O)CC1]

Intermediate 23A (360 mg, 85% purity, 1.19 mmol) was dissolved in THF (8 mL) at −20° C., and 1,3-dibromo-5,5-dimethylhydantoin (188 mg, 0.66 mmol, 0.55 eq.) was added. The mixture was stirred at −20° C. for 1 h, then 0.5 mL concentrated aqueous sodium dithionite solution was added, and the mixture was extracted with ethyl acetate. The organic extract was dried over anhydrous sodium sulfate, filtered and evaporated. The crude product (463 mg, 66% purity, 83% of th.) was used in the next synthetic step without further purification.

HPLC (method 1): $R_t$=3.22 min;

LC-MS (method 7): $R_t$=1.03 min; MS (ESIpos): m/z (%)=311.2 and 313.0 (100) [M+H]$^+$, MS (ESIneg): m/z (%)=309.2 (50) and 311.2 (40) [M−H]$^-$.

Intermediate 25A tert-Butyl 3-(4-aminopyrrolo[2,1-f][1,2,4]triazin-7-yl)-3-hydroxypiperidine-1-carboxylate

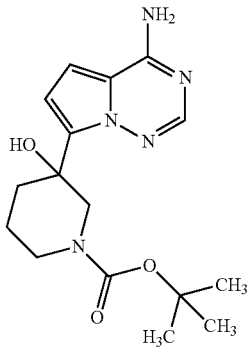 [SMILES: CC(C)(C)OC(=O)N1CCCC(O)(c2ccc3c(N)ncnn23)C1]

The starting material 7-bromopyrrolo[2,1-f][1,2,4]triazin-4-amine was synthesized according to the procedure described in WO 2007/056170-A2 (Intermediate B).

7-Bromopyrrolo[2,1-f][1,2,4]triazin-4-amine (17.29 g, 81 mmol) was dissolved in THF (214 mL) under argon at room temperature. Chlorotrimethylsilane (20.60 mL, 17.63 g, 162 mmol, 2 eq.) was added, and the mixture was stirred at room temperature for 3 h. Then, it was cooled to 0° C., and 2-propyl magnesium chloride (170 mL of a 2.0 M solution in THF, 340 mmol, 4.2 eq.) was added. The mixture was stirred for further 3 h while warming up to room temperature. Then, tert-butyl 3-oxopiperidine-1-carboxylate (25.00 g, 121 mmol, 1.5 eq.) was added, and stirring was continued for another 16 h. The reaction was quenched with a 1:1 mixture of concentrated aqueous ammonium chloride solution and ice until the pH value reached 6-7. The mixture was extracted with two portions of ethyl acetate, and the combined organic extracts were dried over anhydrous sodium carbonate and concentrated to dryness. The title compound crystallized upon trituration of the residue with diethyl ether (50 mL). The crystals were washed with diethyl ether and dried to give 17.20 g (64% of th.).

HPLC (method 2): $R_t$=3.53 min;

LC-MS (method 5): $R_t$=1.36 min; MS (ESIpos): m/z (%)=334.1 (100) [M+H]$^+$, MS (ESIneg): m/z (%)=332.0 (100) [M−H]$^-$.

¹H NMR (400 MHz, d₆-DMSO): δ (ppm)=1.19-1.43 (m, 9H), 1.72-1.88 (m, 2H), 2.38-2.46 (m, 1H), 3.02-3.20 (m, 1H), 3.44-3.96 (m, 4H), 6.58 (d, 1H), 6.81 (d, 1H), 7.82 (s, 1H).

Intermediate 26A rac-tert-Butyl 3-(4-amino-5-bromopyrrolo[2,1-f][1,2,4]triazin-7-yl)-3-hydroxypiperidine-1-carboxylate

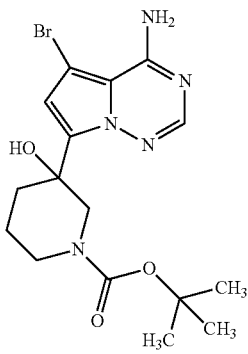 [SMILES: CC(C)(C)OC(=O)N1CCCC(O)(c2cc(Br)c3c(N)ncnn23)C1]

Intermediate 25A (120 mg, 0.36 mmol) was dissolved in THF (6.0 mL) at −20° C., and 1,3-dibromo-5,5-dimethylhydantoin (51 mg, 0.18 mmol, 0.5 eq.) was added. The mixture was stirred at −20° C. for 2 h and then quenched with concentrated aqueous sodium sulfite solution (0.5 mL). Ethyl acetate was added, the aqueous layer was separated, and the organic extract was dried over sodium sulfate and evaporated. The title compound (148 mg, 95% of th.) was obtained as a light yellow solid.

HPLC (method 1): R_t=4.03 min;

LC-MS (method 5): R_t=1.99 min; MS (ESIpos): m/z (%)=412.0 (90) and 414.0 (100) [M+H]⁻, MS (ESIneg): m/z (%)=410.0 (100) and 412.0 (85) [M−H]⁺.

Intermediate 27A tert-Butyl 5-[4-[(trifluoroacetyl)amino]pyrrolo[2,1-f][1,2,4]triazin-7-yl]-3,6-dihydropyridine-1(2H)-carboxylate

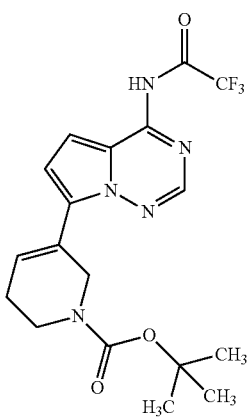 [SMILES: CC(C)(C)OC(=O)N1CCC=C(c2ccc3c(NC(=O)C(F)(F)F)ncnn23)C1]

Intermediate 25A (8.32 g, 24.95 mmol) was dissolved in pyridine (116 mL) at 0° C. Trifluoroacetic anhydride (8.81 mL, 13.10 g, 62.36 mmol, 2.5 eq.) was added slowly, and the reaction mixture was stirred at ambient temperature for 16 h. Then, it was cooled again to 0° C., and 150 mL of diethyl ether were added. The mixture was stirred at 0° C. while the title compound slowly precipitated. The product was finally filtered off and washed with diethyl ether. The filtrate was evaporated in vacuo, and the residue was triturated with diethyl ether at 0° C. giving a second crop of the title compound after washing with diethyl ether. The two crops were combined to yield 7.80 g (92% pure by HPLC, 76% of th.) of the title compound as yellow crystals.

HPLC (method 1): R_t=3.91 min;

LC-MS (method 7): R_t=2.45 min; MS (ESIpos): m/z (%)=412.2 (100) [M+H]⁺, MS (ESIneg): m/z (%)=410.2 (100) [M−H]⁻.

¹H NMR (400 MHz, d₆-DMSO): δ (ppm)=1.48 (s, 9H), 1.92 (m, 2H), 3.58 (m, 2H), 6.90 (d, 1H), 7.30 (d, 1H), 8.03-8.10 (m, 1H), 8.42 (s, 1H).

Intermediate 28A rac-tert-Butyl 3-(4-aminopyrrolo[2,1-f][1,2,4]triazin-7-yl)piperidine-1-carboxylate

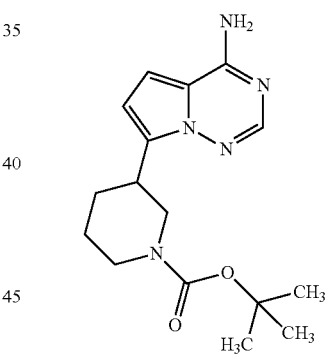

Intermediate 27A (7.80 g, 92% purity, 17.54 mmol) was dissolved in methanol (400 mL). Trifluoroacetic acid (6.76 mL, 10.0 g, 88 mmol, 5 eq.), water (3.16 mL, 175 mmol, 10 eq.) and 10% palladium on charcoal (30 mg) were added, and the mixture was hydrogenated for 24 h at room temperature and ambient pressure. The catalyst was then removed by filtration, and the solvent was evaporated in vacuo. The crude product (8.79 g, 75% pure, quantitative yield) was used in the next synthetic step without further purification.

HPLC (method 1): R_t=3.64 min;

LC-MS (method 7): R_t=1.26 min; MS (ESIpos): m/z (%)=318.3 (100) [M+H]⁺, MS (ESIneg): m/z (%)=316.4 (100) [M−H]⁻.

Intermediate 29A

7-[(3R)-Piperidin-3-yl]pyrrolo[2,1-f][1,2,4]triazin-4-amine trifluoroacetate

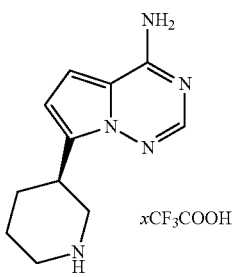 [SMILES: Nc1ncnn2c([C@@H]3CCCNC3)ccc12]

The starting material benzyl (R)-3-(4-amino-5-bromopyrrolo[2,1-f][1,2,4]triazin-7-yl)piperidine-1-carboxylate has been described in WO 2007/056170-A2 (Intermediate DDD).

1.50 g (3.49 mmol) of this material were hydrogenated for 16 h at room temperature and ambient pressure in the presence of 10% palladium on charcoal (30 mg) in a mixture of methanol (50 mL) and trifluoroacetic acid (2.70 mL). Subsequently, the catalyst was removed by filtration, and all volatiles were evaporated in vacuo to give 1.10 g (95% of th.) of the title compound.

HPLC (method 2): $R_t$=2.17 min;
LC-MS (method 6): $R_t$=0.17 min; MS (ESIpos): m/z (%)=218 (100) [M+11]$^+$.
$^1$H NMR (400 MHz, $d_6$-DMSO): δ (ppm)=1.75 (m, 2H), 1.92 (m, 1H), 2.05 (m, 1H), 2.93 (m, 1H), 3.06 (m, 1H), 3.31 (d, 1H), 3.50 (d, 1H), 3.57 (m, 1H), 6.78 (d, 1H), 7.20 (m, 1H), 8.10 (s, 1H), 8.63 (m, 1H), 8.82 (m, 1H), 9.02 (br. s, 1H).

Intermediate 30A tert-Butyl (3R)-3-(4-aminopyrrolo[2,1-f][1,2,4]triazin-7-yl)piperidine-1-carboxylate

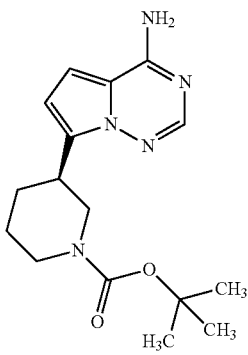 [SMILES: CC(C)(C)OC(=O)N1CCC[C@@H](c2ccc3c(N)ncnn23)C1]

Intermediate 29A (1.10 g, 5.06 mmol) was suspended in dichloromethane (6.60 mL), triethylamine (1.55 mL, 1.13 g, 11.14 mmol, 2.20 eq.) was added, and the mixture was stirred for 30 min until the starting material was completely dissolved. Then, di-tert-butyl dicarbonate (1.22 g, 5.57 mmol, 1.1 eq.) was added, and the reaction mixture was stirred for 16 h. Subsequently, 5% aqueous citric acid was added, the phases were separated, and the organic layer was dried over sodium sulfate and evaporated. The residue was purified by preparative HPLC (method 2). Yield: 595 mg (37% of th.).

HPLC (method 2): $R_t$=4.01 min;
LC-MS (method 5): $R_t$=1.54 min; MS (ESIpos): m/z (%)=318.1 (100) [M+H]$^+$, MS (ESIneg): m/z (%)=316.1 (100) [M−H]$^−$.
$^1$H NMR (400 MHz, $d_6$-DMSO): δ (ppm)=1.38 (s, 9H), 1.45 (m, 2H), 1.72 (m, 2H), 2.02 (m, 2H), 2.90 (m, 1H), 3.17 (m, 1H), 3.85 (m, 1H), 4.08 (m, 1H), 6.47 (d, 1H), 6.80 (d, 1H), 7.58 (br. s, 1H), 7.81 (s, 1H).

Intermediate 31A rac-tert-Butyl 3-(4-amino-5-bromopyrrolo[2,1-f][1,2,4]triazin-7-yl)piperidine-1-carboxylate

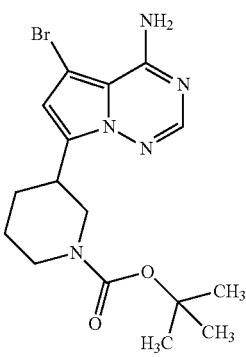 [SMILES: CC(C)(C)OC(=O)N1CCCC(c2cc(Br)c3c(N)ncnn23)C1]

Intermediate 28A (8.28 g, 75% purity, 14.39 mmol) was dissolved in THF (222 mL) at −20° C., and 1,3-dibromo-5,5-dimethylhydantoin (2.06 g, 7.19 mmol, 0.5 eq.) was added. The mixture was stirred at −20° C. for 2 h and then quenched with concentrated aqueous sodium sulfite solution (0.5 mL). Ethyl acetate was added, the aqueous layer was separated, and the organic extract was dried over sodium sulfate and evaporated. The title compound (6.30 g, 86% of th.) was obtained as a light yellow solid.

LC-MS (method 5): $R_t$=2.27 min; MS (ESIpos): m/z (%)=396.0 (80) and 397.9 (100) [M+H]$^−$, MS (ESIneg): m/z (%)=394.0 (90) and 396.0 (100) [M−H]$^−$.

¹H NMR (400 MHz, d₆-DMSO): δ (ppm)=1.35 (s, 9H), 1.40-1.44 (m, 2H), 1.71 (m, 1H), 1.98 (m, 1H), 2.95 (m, 1H), 3.20 (m, 1H), 3.75 (m, 1H), 4.00 (m, 1H), 6.67 (s, 1H), 7.86 (s, 1H).

Intermediate 32A tert-Butyl (3R)-3-(4-amino-5-bromopyrrolo[2,1-f][1,2,4]triazin-7-yl)piperidine-1-carboxylate

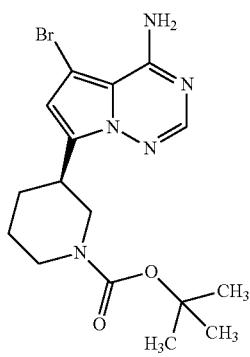 [SMILES: CC(C)(C)OC(=O)N1CCC[C@@H](c2cc(Br)c3c(N)ncnn23)C1]

The title compound was prepared in the same way as the racemic mixture (Intermediate 31A), starting from Intermediate 30A. Analytical data were identical to those shown for Intermediate 31A.

Intermediate 33A 1-(4-Amino-5-bromopyrrolo[2,1-f][1,2,4]triazin-7-yl)-2-chloroethanone

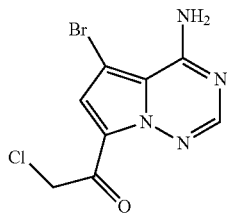 [SMILES: Nc1ncnn2c(C(=O)CCl)cc(Br)c12]

The compound was prepared according to the procedure described in WO 2007/056170-A2 (Intermediate N, step 1).

HPLC (method 1): $R_t$=4.27 min;

LC-MS (method 5): $R_t$=1.70 min; MS (ESIpos): m/z (%)=289.0 (75) and 290.9 (100) [M+H]⁺, MS (ESIneg): m/z (%)=287.0 (75) and 288.9 (100) [M−H]⁻.

Intermediate 34A

5-Bromo-7-(2-methyl-1,3-thiazol-4-yl)pyrrolo[2,1-f][1,2,4]triazin-4-amine

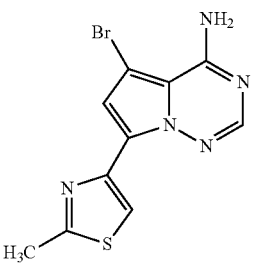 [SMILES: Cc1nc(-c2cc(Br)c3c(N)ncnn23)cs1]

Intermediate 33A (100 mg, 0.35 mmol) and thioacetamide (30 mg, 0.40 mmol, 1.15 eq.) were dissolved in 1,4-dioxane (3.0 mL) in a microwave reaction vial. The vial was crimp-capped, and the mixture was heated to 130° C. for 60 min in a single-mode microwave device. After cooling, the solvent was distilled off, and the residue was triturated with acetonitrile and filtered. The filtrate was discarded. The title compound was isolated as crystalline solid. Yield: 99 mg (92% of th.).

HPLC (method 1): $R_t$=4.00 min;

LC-MS (method 6): $R_t$=1.05 min; MS (ESIpos): m/z (%)=310.0 (90) and 312 (100) [M+H]⁺.

¹H NMR (400 MHz, d₆-DMSO): δ (ppm)=2.71 (s, 3H), 7.20 (s, 1H), 8.02 (s, 1H), 8.28 (s, 1H).

Intermediate 35A

5-Bromo-7-(2-ethyl-1,3-thiazol-4-yl)pyrrolo[2,1-f][1,2,4]triazin-4-amine

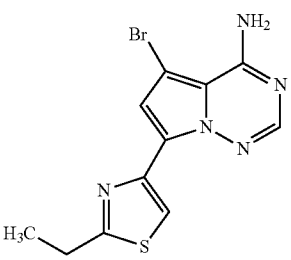 [SMILES: CCc1nc(-c2cc(Br)c3c(N)ncnn23)cs1]

Intermediate 33A (100 mg, 0.35 mmol) and thiopropionamide (32 mg, 0.36 mmol, 1.05 eq.) were refluxed in ethanol (3.0 mL) over a period of 4.5 h. After cooling, the mixture was partitioned between ethyl acetate and aqueous sodium bicarbonate solution. The organic layer was dried over anhydrous sodium sulfate, and the solvent was distilled off. The product was dried under vacuum to give 91 mg (0.28 mmol, 81% of th.) of the title compound as off-white solid.

HPLC (method 1): $R_t$=4.30 min;

LC-MS (method 7): $R_t$=1.84 min; MS (ESIpos): m/z (%)=324.2 (100) and 325.8 (98) [M+H]⁺.

Intermediate 36A

7-(2-Amino-1,3-thiazol-4-yl)-5-bromopyrrolo[2,1-f][1,2,4]triazin-4-amine

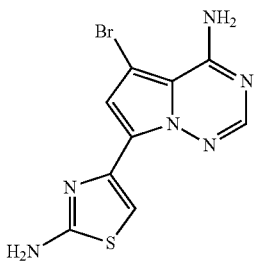 [SMILES: Nc1nc(-c2cc(Br)c3c(N)ncnn23)cs1]

Intermediate 33A (100 mg, 0.35 mmol) and thiourea (32 mg, 0.41 mmol, 1.2 eq.) were suspended in 1,4-dioxane (3 mL) in a microwave reaction vial which was then crimp-capped. The mixture was heated to 120° C. for 60 min in a single-mode microwave device. Upon cooling, water was added, and the resulting precipitate was collected by filtration and washed with dioxane. The off-white solid was dried under vacuum to give 98 mg (91% of th.) of the title compound.

HPLC (method 1): $R_t$=3.19 min;

LC-MS (method 5): $R_t$=1.25 min; MS (ESIpos): m/z (%)=310.9 (95) and 312.9 (100) [M+H]$^+$, MS (ESIneg): m/z (%)=309.0 (100) and 310.9 (70) [M−H]$^−$.

$^1$H NMR (400 MHz, d$_6$-DMSO): δ (ppm)=7.17 (s, 1H), 7.52 (s, 1H), 8.07 (s, 1H).

Intermediate 37A

1-{4-[(4-Amino-5-bromopyrrolo[2,1-f][1,2,4]triazin-7-yl)methyl]piperazin-1-yl}-2,2,2-trifluoroethanone

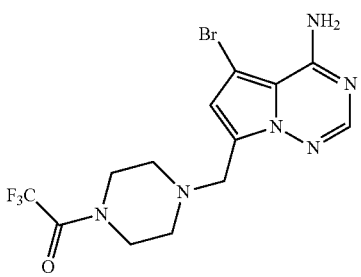 [SMILES: Nc1ncnn2c(CN3CCN(C(=O)C(F)(F)F)CC3)cc(Br)c12]

The compound was prepared according to the procedure described in WO 2007/056170-A2 (Example 416, step 6).

Intermediate 38A

5-Bromo-7-(morpholin-4-ylmethyl)pyrrolo[2,1-f][1,2,4]triazin-4-amine

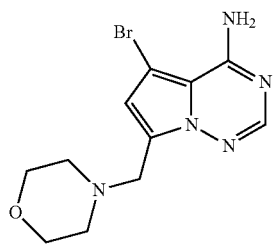 [SMILES: Nc1ncnn2c(CN3CCOCC3)cc(Br)c12]

The compound was prepared according to the procedure described in WO 2007/064931-A2 (Intermediate C).

Intermediate 39A

7-(Morpholin-4-ylmethyl)-5-(4,4,5,5-tetramethyl-1,3,2-dioxaborolan-2-yl)pyrrolo[2,1-f][1,2,4]-triazin-4-amine

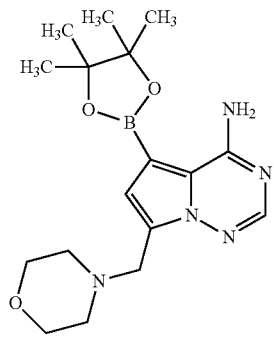 [SMILES: CC1(C)OB(c2cc(CN3CCOCC3)n3ncnc(N)c23)OC1(C)C]

To a solution of Intermediate 38A (5.59 g, 17.9 mmol) and bis(pinacolato)diboron (10.0 g, 39.4 mmol) in degassed DMF (120 mL) was added under an argon atmosphere 1,1'-bis(diphenylphosphino)ferrocene-palladium(II) chloride (786 mg, 1.07 mmol) and potassium acetate (7.03 g, 71.6 mmol). The mixture was heated to 80° C. for 5 h and then cooled to room temperature. tert-Butyl methyl ether (100 mL) was added, and the suspension was filtered. The filtrate was evaporated to dryness under reduced pressure, and the residue was purified by flash chromatography over silica gel (gradient elution from 2% to 5% methanol in dichloromethane) to give 1.30 g (20% of th.) of the title compound containing some of the corresponding boronic acid derivative. This product was used without further purification.

LC-MS (method 6): $R_t$=0.73 min; MS (ESIpos): m/z (%)=360.3 (30) [M+H]⁺.

Intermediate 40A

5-[4-({[tert-Butyl(dimethyl)silyl]oxy}methyl)-3,5-difluorophenyl]-7-(morpholin-4-ylmethyl)pyrrolo[2,1-f][1,2,4]triazin-4-amine

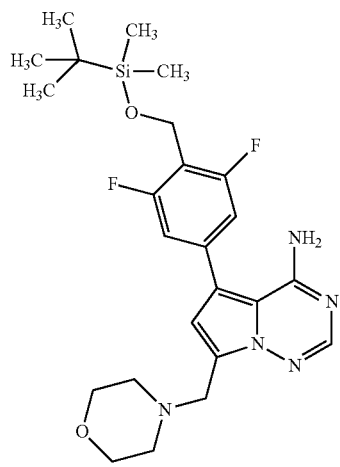 [SMILES: CC(C)(C)[Si](C)(C)OCc1c(F)cc(-c2cc(CN3CCOCC3)n3ncnc(N)c23)cc1F]

The title compound was obtained by general synthetic method 1 from Intermediate 38A (200 mg, 0.64 mmol) and [4-({[tert-butyl(dimethyl)silyl]oxy}methyl)-3,5-difluorophenyl]boronic acid (314 mg, 0.77 mmol, 74% purity; prepared by the method of Hattori, *Bioorg. Med. Chem.* 2006, 14, 3258-3262). Purification of the crude product was carried out by preparative HPLC (method 3). Yield: 110 mg (32% of th., LC-MS purity 92%).

LC-MS (method 6): $R_t$=1.18 min; MS (ESIpos): m/z (%)=490.1 (30) [M+H]⁺, MS (ESIneg): m/z (%)=488.3 (100) [M-H]⁻.

Intermediate 41A

Methyl 4-[4-amino-7-(morpholin-4-ylmethyl)pyrrolo[2,1-f][1,2,4]triazin-5-yl]-2-fluorobenzoate

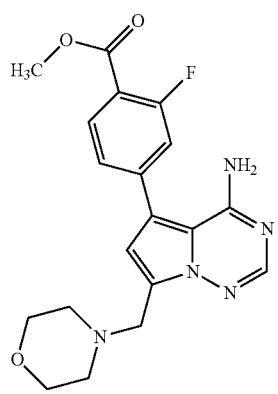 [SMILES: COC(=O)c1ccc(-c2cc(CN3CCOCC3)n3ncnc(N)c23)cc1F]

The title compound was obtained by general synthetic method 1 from Intermediate 38A (200 mg, 0.64 mmol) and [3-fluoro-4-(methoxycarbonyl)phenyl]boronic acid (139 mg, 0.71 mmol). Purification of the crude product was carried out by preparative HPLC (method 3). Yield: 80 mg (32% of th.).

LC-MS (method 6): $R_t$=0.66 min; MS (ESIpos): m/z (%)=386.1 (80) [M+H]⁺.

Intermediate 42A

4-[4-Amino-7-morpholin-4-ylmethyl)pyrrolo[2,1-f][1,2,4]triazin-5-yl]benzaldehyde

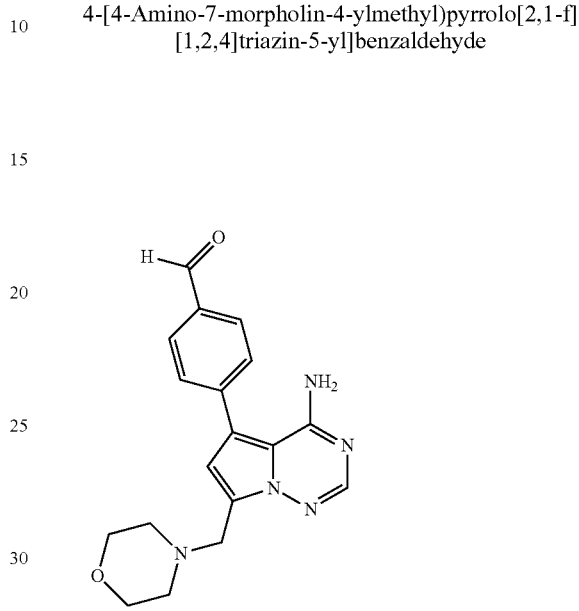

To a solution of Intermediate 38A (300 mg, 0.96 mmol) in degassed DMF (9.0 mL) was added (4-formylphenyl)boronic acid (216 mg, 1.44 mmol), tetrakis(triphenylphosphine)palladium(0) (111 mg, 0.1 mmol) and 2 M aqueous sodium carbonate solution (2.4 mL). The mixture was heated to 90° C. under argon for 17 h, then cooled to room temperature and directly purified by preparative HPLC (method 3). Yield: 150 mg (46% of th.).

LC-MS (method 6): $R_t$=0.44 min; MS (ESIpos): m/z (%)=338.2 (30) [M+H]⁺.

Intermediate 43A

5-Bromo-6-methyl-7-(morpholin-4-ylmethyl)pyrrolo[2,1-f][1,2,4]triazin-4-amine

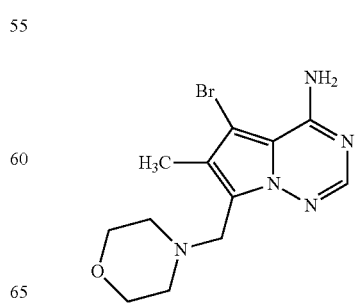

The compound was prepared according to the procedure described in WO 2007/056170-A2 (Intermediate O).

Intermediate 44A

1-[(4-Aminopyrrolo[2,1-f][1,2,4]triazin-7-yl)methyl]piperidin-4-ol

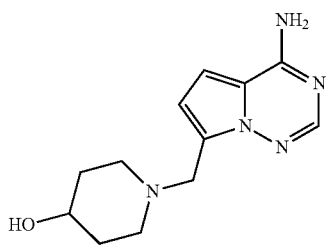 [SMILES: Nc1ncnn2c(CN3CCC(O)CC3)ccc12]

4-Hydroxypiperidine (3.62 g, 35.8 mmol) and 37% formalin solution (2.9 g, 35.8 mmol) were dissolved in acetic acid (150 mL) and stirred at room temperature for 1 h. To this solution was added a solution of pyrrolo[2,1-f][1,2,4]triazin-4-amine (2.0 g, 14.9 mmol; prepared according to the procedure described in WO 2007/056170-A2, Intermediate A) in acetic acid (150 mL), and the mixture was stirred at 60° C. for 2 h. The solvent was then evaporated, and the residue was taken up in 200 mL of half-concentrated aqueous potassium bicarbonate solution and extracted with 200 mL dichloromethane. The organic layer was washed with water (2×50 mL) and discarded. The combined aqueous layers were evaporated to dryness, and the residue was treated with a 10:1 mixture of dichloromethane and methanol (2×100 mL). The organic extracts were evaporated, and the residue was purified by preparative HPLC (method 4) to give 1.16 g (15% of th.) of the title compound.

LC-MS (method 7): $R_t$=0.18 min; MS (ESIpos): m/z (%)=248.3 (30) [M+H]$^+$, MS (ESIneg): m/z (%)=246.5 (100) [M−H]$^−$.

$^1$H NMR (400 MHz, $d_6$-DMSO): δ (ppm)=1.35 (br. m, 2H), 1.67 (br. m, 2H), 2.07 (t, 2H), 2.70 (hr. m, 2H), 3.38 (br. m, 1H), 3.75 (s, 2H), 4.51 (br, 1H), 6.52 (d, 1H), 6.84 (d, 1H), 7.62 (br, 2H), 7.82 (s, 1H).

Intermediate 45A

1-[(4-Amino-5-bromopyrrolo[2,1-f][1,2,4]triazin-7-yl)methyl]piperidin-4-ol

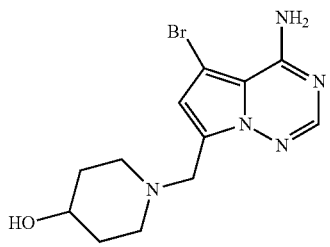 [SMILES: Nc1ncnn2c(CN3CCC(O)CC3)cc(Br)c12]

Intermediate 44A (1.10 g, 4.45 mmol) was dissolved in DMF (16.5 mL) and cooled to −20° C. 1,3-Dibromo-5,5-dimethylhydantoin (636 mg, 2.22 mmol) was added every 10 min in about 100 mg portions. Subsequently, the mixture was stirred at room temperature for a further hour and was then directly purified by preparative HPLC (method 4). Yield: 0.61 g (42% of th.).

LC-MS (method 4): $R_t$=0.75 min; MS (ESIpos): m/z (%)=326.0 (30) [M+H]$^+$, MS (ESIneg): m/z (%)=324.0 (100) [M−H]$^−$.

$^1$H NMR (400 MHz, $d_6$-DMSO): δ (ppm)=1.35 (br. m, 2H), 1.67 (br. m, 2H), 2.08 (t, 2H), 2.68 (br. m, 2H), 3.39 (br. m, 1H), 3.74 (s, 2H), 4.51 (br, 1H), 6.69 (s, 1H), 7.86 (s, 1H).

Intermediate 46A

1-[(4-Aminopyrrolo[2,1-f][1,2,4]triazin-7-yl)methyl]pyrrolidin-3-ol

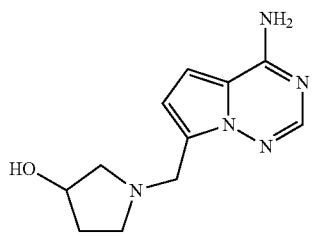 [SMILES: Nc1ncnn2c(CN3CCC(O)C3)ccc12]

3-Pyrrolidinol (1.56 g, 17.9 mmol) and 37% formalin solution (1.45 g, 17.9 mmol) were dissolved in acetic acid (75 mL) and stirred at room temperature for 10 min. To this solution was added a solution of pyrrolo[2,1-f][1,2,4]triazin-4-amine (2.0 g, 14.9 mmol) in acetic acid (75 mL), and the mixture was stirred at 60° C. for 4 h. After evaporation, the residue was taken up in 200 mL of 1 N aqueous potassium carbonate solution and extracted with ethyl acetate (3×200 mL). The combined organic layers were washed with brine, dried over magnesium sulfate and concentrated under reduced pressure. The residue was purified by preparative HPLC (method 4) to give 390 mg (11% of th.) of the title compound.

LC-MS (method 4): $R_t$=0.22 min; MS (ESIpos): m/z (%)=234.2 (20) [M+H]$^+$, MS (ESIneg): m/z (%)=223.0 (100) [M−H]$^−$.

$^1$H NMR (400 MHz, $d_6$-DMSO): δ (ppm)=1.50 (br. m, 1H), 1.94 (m, 1H), 2.34 (dd, 1H), 2.44 (dd, 1H), 2.60 (dd, 1H), 2.71 (dd, 1H), 3.84 (dd, 2H), 4.15 (br, 1H), 4.65 (d, 1H), 6.52 (d, 1H), 6.83 (d, 1H), 7.61 (br, 2H), 7.82 (s, 1H).

Intermediate 47A

1-[(4-Amino-5-bromopyrrolo[2,1-f][1,2,4]triazin-7-yl)methyl]pyrrolidin-3-ol

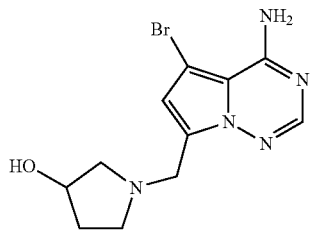 [SMILES: Nc1ncnn2c(CN3CCC(O)C3)cc(Br)c12]

Intermediate 46A (0.9 g, 3.86 mmol) was dissolved in DMF (14.2 mL) and cooled to −20° C. 1,3-Dibromo-5,5-dimethylhydantoin (606 mg, 2.12 mmol) was added every 10 min in about 100 mg portions, and stirring was continued at room temperature for 1 h. The mixture was partitioned between 10% aqueous potassium bicarbonate solution (50 mL) and ethyl acetate (100 mL). The aqueous layer was extracted with another portion of ethyl acetate (100 mL) and then with dichloromethane (100 mL). The combined organic layers were dried over magnesium sulfate and evaporated, and the residue was purified by preparative HPLC (method 4). Yield: 0.44 g (37% of th.).

LC-MS (method 6): $R_t$=0.21 min; MS (ESIpos): m/z (%)=314.0 (100) [M+H]$^+$.

$^1$H NMR (400 MHz, $d_6$-DMSO): δ (ppm)=1.50 (br. m, 1H), 1.95 (m, 1H), 2.34 (dd, 1H), 2.45 (m, 1H), 2.60 (m, 1H), 2.70 (dd, 1H), 3.84 (dd, 2H), 4.15 (br, 1H), 4.65 (d, 1H), 6.71 (s, 1H), 7.86 (s, 1H).

Intermediate 48A

1-[(4-Aminopyrrolo[2,1-f][1,2,4]triazin-7-yl)methyl]piperidin-3-ol

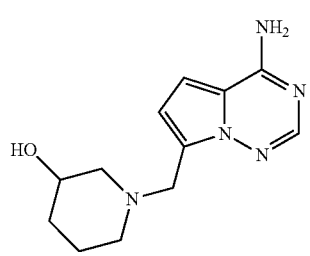 [SMILES: Nc1ncnn2c(CN3CCCC(O)C3)ccc12]

The title compound was prepared in analogy to Intermediate 46A with 3-hydroxypiperidine (1.80 g, 17.9 mmol) as starting material. After concentration of the reaction mixture, the residue was taken up in saturated aqueous potassium carbonate solution and extracted with 300 mL dichloromethane. The organic layer was washed with brine, dried over magnesium sulfate and concentrated under reduced pressure. The residue was purified by preparative HPLC (method 4) to give 650 mg (18% of th.) of the title compound.

LC-MS (method 6): $R_t$=0.16 min; MS (ESIpos): m/z (%)=248.2 (60) [M+H]$^+$.

$^1$H NMR (400 MHz, $d_6$-DMSO): δ (ppm)=0.99 (m, 1H), 1.37 (br. m, 1H), 1.57 (br. m, 1H), 1.74 (m, 2H), 1.88 (t, 1H), 2.68 (br. m, 1H), 2.83 (br. dd, 1H), 3.41 (br. m, 1H), 3.78 (dd, 2H), 4.54 (d, 1H), 6.52 (d, 1H), 6.84 (d, 1H), 7.61 (br, 2H), 7.82 (s, 1H).

Intermediate 49A

1-[(4-Amino-5-bromopyrrolo[2,1-f][1,2,4]triazin-7-yl)methyl]piperidin-3-ol

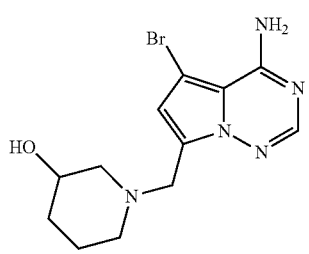 [SMILES: Nc1ncnn2c(CN3CCCC(O)C3)cc(Br)c12]

In analogy to the preparation of Intermediate 47A, the title compound was prepared from Intermediate 48A (690 mg, 179 mmol) to give 348 mg (93% LC-MS purity, 36% of th.) of the product after purification by preparative HPLC (method 4).

LC-MS (method 4): $R_t$=0.85 min; MS (ESIpos): m/z (%)=226.0 (100) [M+H]$^+$, MS (ESIneg): m/z (%)=223.9 (70) [M−H]$^−$.

$^1$H NMR (400 MHz, $d_6$-DMSO): δ (ppm)=0.99 (m, 1H), 1.37 (m, 1H), 1.57 (br. m, 1H), 1.74 (m, 2H), 1.89 (m, 1H), 2.66 (br. m, 1H), 2.81 (br. m, 1H), 3.41 (br. m, 1H), 3.77 (dd, 2H), 4.54 (d, 1H), 6.70 (s, 1H), 7.86 (s, 1H).

Intermediate 50A 1-({4-Amino-5-[4-({[tert-butyl(dimethyl)silyl]oxy}methyl)-3,5-difluorophenyl]pyrrolo[2,1-f]-[1,2,4]triazin-7-yl}methyl)piperidin-3-ol

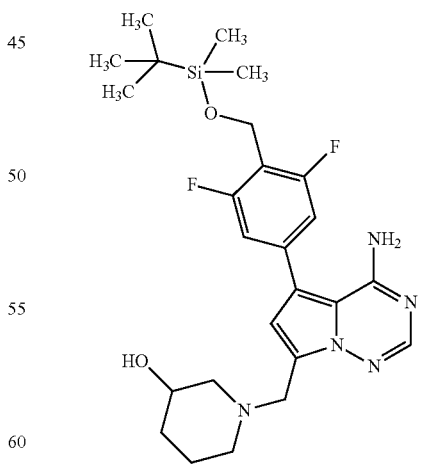

The title compound was obtained by general synthetic method 1 from Intermediate 49A (200 mg, 0.61 mmol) and [4-({[tert-butyl(dimethyl)silyl]oxy}methyl)-3,5-difluorophenyl]boronic acid (222 mg, 0.74 mmol; prepared by the method of Hattori, *Bioorg. Med. Chem.* 2006, 14, 3258-

3262). Purification of the crude product was carried out by preparative HPLC (method 3). Yield: 153 mg (50% of th.).

LC-MS (method 7): $R_t$=1.55 min; MS (ESIpos): m/z (%)=504.1 (100) [M+H]$^+$.

$^1$H NMR (400 MHz, $d_6$-DMSO): δ (ppm)=0.11 (s, 6H), 0.86 (s, 9H), 1.01 (m, 1H), 1.40 (br. m, 1H), 1.59 (br. m, 1H), 1.77 (m, 2H), 1.94 (m, 1H), 2.72 (br. m, 1H), 2.87 (br. m, 1H), 3.43 (m, 1H), 3.82 (dd, 2H), 4.55 (d, 1H), 4.74 (s, 2H), 6.75 (s, 1H), 7.18 (dd, 2H), 7.95 (s, 1H).

Intermediate 51A rac-tert-Butyl 3-{4-amino-5-[3,5-difluoro-4-(hydroxymethyl)phenyl]pyrrolo[2,1-f][1,2,4]triazin-7-yl}pyrrolidine-1-carboxylate

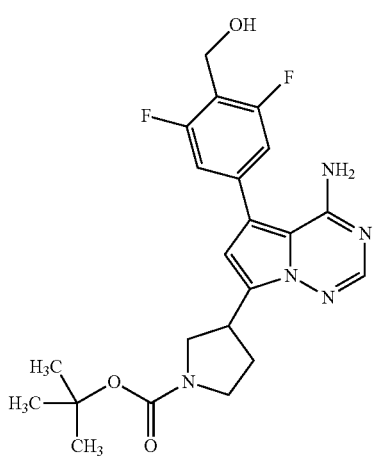 [SMILES: CC(C)(C)OC(=O)N1CCC(c2cc(-c3cc(F)c(CO)c(F)c3)c3c(N)ncnn23)C1]

The preparation of the starting material tert-butyl 3-(4-amino-5-bromopyrrolo[2,1-f][1,2,4]triazin-7-yl)pyrrolidine-1-carboxylate has been described in WO 2007/056170-A2 (Intermediate I).

This compound (60 mg, 0.16 mmol) was coupled according to general synthetic method 1 with Intermediate 2A (47 mg, 0.17 mmol, 1.1 eq.). The crude product was purified by preparative HPLC (method 2) to give 67 mg (84% of th.) of the title compound.

HPLC (method 2): $R_t$=4.08 min;

LC-MS (method 7): $R_t$=1.66 min; MS (ESIpos): m/z (%)=446.2 (100) [M+H]$^+$, MS (ESIneg): m/z (%)=444.3 (100) [M−H]$^−$.

$^1$H NMR (400 MHz, $d_6$-DMSO): δ (ppm)=1.39 (s, 9H), 2.10 (m, 1H), 2.33 (m, 1H), 3.37 (m, 2H), 3.46 (m, 1H), 3.70-3.89 (m, 2H), 4.51 (s, 2H), 6.80 (s, 1H), 7.15 (m, 2H), 8.03 (s, 1H).

Intermediate 52A rac-tert-Butyl 3-{4-amino-5-[3,5-difluoro-4-(hydroxymethyl)phenyl]pyrrolo[2,1-f][1,2,4]triazin-7-yl}-3-hydroxypiperidine-1-carboxylate

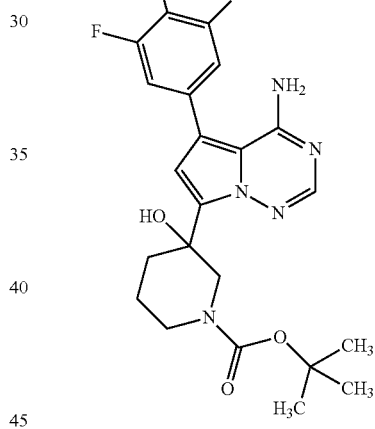

Intermediate 26A (148 mg, 0.35 mmol) and (4-bromo-2,6-difluorophenyl)methanol (75 mg, 0.34 mmol) were coupled according to general synthetic method 2. Purification of the crude product was carried out using preparative HPLC (method 2). Yield: 46 mg (28% of th.).

HPLC (method 3): $R_t$=3.90 min;

LC-MS (method 7): $R_t$=1.56 min; MS (ESIpos): m/z (%)=476.2 (100) [M+H]$^+$, MS (ESIneg): m/z (%)=474.2 (100) [M−H]$^−$.

$^1$H NMR (400 MHz, $d_6$-DMSO): δ (ppm)=1.22-1.58 (m, 10H), 1.80 (m, 2H), 3.19 (m, 1H), 3.48 (m, 1H), 3.62 (m, 1H), 3.74 (m, 1H), 4.00 (m, 1H), 4.52 (m, 2H), 5.39 (t, 1H), 6.78 (s, 1H), 7.10 (m, 2H), 7.94 (s, 1H).

Intermediate 53A tert-Butyl 4-{4-amino-5-[4-(hydroxymethyl)phenyl]pyrrolo[2,1-f][1,2,4]triazin-7-yl}piperidine-1-carboxylate $^1$H NMR (400 MHz, d$_6$-DMSO): δ (ppm)=1.52-1.65 (m, 2H), 1.92-2.00 (m, 2H), 2.89 (br. s, 2H), 3.10 (m, 1H), 3.28-3.37 (m, 2H), 4.06 (d, 2H), 4.60 (s, 2H), 6.68 (s, 1H), 7.47 (s, 5H), 8.02 (s, 1H).

Intermediate 54A rac-tert-Butyl 3-{4-amino-5-[3,5-difluoro-4-(hydroxymethyl)phenyl]pyrrolo[2,1-f][1,2,4]triazin-7-yl}piperidine-1-carboxylate

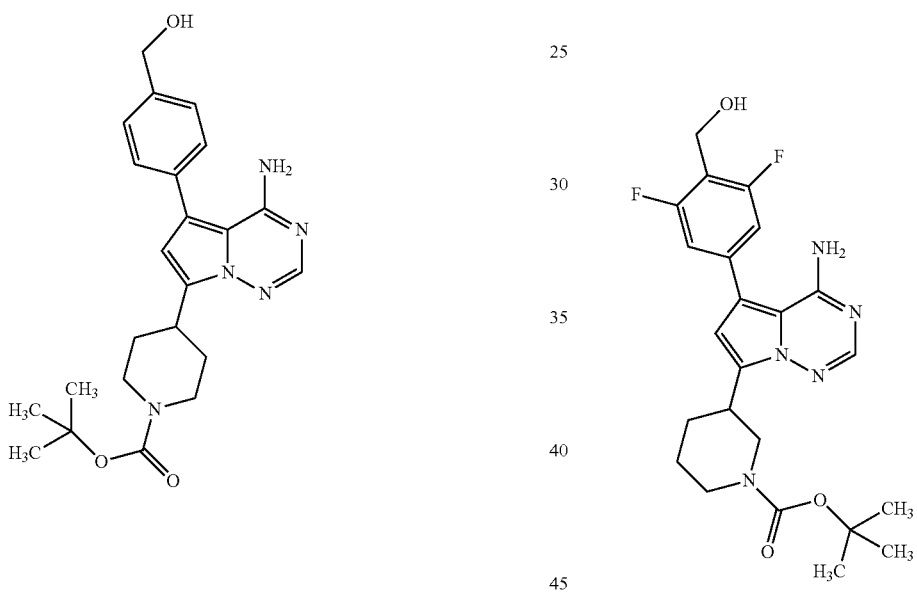

The starting material tert-butyl 4-(4-amino-5-bromopyrrolo[2,1-f][1,2,4]triazin-7-yl)piperidine-1-carboxylate was prepared according to the procedure described in WO 2007/056170-A2 (Example 1, step 3).

This compound (400 mg, 1.01 mmol) was then reacted with 4-(hydroxymethyl)phenylboronic acid (184 mg, 1.21 mmol, 1.2 eq.) according to general synthetic method 1. The crude product was purified by preparative HPLC (method 2) to give 326 mg (76% of th.) of the title compound.

HPLC (method 2): R$_t$=4.07 min;

LC-MS (method 6): R$_t$=1.06 min; MS (ESIpos): m/z (%)=424.3 (100) [M+H]$^+$, MS (ESIneg): m/z (%)=4223 (100) [M−H]$^-$.

Intermediate 31A (200 mg, 0.39 mmol) and Intermediate 2A (138 mg, 0.51 mmol, 1.3 eq.) were reacted according to general synthetic method 1 yielding 130 mg (72% of th.) of the title compound after purification by preparative HPLC (method 2).

HPLC (method 3): R$_t$=4.23 min;

LC-MS (method 6): R$_t$=1.17 min; MS (ESIpos): m/z (%)=460.1 (100) [M+H]$^+$, MS (ESIneg): m/z (%)=458.1 (100) [M−H]$^-$.

$^1$H NMR (400 MHz, $d_6$-DMSO): δ (ppm)=1.39 (s, 9H), 1.48 (m, 2H), 1.74 (m, 2H), 2.93 (m, 1H), 3.22 (m, 1H), 3.85 (m, 1H), 4.11 (m, 1H), 4.53 (s, 2H), 6.78 (s, 1H), 7.12 (m, 2H), 8.02 (s, 1H).

Intermediate 55A tert-Butyl (3R)-3-{4-amino-5-[3,5-difluoro-4-(hydroxymethyl)phenyl]pyrrolo[2,1-f][1,2,4]triazin-7-yl}piperidine-1-carboxylate $^1$H NMR (400 MHz, $d_6$-DMSO): δ (ppm)=1.39 (s, 9H), 1.48 (m, 2H), 1.74 (m, 2H), 2.93 (m, 1H), 3.22 (m, 1H), 3.85 (m, 1H), 4.11 (m, 1H), 4.53 (s, 2H), 6.78 (s, 1H), 7.12 (m, 2H), 8.02 (s, 1H).

Intermediate 56A tert-Butyl (3S)-3-[4-amino-5-[3,5-difluoro-4-(hydroxymethyl)phenyl]pyrrolo[2,1-f][1,2,4]triazin-7-yl]piperidine-1-carboxylate

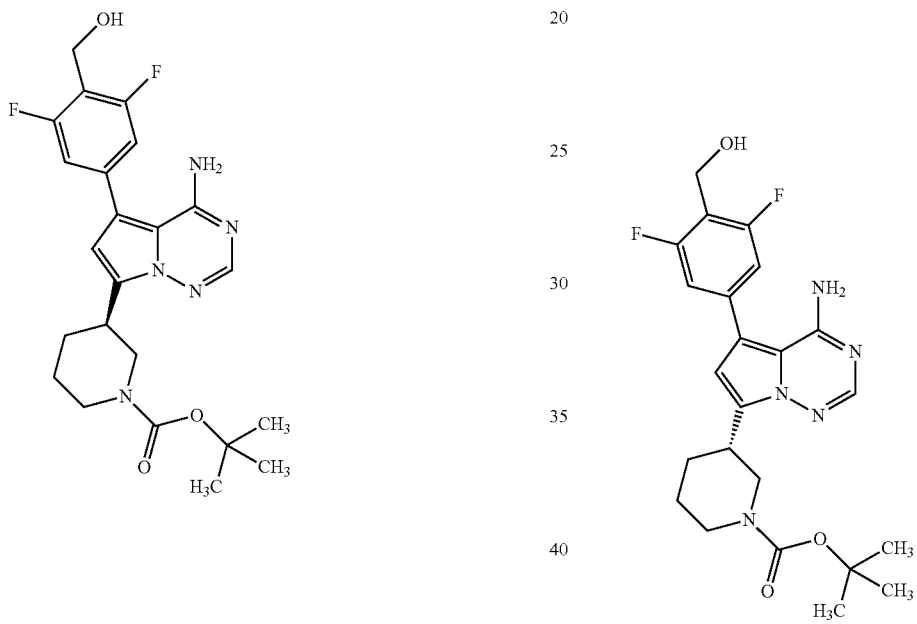

The enantiomerically pure R-isomer was synthesized by coupling Intermediate 32A (115 mg, 0.28 mmol) with (4-bromo-2,6-difluorophenyl)methanol (76 mg, 0.33 mmol, 1.2 eq.) according to general synthetic method 2. Yield: 48 mg (38% of th.).

Alternatively, the title compound was obtained by separation of the racemic compound from Intermediate 54A (40 mg) using preparative chiral HPLC [column: chiral silica gel phase based on the selector poly(N-methacryloyl-L-leucine-tert-butylamide), 250 mm×20 mm; eluent: ethyl acetate/isohexane 4:1; flow rate: 20 mL/min; UV detection: 260 nm]. Yield: 20 mg (R-isomer).

Analytical chiral HPLC [column: chiral silica gel phase based on the selector poly(N-methacryloyl-L-leucine-tert-butylamide), 250 mm×4 mm; eluent: ethyl acetate/isohexane 4:1; flow rate: 1 mL/min; UV detection: 260 nm]: $R_t$=5.68 min; e.e. >99.5.

HPLC (method 3): $R_t$=4.23 min;

LC-MS (method 6): $R_t$=1.17 min; MS (ESIpos): m/z (%)=460.1 (100) [M+H]$^+$, MS (ESIneg): m/z (%)=458.1 (100) [M−H]$^-$.

The enantiomerically pure S-isomer was obtained by separation of the racemic compound from Intermediate 54A (40 mg) using preparative chiral HPLC as described for Intermediate 55A. Yield: 19 mg (S-isomer).

Analytical chiral HPLC [column: chiral silica gel phase based on the selector poly(N-methacryloyl-L-leucine-tert-butylamide), 250 mm×4 mm; eluent: ethyl acetate/isohexane 4:1; flow rate: 1 mL/min; UV detection: 260 nm]: $R_t$=7.87 min; e.e. >99.5.

HPLC (method 3): $R_t$=4.23 min;

LC-MS (method 6): $R_t$=1.17 min; MS (ESIpos): m/z (%)=460.1 (100) [M+H]$^+$, MS (ESIneg): m/z (%)=458.1 (100) [M−H]$^-$.

¹H NMR (400 MHz, d₆-DMSO): δ (ppm)=1.39 (s, 9H), 1.48 (m, 2H), 1.74 (m, 2H), 2.93 (m, 1H), 3.22 (m, 1H), 3.85 (m, 1H), 4.11 (m, 1H), 4.53 (s, 2H), 6.78 (s, 1H), 7.12 (m, 2H), 8.02 (s, 1H).

Intermediate 57A

[2-Fluoro-6-methyl-4-(4,4,5,5-tetramethyl-1,3,2-dioxaborolan-2-yl)phenyl]methanol

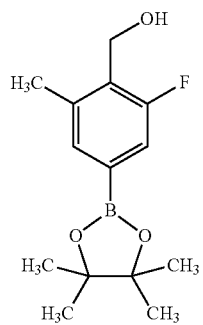

(4-Bromo-2-fluoro-6-methylphenyl)methanol (2.0 g, 9.13 mmol) was dissolved in 1,4-dioxane (20.0 mL) in a microwave reactor vial, and the solution was flushed with argon. Then, bis(pinacolato)diboron (2.43 g, 9.59 mmol), 1,1'-bis(diphenylphosphino)ferrocene-palladium(II) chloride (298 mg, 0.37 mmol) and potassium acetate (1.34 g, 13.7 mmol) were added, the reaction vessel was crimp-capped, and the mixture was heated to 130° C. for 1 h in a single-mode microwave device. After cooling, the reaction mixture was filtered and the filtrate was evaporated. The residue was treated with cyclohexane (100 mL) and stirred for 10 min. The solution was filtered again, the filtrate was evaporated, and the residue was purified by chromatography (Biotage 25M silica cartridge, dichloromethane at 15 mL/min flow rate). Fractions containing the title compound were combined and evaporated, and the title compound crystallized spontaneously as a yellow solid (2.18 g, 90% of th.).
¹H NMR (400 MHz, DMSO-d₆): δ (ppm)=1.30 (s, 12H), 2.39 (s, 3H), 4.51 (m, 2H), 5.01 (t, 1H), 7.14 (d, 1H), 7.31 (s, 1H).

Intermediate 58A

[2-Ethyl-6-fluoro-4-(4,4,5,5-tetramethyl-1,3,2-dioxaborolan-2-yl)phenyl]methanol

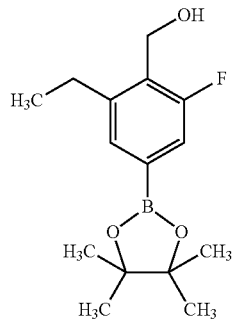 [SMILES: CCc1cc(B2OC(C)(C)C(C)(C)O2)cc(F)c1CO]

The title compound was synthesized and purified in analogy to Intermediate 57A using (4-bromo-2-ethyl-6-fluorophenyl)methanol (2.00 g, 8.58 mmol), bis(pinacolato)diboron (2.29 g, 9.01 mmol), 1,1'-bis(diphenylphosphino)ferrocene-palladium(II) chloride (280 mg, 0.34 mmol) and potassium acetate (1.26 g, 12.87 mmol) in 1,4-dioxane (20 mL). Yield: 2.16 g (90% of th.) as yellow crystals.
¹H NMR (400 MHz, DMSO-d₆): δ (ppm)=1.17 (t, 3H), 1.30 (s, 12H), 2.76 (q, 2H), 4.50 (m, 2H), 5.03 (t, 1H), 7.14 (d, 1H), 7.32 (s, 1H).

Intermediate 59A

[2-Fluoro-6-methoxy-4-(4,4,5,5-tetramethyl-1,3,2-dioxaborolan-2-yl)phenyl]methanol

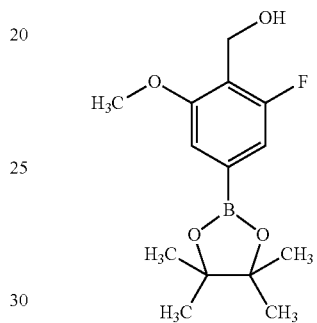

The title compound was synthesized and purified in analogy to Intermediate 57A using (4-bromo-2-methoxy-6-fluorophenyl)methanol (2.00 g, 8.51 mmol), bis(pinacolato)diboron (2.27 g, 8.90 mmol), 1,1'-bis(diphenylphosphino)ferrocene-palladium(II) chloride (278 mg, 0.34 mmol) and potassium acetate (1.25 g, 12.76 mmol) in 1,4-dioxane (20 mL). Yield: 1.81 g (75% of th.) as yellow crystals.
¹H NMR (400 MHz, DMSO-d₆): δ (ppm)=1.30 (s, 12H), 3.83 (s, 3H), 4.47 (m, 2H), 4.86 (t, 1H), 6.97 (d, 1H), 7.02 (s, 1H).

Intermediate 60A 1-(4-Aminopyrrolo[2,1-f][1,2,4]triazin-7-yl)cyclohexanol

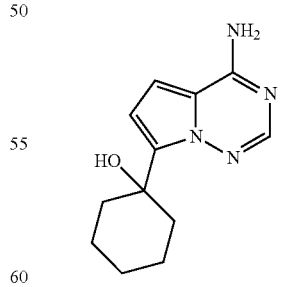

7-Bromopyrrolo[2,1-f][1,2,4]triazin-4-amine (1.20 g, 5.63 mmol) was dissolved in THF (25 mL) under argon at room temperature. Chlorotrimethylsilane (1.43 mL, 11.27 mmol) was added, and the mixture was stirred at room temperature for 3 h. Then, it was cooled to 0° C., 2-propyl magnesium chloride (11.8 mL of a 2.0 M solution in THF, 23.7 mmol) was added, and stirring was maintained for another 3 h while the reaction mixture was allowed to warm to room temperature. Then, cyclohexanone (0.88 mL, 8.45 mmol) was added, and stirring was continued for 16 h. The reaction was quenched with a mixture (1:1) of concentrated aqueous ammonium chloride solution and ice until the pH reached 6-7. The mixture was extracted with two portions of ethyl acetate, and the combined organic extracts were dried over anhydrous sodium carbonate and concentrated to dryness. The product thus obtained was used without further purification (purity 68% by HPLC). Yield: 1.87 g (97% of th.).

LC-MS (method 5): $R_t$=1.10 min; MS (ESIpos): m/z (%)=233 (100) [M+H]$^+$, MS (ESIneg): m/z (%)=231 (100) [M−H]$^−$.

$^1$H NMR (400 MHz, DMSO-d$_6$): δ (ppm)=1.28-1.33 (m, 1H), 1.42-1.50 (m, 2H), 1.58-1.63 (m, 1H), 1.67-1.78 (m, 4H), 2.13-2.23 (m, 2H), 6.69 (d, 1H), 7.20 (d, 1H), 8.02 (s, 1H), 8.58 (br. s, 1H), 9.00 (br. s, 1H).

Intermediate 61A 1-(4-Amino-5-bromopyrrolo[2,1-f][1,2,4]triazin-7-yl)cyclohexanol

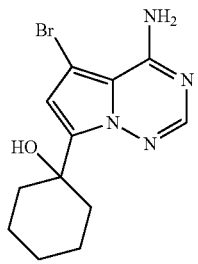 [SMILES: Nc1ncnn2c(C3(O)CCCCC3)cc(Br)c12]

Intermediate 60A (80 mg, 0.34 mmol) was dissolved in THF (5.0 mL), and the mixture was cooled to −20° C. 1,3-Dibromo-5,5-dimethylhydantoin (49 mg, 0.17 mmol) was added at once, and stirring was continued for 1 h. The reaction was quenched with conc. aqueous sodium dithionite solution (0.5 mL and the mixture was extracted with ethyl acetate. The organic extract was washed with brine, dried over sodium sulfate, and the solvent was distilled off to give 98 mg (91% N of th.) of the title compound.

LC-MS (method 4): $R_t$=1.90 min; MS (ESIpos): m/z (%)=311 (95) [M+H]$^+$, MS (ESIneg): m/z (%)=309 (90) [M−H]$^−$.

$^1$H NMR (400 MHz, DMSO-d$_6$): δ (ppm)=1.20-1.33 (m, 1H), 1.42-1.52 (m, 2H), 1.58-1.78 (m, 5H), 2.15-2.23 (m, 2H), 5.01 (br. s, 2H), 6.63 (s, 1H), 7.82 (s, 1H).

Intermediate 62A tert-Butyl {[4-(4-amino-5-bromopyrrolo[2,1-f][1,2,4]triazin-7-yl)-1,3-thiazol-2-yl]methyl}-carbamate

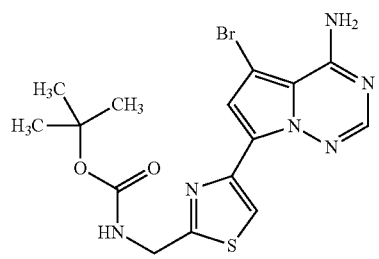 [SMILES: CC(C)(C)OC(=O)NCc1nc(-c2cc(Br)c3c(N)ncnn23)cs1]

Intermediate 33A (109 mg, 0.38 mmol) and tert-butyl (2-amino-2-thioxoethyl)carbamate (79 mg, 0.41 mmol) were dissolved in ethanol (6.5 mL). The mixture was heated to reflux for 20 h. The mixture was then filtered, and the filtrate was evaporated. The residue was triturated with acetonitrile to give 67 mg (42% of th.) of the title compound as a brownish-grey crystalline solid.

LC-MS (method 7): $R_t$=1.81 min; MS (ESIpos): m/z (%)=425 (80) and 427 (100) [M+H]$^+$, MS (ESIneg): m/z (%)=423 (50) and 425 (100) [M−H]$^−$.

Intermediate 63A tert-Butyl 3-{4-amino-5-[3-fluoro-4-(hydroxymethyl)-5-methoxyphenyl]pyrrolo[2,1-f][1,2,4]-triazin-7-yl}piperidine-1-carboxylate

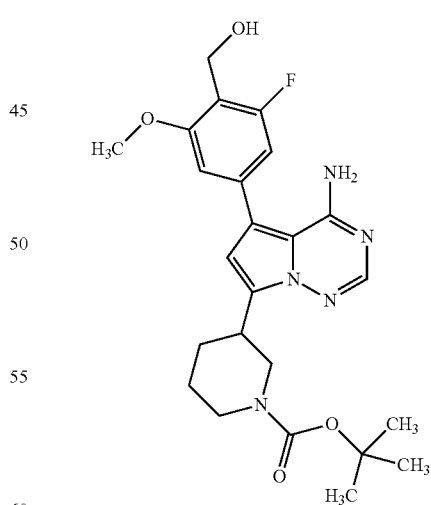

Intermediate 31A (120 mg, 0.30 mmol) and Intermediate 59A (104 mg, 0.36 mmol) were dissolved in acetonitrile (2.0 mL) in a microwave reactor vial and flushed with argon. Tetrakis(triphenylphosphine)palladium(0) (35 mg, 0.03 mmol) and 2.0 M aq. sodium carbonate solution (0.5 mL) were added, and the mixture was heated to 150° C. for 1 h in a single-mode microwave device. After cooling, the mixture was filtered, and the filtrate was evaporated. The residue was purified by flash chromatography (Biotage 25M silica cartridge, dichloromethane+2-5% methanol, flow rate 10 mL/min) to give 51 mg (36% of th.) of the title compound.

LC-MS (method 6): $R_t$=1.16 min; MS (ESIpos): m/z (%)=472 (100) [M+H]$^+$, MS (ESIneg): m/z (%)=470 (100) [M−H]$^−$.

$^1$H NMR (400 MHz, DMSO-d$_6$): δ (ppm)=1.31-2.10 (m, 13H), 2.88-2.91 (m, 2H), 3.19-3.27 (m, 2H), 3.87 (s, 1H), 4.12 (m, 1H), 4.50 (m, 1H), 4.82 (t, 1H), 6.68 (s, 1H), 6.83 (d, 1H), 6.90 (s, 1H), 7.92 (s, 1H).

Intermediate 64A tert-Butyl 3-[4-amino-5-[3-fluoro-4-(hydroxymethyl)-5-methylphenyl]pyrrolo[2,1-f][1,2,4]triazin-7-yl]piperidine-1-carboxylate

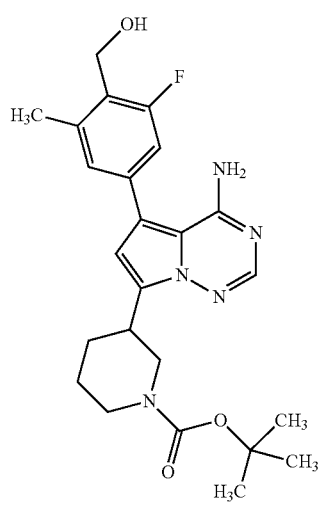 [SMILES: Cc1cc(-c2cc(C3CCCN(C(=O)OC(C)(C)C)C3)n3ncnc(N)c23)cc(F)c1CO]

Intermediate 31A (120 mg, 0.30 mmol) and Intermediate 57A (97 mg, 0.36 mmol) were dissolved in acetonitrile (2.0 mL) in a microwave reactor vial and flushed with argon. Tetrakis(triphenylphosphine)palladium(0) (35 mg, 0.03 mmol) and 2.0 M aq. sodium carbonate solution (0.5 mL) were added, and the mixture was heated to 150° C. for 1 h in a single-mode microwave device. After cooling, the mixture was filtered, and the filtrate was evaporated. The residue was purified by flash chromatography (Biotage 25M silica cartridge, dichloromethane+2-5% methanol, flow rate 10 mL/min) to give 110 mg (71% of th.) of the title compound.

LC-MS (method 4): $R_t$=2.03 min; MS (ESIpos): m/z (%)=456 (100) [M+H]$^+$, MS (ESIneg): m/z (%)=454 (100) [M−H]$^−$.

$^1$H NMR (400 MHz, DMSO-d$_6$): δ (ppm)=1.31-2.11 (m, 13H), 2.42 (s, 3H), 2.88-2.91 (m, 2H), 3.17-3.30 (m, 2H), 3.80 (m, 1H), 4.54 (m, 1H), 4.82 (t, 1H), 6.64 (s, 1H), 7.04 (d, 1H), 7.12 (s, 1H), 7.93 (s, 1H).

Intermediate 65A tert-Butyl 3-[4-amino-5-[3-fluoro-4-(hydroxymethyl)-5-methylphenyl]pyrrolo[2,1-f][1,2,4]triazin-7-yl]pyrrolidine-1-carboxylate

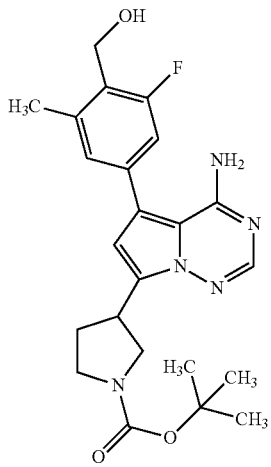 [SMILES: Cc1cc(-c2cc(C3CCN(C(=O)OC(C)(C)C)C3)n3ncnc(N)c23)cc(F)c1CO]

The starting material tert-Butyl 3-(4-amino-5-bromopyrrolo[2,1-f][1,2,4]triazin-7-yl)pyrrolidine-1-carboxylate was synthesized according to the procedure described in WO 2007/056170-A2 (Intermediate I).

tert-Butyl 3-(4-amino-5-bromopyrrolo[2,1-f][1,2,4]triazin-7-yl)pyrrolidine-1-carboxylate (120 mg, 0.31 mmol) was dissolved in acetonitrile (2.2 mL) in a microwave reactor vial and flushed with argon. Intermediate 57A (100 mg, 0.38 mmol), tetrakis(triphenylphosphine)palladium(0) (36 mg, 0.03 mmol) and 2.0 M aq. sodium carbonate solution (0.5 mL) were added, and the mixture was heated to 150° C. for 1 h in a single-mode microwave device. After cooling, the mixture was filtered, and the filtrate was evaporated. The residue was purified by flash chromatography (Biotage 25M silica cartridge, dichloromethane+2-5% methanol, flow rate 10 mL/min) to give 91 mg (54% of th.) of the title compound.

LC-MS (method 5): $R_t$=2.00 min; MS (ESIpos): m/z (%)=442 (100) [M+H]$^+$, MS (ESIneg): m/z (%)=440 (100) [M−H]$^−$.

¹H NMR (400 MHz, DMSO-d₆): δ (ppm)=1.41 (m, 9H), 2.00-2.48 (m, 2H), 3.29-3.53 (m, 3H), 3.71-3.90 (m, 2H), 4.55 (m, 2H), 4.99 (t, 1H), 6.63 (s, 1H), 7.06 (d, 1H), 7.12 (s, 1H), 7.92 (s, 1H).

Intermediate 66A rac-tert-Butyl 3-{4-amino-5-[3-ethyl-5-fluoro-4-(hydroxymethyl)phenyl]pyrrolo[2,1-f][1,2,4]-triazin-7-yl}pyrrolidine-1-carboxylate

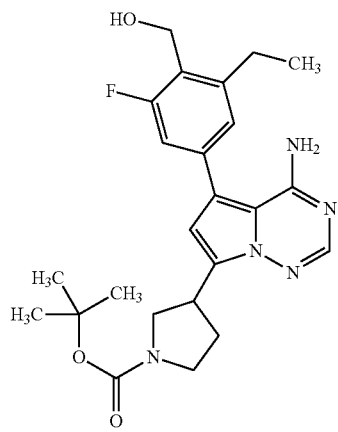 [SMILES: CCc1cc(-c2cc(C3CCN(C(=O)OC(C)(C)C)C3)n3ncnc(N)c23)cc(F)c1CO]

The starting material tert-Butyl 3-(4-amino-5-bromopyrrolo[2,1-f][1,2,4]triazin-7-yl)pyrrolidine-1-carboxylate was synthesized according to the procedure described in WO 2007/056170-A2 (Intermediate I).

tert-Butyl 3-(4-amino-5-bromopyrrolo[2,1-f][1,2,4]triazin-7-yl)pyrrolidine-1-carboxylate (111 mg, 0.29 mmol), Intermediate 58A (98 mg, 0.35 mmol) and tetrakis(triphenylphosphine)palladium(0) (17 mg, 0.015 mmol) were dissolved in a mixture of acetonitrile (2.3 mL) and 2 M aqueous sodium carbonate solution (0.53 mL) in a microwave reactor vial. After degassing for 5 min using argon, the reaction vessel was crimp-capped, and the mixture was heated to 150° C. for 1 h in a single-mode microwave device. After cooling to room temperature, saturated aqueous sodium bicarbonate solution was added, and the mixture was extracted with ethyl acetate. The combined organic layers were dried over sodium sulfate, filtered and concentrated. The residue was purified by preparative HPLC (method 5). Yield: 83 mg (63% of th.).

HPLC (method 9): $R_t$=1.61 min;

LC-MS (method 10): $R_t$=1.02 min; MS (ESIpos): m/z (%)=456.4 (100) [M+H]⁺, MS (ESIneg): m/z (%)=454.4 (100) [M−H]⁻.

¹H NMR (400 MHz, d₆-DMSO): δ (ppm)=1.22 (t, 3H), 1.41 (s, 9H), 2.1 (m, 1H), 2.80 (q, 2H), 3.30-3.43 (m, 2H), 3.44-3.51 (m, 1H), 3.78 (m, 1H), 4.55 (d, 2H), 5.00 (t, 1H), 6.68 (s, 1H), 7.09 (d, 1H), 7.15 (s, 1H), 7.95 (s, 1H).

Intermediate 67A rac-test-Butyl 3-{4-amino-5-[3-ethyl-5-fluoro-4-(hydroxymethyl)phenyl]pyrrolo[2,1-f][1,2,4]-triazin-7-yl}piperidine-1-carboxylate

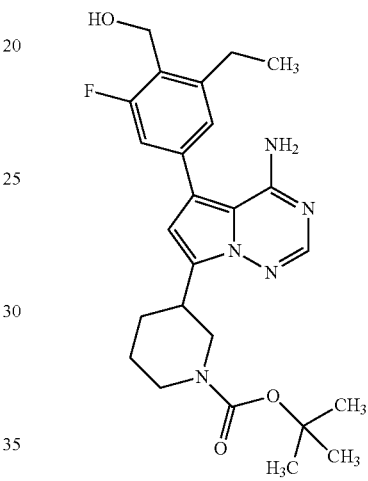

Intermediate 31A (148 mg, 0.29 mmol), Intermediate 58A (98 mg, 0.35 mmol) and tetrakis(triphenylphosphine)palladium(0) (17 mg, 0.015 mmol) were dissolved in a mixture of acetonitrile (2.3 mL) and 2 M aqueous sodium carbonate solution (0.67 mL) in a microwave reactor vial. After degassing for 5 min using argon, the reaction vessel was crimp-capped, and the mixture was heated to 150° C. for 1 h in a single-mode microwave device. After cooling to room temperature, saturated aqueous sodium bicarbonate solution was added, and the mixture was extracted with ethyl acetate. The combined organic layers were dried over sodium sulfate, filtered and concentrated. The residue was purified by preparative HPLC (method 5). Yield: 105 mg (76% of th.).

HPLC (method 9): $R_t$=1.71 min;

LC-MS (method 10): $R_t$=1.08 min; MS (ESIpos): m/z (%)=470.4 (100) [M+H]⁺, MS (ESIneg): m/z (%)=468.4 (75) [M−H]⁻.

¹H NMR (400 MHz, d₆-DMSO): δ (ppm)=1.22 (t, 3H), 1.38 (s, 9H), 1.50 (m, 1H), 1.65-1.90 (m, 2H), 2.06 (m, 1H), 2.80 (q, 2H), 2.98 (m, 1H), 3.20-3.43 (m, 2H), 3.8 (m, 1H), 4.08 (m, 1H), 4.55 (d, 2H), 5.02 (t, 1H), 6.65 (s, 1H), 7.07 (d, 1H), 7.13 (s, 1H), 7.93 (s, 1H).

Intermediate 68A rac-Methyl 4-{4-amino-7-[cyclopropyl(hydroxy) methyl]pyrrolo[2,1-f][1,2,4]triazin-5-yl}-2-methoxybenzoate

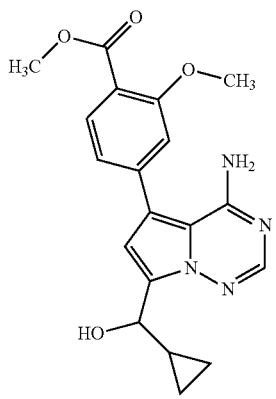 [SMILES: COC(=O)c1ccc(-c2cc(C(O)C3CC3)n3ncnc(N)c23)cc1OC]

Intermediate 17A (250 mg, 0.88 mmol), [3-methoxy-4-(methoxycarbonyl)phenyl]boronic acid (223 mg, 1.06 mmol) and tetrakis(triphenylphosphine)palladium(0) (102 mg, 0.088 mmol) were dissolved in a mixture of 1,4-dioxane (5.5 mL) and 2 M aqueous sodium carbonate solution (1.32 mL) under argon and heated under reflux for 16 h. After this, another portion of tetrakis(triphenylphosphine)palladium(0) (102 mg, 0.088 mmol) was added, and heating was continued for further 24 h. After cooling to room temperature, the reaction mixture was filtered, the filtrate was concentrated, and the residue was purified by preparative HPLC (method 7). Yield: 130 mg (80% purity, 32% of th.).

LC-MS (method 10): $R_t$=0.80 min; MS (ESIpos): m/z (%)=369.3 (100) [M+H]$^+$, MS (ESIneg): m/z (%)=367.3 (75) [M−H]$^−$.

$^1$H NMR (400 MHz, $d_6$-DMSO): δ (ppm)=0.41 (m, 3H), 0.49 (m, 1H), 1.37 (m, 1H), 3.81 (s, 3H), 4.68 (d, 1H), 6.92 (s, 1H), 7.13 (dd, 1H), 7.22 (d, 1H), 7.77 (d, 1H), 8.05 (s, 1H).

Intermediate 69A 7-(Prop-1-en-2-yl)pyrrolo[2,1-f][1,2,4]triazin-4-amine

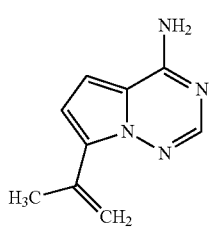

The starting material 7-bromopyrrolo[2,1-f][1,2,4]triazin-4-amine was synthesized according to the procedure described in WO 2007/056170-A2 (Intermediate B).

Under an argon atmosphere, 7-bromopyrrolo[2,1-f][1,2,4]triazin-4-amine (426 mg, 2 mmol) and 4,4,5,5-tetramethyl-2-(prop-1-en-2-yl)-1,3,2-dioxaborolane (420 mg, 2.5 mmol) were dissolved in a mixture of 1,2-dimethoxyethane (10 mL) and aqueous sodium carbonate solution (2 M, 4 mL). The reaction mixture was degassed, and 1,1'-bis(diphenylphosphino)ferrocenepalladium(II) chloride (73 mg, 0.1 mmol) was added. After stirring at 90° C. overnight, the reaction mixture was diluted with ethyl acetate (40 mL), water (10 mL) was added, and the layers were separated. The aqueous layer was extracted with ethyl acetate (2×40 mL), and the combined organic layers were dried over sodium sulfate, filtered and concentrated. The residue was purified by flash chromatography (puriFlash, Interchim, cyclohexane/ethyl acetate 1:1 to 100% ethyl acetate gradient) to yield the title product as a slightly yellow solid. Yield: 304 mg (81% of th.).

HPLC (method 10): $R_t$=0.83 min;

LC-MS (method 10): $R_t$=0.57 min; MS (ESIpos): m/z (%)=175.1 (100) [M+H]$^+$.

$^1$H NMR (400 MHz, $d_6$-DMSO): δ (ppm)=2.15 (s, 3H), 5.22 (m, 1H), 6.30 (m, 1H), 6.73 (d, 1H), 6.91 (d, 1H), 7.69 (m, 1H), 7.91 (s, 1H).

Intermediate 70A

7-Isopropylpyrrolo[2,1-f][1,2,4]triazin-4-amine

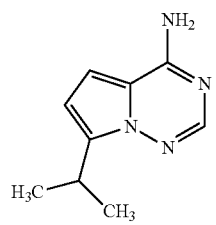

Intermediate 69A (149 mg, 0.86 mmol) was dissolved in a mixture of ethanol and ethyl acetate (1:1, 40 mL) under argon. Palladium on charcoal (10%, 9.1 mg) was added, and the mixture was vigorously stirred for 16 h under an atmosphere of hydrogen at ambient pressure and room temperature. After this, the catalyst was removed by filtration, and the solvent was distilled off under reduced pressure to give 131 mg (80% of th.) of the title compound as a colorless solid. This product was used in the next synthetic step without further purification.

HPLC (method 10): $R_t$=0.81 min;

LC-MS (method 10): $R_t$=0.56 min; MS (ESIpos): m/z (%)=177.0 (100) [M+H]$^+$.

¹H NMR (400 MHz, d₆-DMSO): δ (ppm)=1.27 (d, 6H), 3.36 (m, 1H), 6.41 (d, 1H), 6.80 (d, 1H), 7.48-7.59 (m, 2H), 7.80 (s, 1H).

Intermediate 71A

5-Bromo-7-isopropylpyrrolo[2,1-f][1,2,4]triazin-4-amine

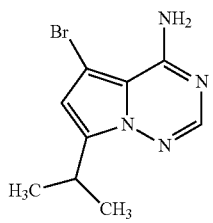

Intermediate 70A (125 mg, 0.71 mmol) was dissolved in dry THF (21 mL) and cooled to −78° C. 1,3-Dibromo-5,5-dimethylhydantoin (81 mg, 0.28 mmol) was added in two equal portions. The reaction mixture was stirred at −78° C. for 1 h and then allowed to warm to room temperature overnight. After addition of water (20 mL) and further stirring for 20 min, the precipitated solid was collected by filtration and dried in vacuo. The crude product thus obtained (209 mg, >100% of th.) was used in the next synthetic step without further purification.

HPLC (method 9): R$_t$=1.35 min.

LC-MS (method 10): R$_t$=091 min; MS (ESIpos): m/z (%)=257.0 (100) [M+H]⁺.

Intermediate 72A rac-1-(4-Amino-5-bromopyrrolo[2,1-f][1,2,4]triazin-7-yl)ethanol

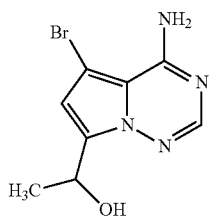

Intermediate 16A (500 mg, 1.66 mmol) was suspended in THF (10 mL) and cooled to 0° C. Methyl magnesium bromide solution (3 N in diethylether, 1.7 mL) was added, and the reaction mixture was stirred for 30 min. Then, saturated aqueous ammonium chloride solution was added, and the mixture was extracted with ethyl acetate (2×20 mL). The combined organic layers were dried over magnesium sulfate, filtered and concentrated to yield 235 mg (46% of th.) of the title product which was used in the next synthetic step without further purification.

LC-MS (method 5): R$_t$=0.73 min; MS (ESIpos): m/z (%)=259.1 (100) [M+H]⁺, MS (ESIneg): m/z (%)=257.1 (100) [M−H]⁻.

¹H NMR (400 MHz, d₆-DMSO): δ (ppm)=1.41 (d, 3H), 5.16 (m, 1H), 5.30 (m, 1H), 6.70 (s, 1H), 7.85 (s, 1H).

PREPARATION EXAMPLES

Example 1

[4-(4-Amino-7-propylpyrrolo[2,1-f][1,2,4]triazin-5-yl)phenyl]methanol

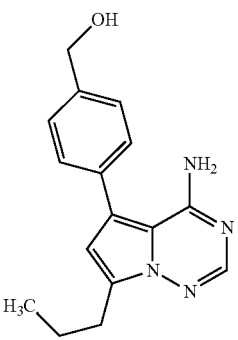 [SMILES: CCCc1cc(-c2ccc(CO)cc2)c2c(N)ncnn12]

The title compound was obtained by general synthetic method 1 from Intermediate 11A (100 mg, 0.39 mmol) and 4-(hydroxymethyl)phenylboronic acid (60 mg, 0.39 mmol). Purification of the crude product was carried out by preparative HPLC (method 2). Yield: 33 mg (30% of th.).

HPLC (method 1): R$_t$=3.47 min; HPLC (method 2): R$_t$=3.78 min;

LC-MS (method 4): R$_t$=0.91 min; MS (ESIpos): m/z (%)=283.2 (100) [M+H]⁺.

¹H NMR (400 MHz, d₆-DMSO): δ (ppm)=0.97 (t, J=7.4 Hz, 3H), 1.71 (m, 2H), 3.31 (s, 2H), 4.52 (s, 2H), 6.54 (s, 1H), 7.42 (s, 4H), 7.89 (s, 1H), Example 2

[4-(4-Amino-7-propylpyrrolo[2,1-f][1,2,4]triazin-5-yl)-2,6-difluorophenyl]methanol

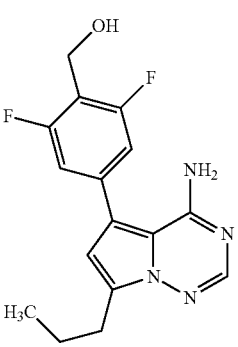 [SMILES: CCCc1cc(-c2cc(F)c(CO)c(F)c2)c2c(N)ncnn12]

The title compound was obtained by general synthetic method 2 from Intermediate 11A (118 mg, 0.46 mmol) and (4-bromo-2,6-difluorophenyl)methanol (108 mg, 0.49 mmol). Purification of the crude product was carried out by preparative HPLC (method 2). Yield: 59 mg (40% of th.).

HPLC (method 2): R$_t$=3.94 min;

LC-MS (method 7): R$_t$=1.47 min; MS (ESIpos): m/z (%)=319.3 (100) [M+H]⁺, MS (ESIneg): m/z (%)=317.3 (100) [M−H]⁻.

¹H NMR (400 MHz, d₆-DMSO): δ (ppm)=0.95 (t, 3H), 1.71 (m, 2H), 4.52 (m, 2H), 5.26 (t, 1H), 6.64 (s, 1H), 7.10 (m, 2H), 7.91 (s, 1H).

Example 3

3-{4-Amino-5-[4-(hydroxymethyl)phenyl]pyrrolo[2,1-f][1,2,4]triazin-7-yl}propan-1-ol

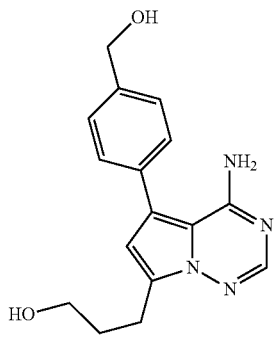 [SMILES: Nc1ncnn2c(CCCO)cc(-c3ccc(CO)cc3)c12]

The title compound was obtained from Intermediate 10A (100 mg, 0.37 mmol) and 4-(hydroxymethyl)phenylboronic acid (67 mg, 0.44 mmol, 1.2 eq.) according to general synthetic method 1. The crude product was purified by preparative HPLC (method 2) to give 73 mg (66% of th.) of the title compound as colorless solid.

HPLC (method 1): R$_t$=2.91 min; HPLC (method 2): R$_t$=3.14 min;

LC-MS (method 6): R$_t$=0.60 min; MS (ESIpos): m/z (%)=299.3 (100) [M+H]⁺, MS (ESIneg): m/z (%)=297.4 (100) [M−H]⁻.

¹H NMR (400 MHz, d₆-DMSO): δ (ppm)=1.84 (m, 2H), 2.95 (t, J=7.6 Hz, 2H), 3.50 (m, 2H), 4.58 (s, 2H), 6.67 (s, 1H), 7.41 (s, 4H), 8.03 (s, 1H).

Example 4

4-{4-Amino-5-[4-(hydroxymethyl)phenyl]pyrrolo[2,1-f][1,2,4]triazin-7-yl}butan-1-ol

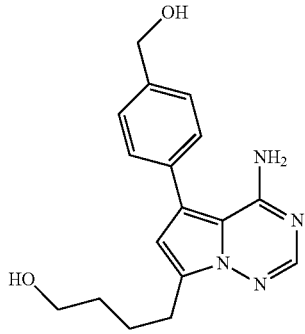 [SMILES: Nc1ncnn2c(CCCCO)cc(-c3ccc(CO)cc3)c12]

The title compound was obtained by general synthetic method 1 from Intermediate 14A (75 mg, 0.26 mmol) and 4-(hydroxymethyl)phenylboronic acid (48 mg, 0.32 mmol). Purification of the crude product was carried out by preparative HPLC (method 2). Yield: 66 mg (80% of th.).

HPLC (method 2): R$_t$=3.28 min;

LC-MS (method 6): R$_t$=0.68 min; MS (ESIpos): m/z (%)=313.3 (100) [M+H]⁺, MS (ESIneg): m/z (%)=311.2 (100) [M−H]⁻.

¹H NMR (400 MHz, d₆-DMSO): δ (ppm)=1.48-1.51 (m, 2H), 1.67-1.70 (m, 2H), 2.91 (t, J=7.6 Hz, 2H), 3.42 (t, J=6.4 Hz, 2H), 4.58 (s, 2H), 6.67 (s, 1H), 7.42 (s, 4H), 8.03 (s, 1H).

Example 5

{4-Amino-5-[3,5-difluoro-4-(hydroxymethyl)phenyl]pyrrolo[2,1-f][1,2,4]triazin-7-yl}(cyclopropyl)methanol

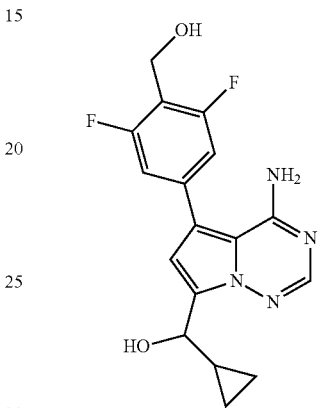

The title compound was obtained from Intermediate 17A (125 mg, 0.44 mmol) and Intermediate 2A (114 mg, 0.53 mmol) by general synthetic method 1. The crude product was purified by preparative HPLC (method 3). Yield: 73 mg (48% of th.).

LC-MS (method 7): R$_t$=1.09 min; MS (ESIpos): m/z (%)=347.3 (100) [M+H]⁺, MS (ESIneg): m/z (%)=345.3 (100) [M−H]⁻.

¹H NMR (400 MHz, d₆-DMSO): δ (ppm)=0.39 (m, 3H), 0.48 (m, 1H), 1.35 (m, 1H), 4.54 (d, 2H), 4.67 (m, 1H), 5.26 (m, 2H), 6.80 (s, 1H), 7.14 (m, 2H), 7.92 (s, 1H).

Example 6

{4-Amino-5-[3,5-difluoro-4-(hydroxymethyl)phenyl]pyrrolo[2,1-f][1,2,4]triazin-7-yl}(tetrahydro-2H-pyran-4-yl)methanol

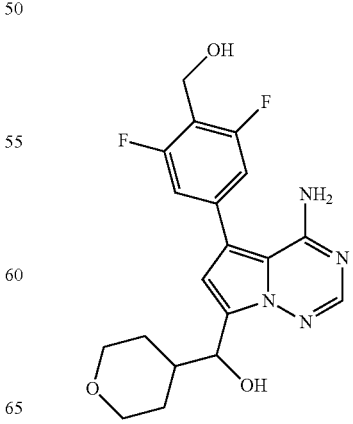

The title compound was obtained from Intermediate 18A (200 mg, 0.61 mmol) and Intermediate 2A (158 mg, 0.73 mmol) by general synthetic method 1. The crude product was purified by preparative HPLC (method 3). Yield: 125 mg (52% of th.).

LC-MS (method 5): $R_t$=1.29 min; MS (ESIpos): m/z (%)=391.1 (100) [M+H]$^+$, MS (ESIneg): m/z (%)=389.0 (100) [M–H]$^-$.

$^1$H NMR (400 MHz, $d_6$-DMSO): δ (ppm)=1.24 (br. d, 1H), 1.36 (m, 2H), 1.68 (br. d, 1H), 2.03 (m, 1H), 2.60 (t, 2H), 3.82 (m, 2H), 4.54 (s, 2H), 4.95 (br. d, 1H), 5.28 (br, 1H), 5.33 (br, 1H), 6.73 (s, 1H), 7.14 (m, 2H), 7.93 (s, 1H).

Example 7 trans-4-[4-Amino-5-[3,5-difluoro-4-(hydroxymethyl)phenyl]pyrrolo[2,1-f][1,2,4]triazin-7-yl]-cyclohexanol

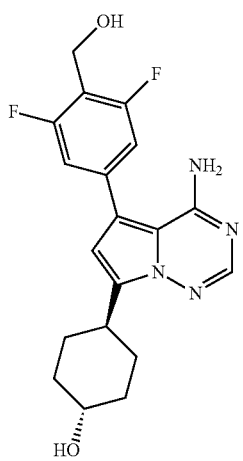 [SMILES: Nc1ncnn2c1c(-c1cc(F)c(CO)c(F)c1)cc2[C@H]1CC[C@H](O)CC1]

The title compound was obtained by general synthetic method 1 from Intermediate 24A (323 mg, 85% purity, 0.88 mmol) and Intermediate 1A (286 mg, 1.06 mmol, 1.2 eq.). Purification of the crude product was first carried out by flash chromatography (Biotage silica packed cartridge, eluent dichloromethane/methanol 95:5). Further purification was performed by preparative HPLC (method 2). Yield: 72 mg (21% of th.).

HPLC (method 2): $R_t$=3.37 min;

LC-MS (method 7): $R_t$=1.01 min; MS (ESIpos): m/z (%)=375.3 (100) [M+H]$^+$, MS (ESIneg): m/z (%)=373.3 (100) [M–H]$^-$.

$^1$H NMR (400 MHz, $d_6$-DMSO): δ (ppm)=1.32 (m, 2H), 1.50 (m, 2H), 1.98 (m, 2H), 2.04 (m, 2H), 3.04 (tt, 1H), 3.47 (m, 1H), 4.51 (m, 2H), 4.61 (d, 1H), 5.26 (t, 1H), 6.60 (s, 1H), 7.12 (m, 21-1), 7.91 (s, 1H).

Example 8 rac-{4-[4-Amino-7-(pyrrolidin-3-yl)pyrrolo[2,1-f][1,2,4]triazin-5-yl]-2,6-difluorophenyl}methanol

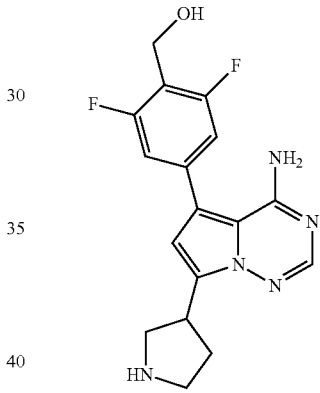

Intermediate 51A (67 mg, 0.15 mmol) was dissolved in a 30% solution of trifluoroacetic acid in dichloromethane (6 mL) at 0° C. The reaction mixture was stirred at this temperature for 20 min, then all volatiles were removed under reduced pressure. The residue was purified by preparative HPLC (method 2). The product thus obtained was dissolved in ethyl acetate and washed with saturated aqueous sodium carbonate solution. The organic layer was dried over anhydrous sodium sulfate, and the solvent was distilled off to give 21 mg (41% of th.) of the title compound.

HPLC (method 2): $R_t$=2.96 min;

LC-MS (method 6): $R_t$=0.34 min; MS (ESIpos): m/z (%)=346.1 (20) [M–H]$^-$, MS (ESIneg): m/z (%)=344.2 (100) [M–H]$^-$.

¹H NMR (400 MHz, d₆-DMSO): δ (ppm)=1.94 (m, 1H), 2.22 (m, 1H), 2.94 (m, 1H), 3.00-3.16 (m, 2H), 3.40 (m, 2H), 3.72 (m, 1H), 4.51 (s, 2H), 5.22 (hr. s, 1H), 6.71 (s, 1H), 7.11 (m, 2H), 7.92 (s, 1H).

Example 9 rac-3-{4-Amino-5-[3,5-difluoro-4-(hydroxymethyl)phenyl]pyrrolo[2,1-f][1,2,4]triazin-7-yl}-piperidin-3-ol

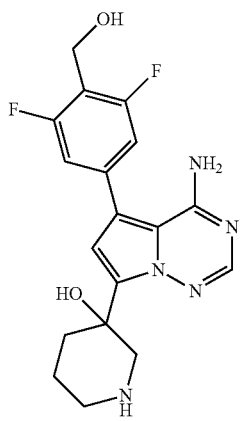 [SMILES: Nc1ncnn2c(C3(O)CCCNC3)cc(-c3cc(F)c(CO)c(F)c3)c12]

Intermediate 52A (46 mg, 0.10 mmol) was dissolved in a 30% solution of trifluoroacetic acid in dichloromethane (1.5 mL) at 0° C. The reaction mixture was stirred at this temperature for 30 min, then all volatiles were removed under reduced pressure. The residue was purified by preparative HPLC (method 2). The product thus obtained was dissolved in ethyl acetate and washed with saturated aqueous sodium carbonate solution. The organic layer was dried over anhydrous sodium sulfate, and the solvent was distilled off to give 20 mg (55% of th.) of the title compound.

HPLC (method 2): R$_t$=2.94 min;

LC-MS (method 4): R$_t$=1.01 min; MS (ESIpos): m/z (%)=358.1 (100) [M−H₂+H]⁺, MS (ESIneg): m/z (%)=374.1 (100) [M−H]⁻.

¹H NMR (400 MHz, d₆-DMSO): δ (ppm)=1.48 (m, 1H), 1.89 (m, 2H), 2.40-2.69 (m, 2), 2.92 (d, 1H), 3.02 (d, 1H), 3.40 (m, 1H), 4.52 (m, 2H), 5.26 (t, 1H), 5.45 (s, 1H), 6.72 (s, 1H), 7.13 (m, 2H), 7.94 (s, 1H).

Example 10

{4-[4-Amino-7-(piperidin-4-yl)pyrrolo[2,1-f][1,2,4]triazin-5-yl]phenyl}methanol

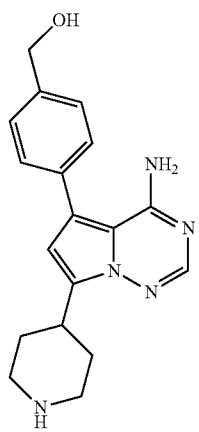 [SMILES: Nc1ncnn2c(C3CCNCC3)cc(-c3ccc(CO)cc3)c12]

Intermediate 53A (324 mg, 0.77 mmol) was dissolved in dichloromethane (15 mL). Trifluoroacetic acid (1.5 mL) was added, and the mixture was stirred at room temperature for 16 h. Another portion of trifluoroacetic acid (1.5 mL) was added, and stirring was continued until HPLC (method 1) indicated complete conversion of the starting material. All volatiles were then removed under reduced pressure, and the residue was purified by preparative HPLC (method 1) to give 226 mg (91% of th.) of the title compound.

HPLC (method 1): R$_t$=3.37 min; HPLC (method 2): R$_t$=2.90 min;

LC-MS (method 4): R$_t$=0.90 min; MS (ESIpos): m/z (%)=324.1 (75) [M+H]⁺, MS (ESIneg): m/z (%)=322.2 (100) [M−H]⁻.

¹H NMR (400 MHz, d₆-DMSO): δ (ppm)=1.79-1.95 (m, 2H), 2.16-2.23 (m, 2H), 3.05-3.19 (m, 2H), 3.37-3.52 (m, 3H), 4.56 (s, 2H), 5.49 (s, 2H), 6.66 (s, 1H), 7.43 (s, 4H), 8.03 (s, 1H), 8.39-8.50 (m, 1H), 8.65-8.69 (m, 1H).

Example 11

(4-{4-Amino-7-[(3R)-piperidin-3-yl]pyrrolo[2,1-f][1,2,4]triazin-5-yl}-2,6-difluorophenyl)methanol

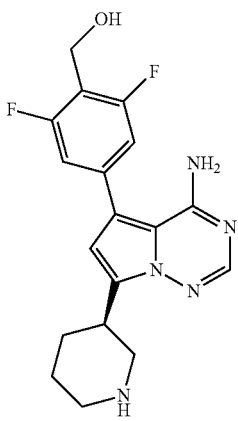 [SMILES: Nc1ncnn2c([C@@H]3CCCNC3)cc(-c3cc(F)c(CO)c(F)c3)c12]

Intermediate 55A (35 mg, 0.08 mmol) was dissolved in a 30% solution of trifluoroacetic acid in dichloromethane (1.5 mL) at 0° C. The reaction mixture was stirred at this temperature for 30 min, then all volatiles were removed under reduced pressure. The residue was purified by preparative HPLC (method 2). The product thus obtained was dissolved in ethyl acetate and washed with saturated aqueous sodium carbonate solution. The organic layer was dried over anhydrous sodium sulfate, and the solvent was distilled off to give 18 mg (66% of th.) of the title compound.

HPLC (method 2): $R_t$=3.10 min;

LC-MS (method 6): $R_t$=0.55 min; MS (ESIpos): m/z (%)=360.2 (20) [M+H]$^+$, MS (ESIneg): m/z (%)=358.3 (100) [M−H]$^−$.

$^1$H NMR (400 MHz, d$_6$-DMSO): δ (ppm)=1.67 (m, 2H), 1.83 (m, 1H), 2.75 (m, 1H), 2.86 (m, 1H), 3.20 (d, 1H), 3.41 (m, 2H), 4.53 (m, 2H), 5.29 (t, 1H), 6.70 (s, 1H), 7.11 (m, 1H), 7.94 (s, 1H).

$[α]_{589}^{20}$=+16.8° (c=0.515, methanol).

Example 12

(4-{4-Amino-7-[(3S)-piperidin-3-yl]pyrrolo[2,1-f][1,2,4]triazin-5-yl}-2,6-difluorophenyl)methanol

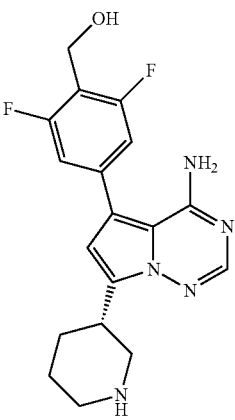 [SMILES: Nc1ncnn2c([C@H]3CCCNC3)cc(-c3cc(F)c(CO)c(F)c3)c12]

The title compound was obtained from Intermediate 56A (19 mg, 0.04 mmol) by the same method as described for the conversion of Intermediate 55A to Example 11. Yield: 12 mg (81% of th.).

HPLC, LC-MS and $^1$H-NMR data were identical to those shown for Example 11.

Example 13

{4-[4-Amino-7-(2-methyl-1,3-thiazol-4-yl)pyrrolo[2,1-f][1,2,4]triazin-5-yl]phenyl}methanol

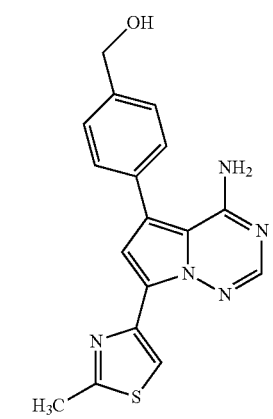 [SMILES: Cc1nc(-c2cc(-c3ccc(CO)cc3)c3c(N)ncnn23)cs1]

Intermediate 33A (60 mg, 0.21 mmol) and thioacetamide (15 mg, 0.20 mmol, 0.95 eq.) were dissolved in 1,4-dioxane (2 mL) and refluxed for 4.5 h. After cooling, 4-(hydroxymethyl)phenylboronic acid (38 mg, 0.25 mmol, 1.2 eq.), tetrakis(triphenylphosphine)palladium(0) (59 mg, 0.07 mmol, 0.25 eq.) and 2 M aqueous sodium carbonate solution (0.4 mL) were added. The mixture was gently stirred at 100° C. for 16 h. Then, another portion of tetrakis(triphenylphosphine)palladium(0) (24 mg, 0.1 eq.) was added, and stirring at 100° C. was continued for another 4 h. The reaction mixture was then filtered, the filtrate was evaporated under reduced pressure, and the residue was purified by preparative HPLC (method 2) to give 28 mg (40% of th.) of the title compound as off-white crystals.

HPLC (method 1): $R_t$=3.85 min; HPLC (method 2): $R_t$=3.60 min;

LC-MS (method 6): $R_t$=0.94 min; MS (ESIpos): m/z (%)=338.2 (100) [M+H]$^+$, MS (ESIneg): m/z (%)=336.1 (100) [M−H]$^-$.

$^1$H NMR (400 MHz, d$_6$-DMSO): δ (ppm)=2.73 (s, 3H), 4.58 (s, 2H), 7.17 (s, 1H), 7.45 (d, J=8.3 Hz, 2H), 7.50 (d, J=8.3 Hz, 2H), 8.09 (s, 1H), 8.33 (s, 1H).

Example 14

{4-[4-Amino-7-(2-methyl-1,3-thiazol-4-yl)pyrrolo[2,1-f][1,2,4]triazin-5-yl]-2,6-difluorophenyl}-methanol

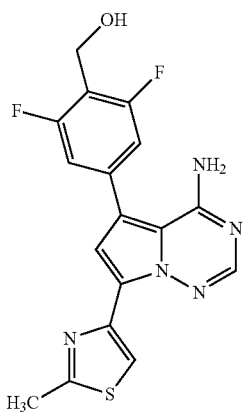 [SMILES: Cc1nc(-c2cc(-c3cc(F)c(CO)c(F)c3)c3c(N)ncnn23)cs1]

The title compound was obtained by general synthetic method 1 from Intermediate 34A (75 mg, 0.24 mmol) and Intermediate 1A (78 mg, 0.29 mmol, 1.2 eq.). Purification of the crude product was carried out by preparative HPLC (method 2). Yield: 27 mg (30% of th.).

HPLC (method 1): $R_t$=3.79 min;

LC-MS (method 6): $R_t$=1.03 min; MS (ESIpos): m/z (%)=374.0 (100) [M+H]$^+$, MS (ESIneg): m/z (%)=372.2 (100) [M−H]$^-$.

$^1$H NMR (400 MHz, d$_6$-DMSO): δ (ppm)=2.72 (s, 3H), 4.53 (s, 2H), 7.18-7.27 (m, 2H), 8.11 (s, 1H), 8.33 (s, 1H).

Example 15

{4-[4-Amino-7-(2-ethyl-1,3-thiazol-4-yl)pyrrolo[2,1-f][1,2,4]triazin-5-yl]phenyl}methanol

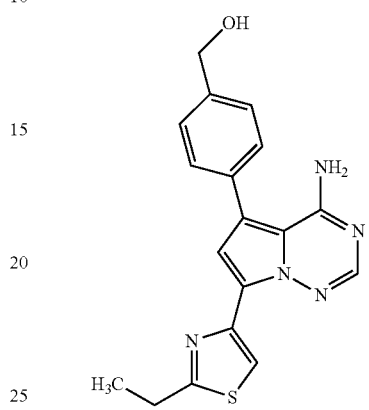

Intermediate 35A (91 mg, 0.28 mmol) was reacted with 4-(hydroxymethyl)phenylboronic acid (51 mg, 0.34 mmol, 1.2 eq.) according to general synthetic method 1. The crude product was purified by preparative HPLC (method 2) giving 68 mg (69% of th.) of the title compound as colorless crystals.

HPLC (method 1): $R_t$=3.73 min;

LC-MS (method 6): $R_t$=1.05 min; MS (ESIpos): m/z (%)=352.2 (100) [M+H]$^+$, MS (ESIneg): m/z (%)=350.3 (100) [M−H]$^-$.

$^1$H NMR (400 MHz, d$_6$-DMSO): δ (ppm)=1.36 (t, J=7.6 Hz, 3H), 3.06 (q, J=7.6 Hz, 2H), 4.58 (s, 2H), 7.19 (s, 1H), 7.46 (d, J=8.0 Hz, 2H), 7.52 (d, J=8.0 Hz, 2H), 8.12 (s, 1H), 8.36 (s, 1H).

Example 16

{4-[4-Amino-7-(2-ethyl-1,3-thiazol-4-yl)pyrrolo[2,1-f][1,2,4]triazin-5-yl]-2,6-difluorophenyl}-methanol

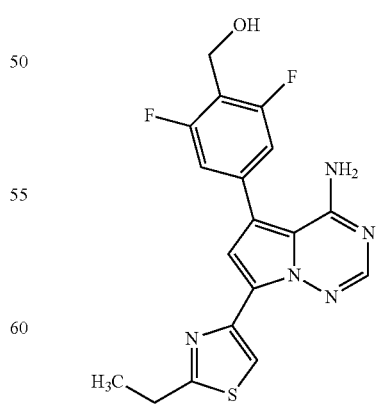

The title compound was obtained by general synthetic method 1 from Intermediate 35A (34 mg, 0.11 mmol) and Intermediate 1A (34 mg, 0.13 mmol, 1.2 eq.). Purification of the crude product was carried out by preparative HPLC (method 2). Yield: 16 mg (40% of th.).

HPLC (method 1): $R_t$=4.04 min;

LC-MS (method 6): $R_t$=1.15 min; MS (ESIpos): m/z (%)=388.0 (100) [M+H]$^+$, MS (ESIneg): m/z (%)=386.1 (100) [M−H]$^−$.

$^1$H NMR (400 MHz, $d_6$-DMSO): δ (ppm)=1.38 (t, 3H), 3.06 (q, 2H), 4.55 (s, 2H), 7.20-7.31 (m, 3H), 8.16 (s, 1H), 8.38 (s, 1H).

Example 17

{4-[4-Amino-7-(2-amino-1,3-thiazol-4-yl)pyrrolo[2,1-f][1,2,4]triazin-5-yl]phenyl}methanol

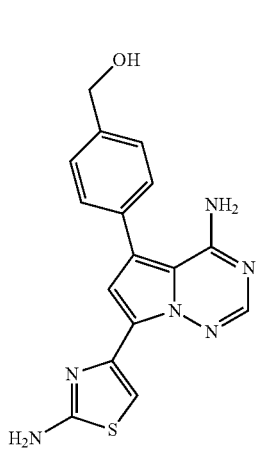 [SMILES: Nc1nc(-c2cc(-c3ccc(CO)cc3)c3c(N)ncnn23)cs1]

The title compound was obtained by general synthetic method 1 from Intermediate 36A (55 mg, 0.18 mmol) and 4-(hydroxymethyl)phenylboronic acid (32 mg, 0.21 mmol). Purification of the crude product was carried out by preparative HPLC (method 2). Yield: 29 mg (49% of th.).

HPLC (method 1): $R_t$=3.03 min;

LC-MS (method 5): $R_t$=1.21 min; MS (ESIpos): m/z (%)=339.1 (30) [M+H]$^+$, MS (ESIneg): m/z (%)=337.1 (100) [M−H]$^−$.

$^1$H NMR (400 MHz, $d_6$-DMSO): δ (ppm)=4.58 (m, 2H), 5.75 (m, 1H), 6.93 (s, 1H), 7.05 (m, 2H), 7.43 (m, 4H), 7.55 (s, 1H), 8.08 (s, 1H).

Example 18

{4-[4-Amino-7-(piperazin-1-ylmethyl)pyrrolo[2,1-f][1,2,4]triazin-5-yl]phenyl}methanol

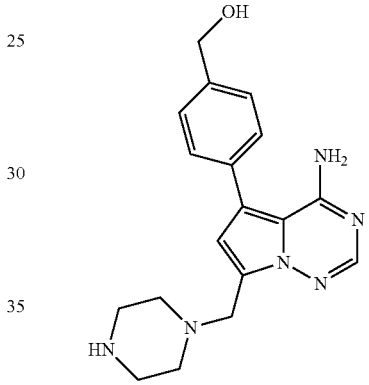

Intermediate 37A (200 mg, 0.49 mmol), 4-(hydroxymethyl)phenylboronic acid (90 mg, 0.59 mmol, 1.2 eq.) and tetrakis(triphenylphosphine)palladium(0) (57 mg, 0.05 mmol, 0.1 eq.) were dissolved in a mixture of 1,4-dioxane (4.0 mL) and 2 M aqueous sodium carbonate solution (1.0 mL) in a microwave reactor vial. The reaction vessel was crimp-capped, and the mixture was heated to 140° C. for 1 h in a single-mode microwave device. After cooling, the mixture was filtered over a pad of Celite which was rinsed with 1,4-dioxane to elute all organic material. The combined filtrate was evaporated to dryness under reduced pressure, and the residue was purified by preparative HPLC (method 1) to give 75 mg (45% of th.) of the title compound.

HPLC (method 1): $R_t$=2.85 min;

LC-MS (method 4): $R_t$=0.93 min; MS (ESIpos): m/z (%)=339.1 (30) [M+H]$^+$, MS (ESIneg): m/z (%)=337.2 (100) [M−H]$^−$.

$^1$H NMR (400 MHz, d$_6$-DMSO): δ (ppm)=2.38 (br. s, 4H), 2.63 (m, 4H), 3.80 (s, 2H), 4.55 (s, 2H), 5.26 (br. s, 1H), 6.60 (s, 1H), 7.39 (s, 4H), 7.90 (s, 1H).

Example 19

{4-[4-Amino-7-(morpholin-4-ylmethyl)pyrrolo[2,1-f][1,2,4]triazin-5-yl]phenyl}methanol

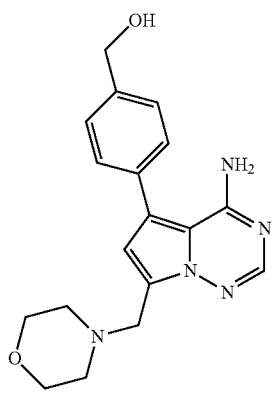 [SMILES: Nc1ncnn2c(CN3CCOCC3)cc(-c3ccc(CO)cc3)c12]

The title compound was obtained from Intermediate 38A (200 mg, 0.64 mmol) and 4-(hydroxymethyl)phenylboronic acid (116 mg, 0.77 mmol, 1.2 eq.) according to general synthetic method 1. The crude product was purified by preparative HPLC (method 2). The material thus obtained was dissolved in a few mL of a mixture of acetonitrile and water, 2 M aqueous sodium carbonate solution was added, and the mixture was stirred for 10 min. During this time, the title compound precipitated. The crystals were isolated by filtration and dried in vacuo to give 95 mg (49% of th.) of a colorless solid.

HPLC (method 1): R$_t$=3.21 min;

LC-MS (method 4): R$_t$=0.93 min; MS (ESIpos): m/z (%)=340 (1) [M+H]$^+$, MS (ESIneg): m/z (%)=338.2 (100) [M−H]$^-$.

$^1$H NMR (400 MHz, d$_6$-DMSO): δ (ppm)=2.47 (m, 4H), 3.31 (s, 4H), 3.53 (t, 2H), 3.82 (s, 1H), 4.56 (d, 2H), 5.22 (t, 1H), 6.63 (s, 1H), 7.42 (s, 4H), 7.90 (s, 1H).

Example 20

{4-[4-Amino-7-(morpholin-4-ylmethyl)pyrrolo[2,1-f][1,2,4]triazin-5-yl]-2,6-difluorophenyl}-methanol

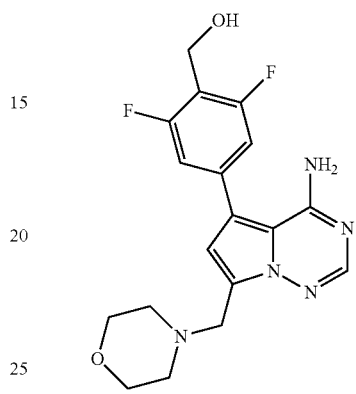

To a solution of Intermediate 40A (110 mg, 0.22 mmol) in THF (2.2 mL) was added 0.45 mL (0.45 mmol) of a 1 M solution of tetrabutylammonium fluoride (TBAF) in THF, and the mixture was stirred at room temperature for 1 h. The reaction mixture was then evaporated under reduced pressure, and the residue was suspended in 3 mL of methanol and stirred at room temperature for 5 min. The resulting precipitate was filtered, washed with a small amount of methanol and dried in vacuo to give 68 mg (81% of th.) of the title compound.

LC-MS (method 4): R$_t$=1.03 min; MS (ESIpos): m/z (%)=376.0 (80) [M+H]$^+$, MS (ESIneg): m/z (%)=374.1 (100) [M−H]$^-$.

$^1$H NMR (400 MHz, d$_6$-DMSO): δ (ppm)=2.45 (br. m, 4H), 3.56 (t, 4H), 3.82 (s, 2H), 4.54 (d, 2H), 5.27 (t, 1H), 6.75 (s, 1H), 7.16 (m, 2H), 7.95 (s, 1H).

Example 21

{4-[4-Amino-7-(morpholin-4-ylmethyl)pyrrolo[2,1-f][1,2,4]triazin-5-yl]-2-fluorophenyl}methanol

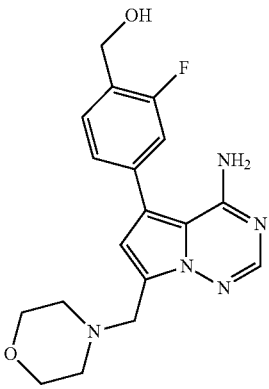 [SMILES: Nc1ncnn2c(CN3CCOCC3)cc(-c3ccc(CO)c(F)c3)c12]

To a suspension of Intermediate 41A (65.0 mg, 0.17 mmol) in THF (2.0 mL) was added 0.2 mL (0.2 mmol) of a 1 M solution of lithium aluminium hydride in THF, and the mixture was stirred at room temperature for 1 h. The resulting solution was quenched with water and then directly purified by preparative HPLC (method 3) to give 35 mg (58% of th.) of the title compound.

LC-MS (method 6): $R_t$=0.98 min; MS (ESIpos): m/z (%)=358.1 (20) [M+H]$^+$, MS (ESIneg): m/z (%)=356.2 (100) [M−H]$^-$.

$^1$H NMR (400 MHz, d$_6$-DMSO): δ (ppm)=2.46 (br. m, 4H), 3.56 (t, 4H), 3.83 (s, 2H), 4.60 (d, 2H), 5.32 (t, 1H), 6.70 (s, 1H), 7.27 (dd, 2H), 7.55 (t, 1H), 7.94 (s, 1H).

Example 22

{4-[4-Amino-7-(morpholin-4-ylmethyl)pyrrolo[2,1-f][1,2,4]triazin-5-yl]-2-chlorophenyl}methanol

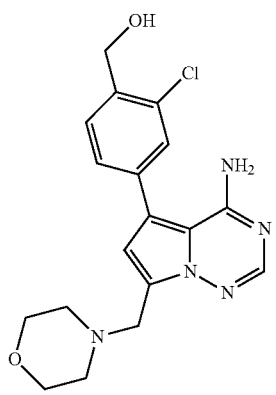 [SMILES: Nc1ncnn2c(CN3CCOCC3)cc(-c3ccc(CO)c(Cl)c3)c12]

Intermediate 39A (200 mg, 0.56 mmol), Intermediate 3A (112 mg, 0.51 mmol) and tetrakis(triphenylphosphine)palladium(0) (58 mg, 0.05 mmol) were dissolved in a mixture of 1,4-dioxane (4.0 mL) and 2 M aqueous sodium carbonate solution (1.0 mL) in a microwave reactor vial. The reaction vessel was crimp-capped, and the mixture was heated to 140° C. for 1 h in a single-mode microwave device. After cooling, the mixture was filtered, and the filtrate was purified by preparative HPLC (method 3) to give 48 mg (23% of th.) of the title compound.

LC-MS (method 6): $R_t$=0.53 min; MS (ESIpos): m/z (%)=374.1 (80) [M+H]$^+$, MS (ESIneg): m/z (%)=372.2 (100) [M−H]$^-$.

$^1$H NMR (400 MHz, d$_6$-DMSO): δ (ppm)=2.46 (br. m, 4H), 3.56 (t, 4H), 3.83 (s, 2H), 4.61 (d, 2H), 5.45 (t, 1H), 6.70 (s, 1H), 7.44 (dd, 1H), 7.49 (d, 1H), 7.63 (t, 1H), 7.94 (s, 1H).

Example 23

{4-[4-Amino-7-(morpholin-4-ylmethyl)pyrrolo[2,1-f][1,2,4]triazin-5-yl]-2-methylphenyl}methanol

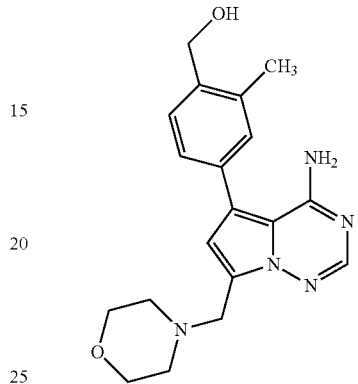

In analogy to the preparation of Example 28, Intermediate 39A (200 mg, 0.56 mmol) was reacted with Intermediate 4A (102 mg, 0.51 mmol) to give 9 mg (5% of th.) of the title compound.

LC-MS (method 4): $R_t$=1.00 min; MS (ESIpos): m/z (%)=3543 (10) [M+H]$^+$, MS (ESIneg): m/z (%)=372.2 (100) [M−H]$^-$.

$^1$H NMR (400 MHz, d$_6$-DMSO): δ (ppm)=2.30 (s, 3H), 2.45 (br. m, 4H), 3.56 (t, 4H), 3.83 (s, 2H), 4.54 (d, 2H), 5.13 (t, 1H), 6.63 (s, 1H), 7.26 (s, 1H), 7.26 (d, 1H), 7.45 (d, 1H), 7.91 (s, 1H).

Example 24

{5-[4-Amino-7-(morpholin-4-ylmethyl)pyrrolo[2,1-f][1,2,4]triazin-5-yl]pyridin-2-yl}methanol

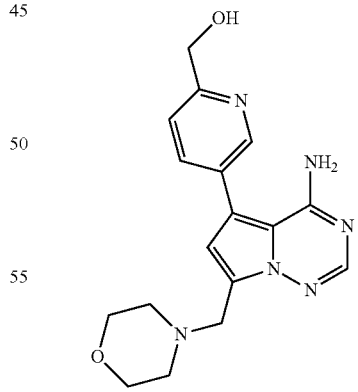

The title compound was obtained from Intermediate 38A (200 mg, 0.64 mmol) and Intermediate 6A (147 mg, 0.96 mmol) by general synthetic method 1. The crude product was purified by preparative HPLC (method 4). Remaining impurities were removed by suspending the product in acetonitrile (2 mL) and collecting the remaining solid by filtration. Yield: 27 mg (12% of th.).

LC-MS (method 4): $R_t$=0.78 min; MS (ESIpos): m/z (%)=341 (10) [M+H]$^+$, MS (ESIneg): m/z (%)=339.3 (100) [M–H]$^-$.

$^1$H NMR (400 MHz, d$_6$-DMSO): δ (ppm)=2.46 (br. m, 4H), 3.56 (t, 4H), 3.84 (s, 2H), 4.62 (d, 2H), 5.46 (t, 1H), 6.73 (s, 1H), 7.54 (d, 1H), 7.86 (dd, 1H), 7.95 (d, 1H), 8.56 (s, 1H).

Example 25

1-({4-Amino-5-[3,5-difluoro-4-(hydroxymethyl)phenyl]pyrrolo[2,1-f][1,2,4]triazin-7-yl}methyl)piperidin-4-ol

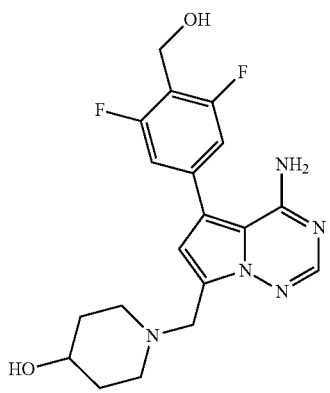 [SMILES: Nc1ncnn2c(CN3CCC(O)CC3)cc(-c3cc(F)c(CO)c(F)c3)c12]

The title compound was obtained from Intermediate 45A (200 mg, 0.61 mmol) and Intermediate 2A (159 mg, 0.74 mmol) by general synthetic method 1. The crude product was purified by preparative HPLC (method 3). Yield: 103 mg (43% of th.).

LC-MS (method 4): $R_t$=0.98 min; MS (ESIpos): m/z (%)=390.1 (60) [M+H]$^+$, MS (ESIneg): m/z (%)=388.2 (100) [M–H]$^-$.

$^1$H NMR (400 MHz, d$_6$-DMSO): δ (ppm)=1.36 (br. m, 2H), 1.68 (br. m, 2H), 2.12 (br. m, 2H), 2.75 (br. m, 2H), 3.41 (br. m, 1H), 3.79 (s, 2H), 4.51 (d, 1H), 4.54 (d, 2H), 5.27 (t, 1H), 6.72 (s, 1H), 7.15 (m, 2H), 7.94 (s, 1H).

Example 26

1-({4-Amino-5-[3,5-difluoro-4-(hydroxymethyl)phenyl]pyrrolo[2,1-f][1,2,4]triazin-7-yl}methyl)pyrrolidin-3-ol

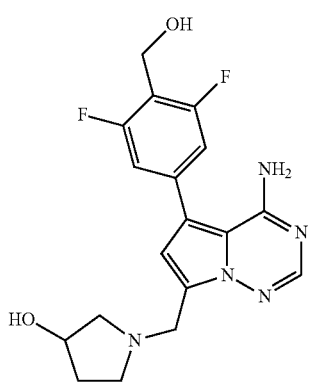 [SMILES: Nc1ncnn2c(CN3CCC(O)C3)cc(-c3cc(F)c(CO)c(F)c3)c12]

The title compound was obtained from Intermediate 47A (110 mg, 0.35 mmol) and Intermediate 2A (91.3 mg, 0.42 mmol) by general synthetic method 1. The crude product was purified by preparative HPLC (method 3). Yield: 69 mg (52% of th.).

LC-MS (method 4): $R_t$=0.25 min; MS (ESIpos): m/z (%)=376.1 (20) [M+H]$^+$.

$^1$H NMR (400 MHz, d$_6$-DMSO): δ (ppm)=1.54 (m, 1H), 1.98 (m, 1H), 2.43 (br. d, 1H), 2.69 (m, 1H), 2.79 (dd, 1H), 3.93 (dd, 2H), 4.18 (br, 1H), 4.53 (d, 2H), 4.69 (d, 1H), 5.27 (t, 1H), 6.75 (s, 1H), 7.16 (m, 2H), 7.95 (s, 1H).

Example 27

1-({4-Amino-5-[3,5-difluoro-4-(hydroxymethyl)phenyl]pyrrolo[2,1-f][1,2,4]triazin-7-yl]methyl)piperidin-3-ol

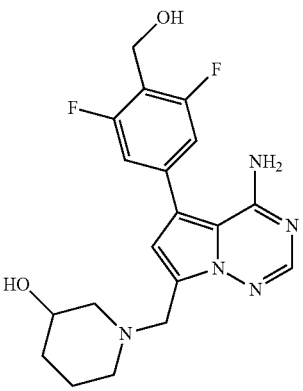 [SMILES: Nc1ncnn2c(CN3CCCC(O)C3)cc(-c3cc(F)c(CO)c(F)c3)c12]

To a solution of Intermediate 50A (150 mg, 0.30 mmol) in THF (3.0 mL) was added 0.60 mL (0.60 mmol) of a 1 M solution of tetrabutylammonium fluoride (TBAF) in THF, and the mixture was stirred at room temperature for 1 h. The reaction mixture was then concentrated, and the residue was purified by preparative HPLC (method 3) to give 65 mg (56% of th.) of the title compound.

LC-MS (method 7): $R_t$=0.33 min; MS (ESIpos): m/z (%)=390.3 (100) [M+H]$^+$.

$^1$H NMR (400 MHz, d$_6$-DMSO): δ (ppm)=1.02 (br. m, 1H), 1.40 (br. m, 1H), 1.60 (br. m, 1H), 1.77 (br. m, 2H), 1.95 (br. m, 1H), 2.73 (br. m, 1H), 2.88 (br. m, 1H), 3.43 (br. m, 1H), 3.83 (br. m, 2H), 4.54 (br. d, 3H), 5.27 (t, 1H), 6.74 (s, 1H), 7.15 (m, 2H), 7.95 (s, 1H).

Example 28 trans-4-{4-Amino-5-[3-ethyl-5-fluoro-4-(hydroxymethyl)phenyl]pyrrolo[2,1-f][1,2,4]triazin-7-yl}-cyclohexanol

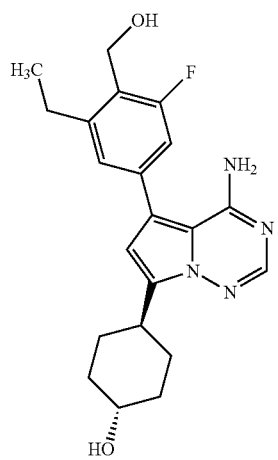 [SMILES: CCc1cc(-c2cc([C@H]3CC[C@H](O)CC3)n3ncnc(N)c23)cc(F)c1CO]

Intermediate 24A (120 mg, 0.39 mmol) and Intermediate 58A (130 mg, 0.46 mmol) were dissolved in acetonitrile (3.0 mL) in a microwave reactor vial and flushed with argon. Tetrakis(triphenylphosphine)palladium(0) (22 mg, 0.02 mmol) and 2.0 M aq. sodium carbonate solution (0.7 mL) were added, and the mixture was heated to 150° C. for 1 h in a single-mode microwave device. After cooling, the mixture was filtered, and the filtrate was evaporated. The residue was purified by preparative HPLC (method 2) to give 36 mg (23% of th.) of the title compound.

LC-MS (method 6): $R_t$=0.82 min; MS (ESIpos): m/z (%)=385 (100) [M+H]$^+$, MS (ESIneg): m/z (%)=383 (100) [M−H]$^-$.

$^1$H NMR (400 MHz, DMSO-d$_6$): δ (ppm)=1.24 (t, 3H), 1.28-1.38 (m, 2H), 1.46-1.54 (m, 2H), 1.94-1.97 (m, 2H), 2.01-2.05 (m, 2H), 2.82 (q, 2H), 3.03 (m, 1H), 3.47 (m, 1H), 4.53 (m, 2H), 4.61 (d, 1H), 5.02 (t, 1H), 6.58 (s, 1H), 7.08 (d, 1H), 7.15 (s, 1H), 7.90 (s, 1H).

Example 29 trans-4-{4-Amino-5-[3-fluoro-4-(hydroxymethyl)-5-methoxyphenyl]pyrrolo[2,1-f][1,2,4]triazin-7-yl}cyclohexanol

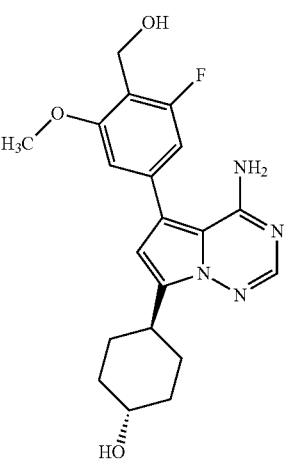 [SMILES: COc1cc(-c2cc([C@H]3CC[C@H](O)CC3)n3ncnc(N)c23)cc(F)c1CO]

Intermediate 24A (120 mg, 0.39 mmol) and Intermediate 59A (163 mg, 80% purity, 0.46 mmol) were dissolved in acetonitrile (2.0 mL) in a microwave reactor vial and flushed with argon. Tetrakis(triphenylphosphine)palladium(0) (45 mg, 0.04 mmol) and 2.0 M aq. sodium carbonate solution (0.5 mL) were added, and the mixture was heated to 150° C. for 1 h in a single-mode microwave device. After cooling, the mixture was filtered, and the filtrate was evaporated. The residue was purified by preparative HPLC (method 2) to give 6 mg (4% of th.) of the title compound.

LC-MS (method 5): $R_t$=1.36 min; MS (ESIpos): m/z (%)=387 (100) [M+H]$^+$, MS (ESIneg): m/z (%)=385 (100) [M−H]$^-$.

$^1$H NMR (400 MHz, DMSO-d$_6$): δ (ppm)=1.24-1.33 (m, 2H), 1.42-1.53 (m, 2H), 1.90-1.93 (m, 2H), 2.00-2.04 (m, 2H), 3.04 (m, 1H), 3.46 (m, 1H), 3.82 (s, 3H), 4.48 (m, 2H), 4.60 (d, 1H), 4.83 (t, 1H), 6.60 (s, 1H), 6.85 (d, 1H), 6.90 (s, 1H), 7.91 (s, 1H).

Example 30

{4-[4-Amino-7-(piperidin-3-yl)pyrrolo[2,1-f][1,2,4]triazin-5-yl]-2-fluoro-6-methoxyphenyl}-methanol

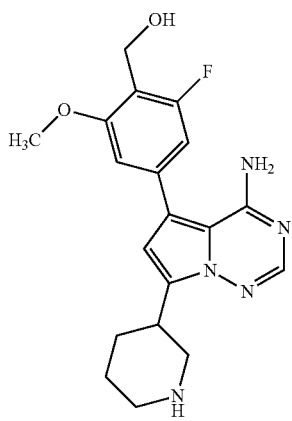 [SMILES: COc1cc(-c2cc(C3CCCNC3)n3ncnc(N)c23)cc(F)c1CO]

Intermediate 63A (50 mg, 0.11 mmol) was dissolved in a 30% solution of trifluoroacetic acid in dichloromethane (5.0 mL) at 0° C. The reaction mixture was stirred at this temperature for 30 min, then all volatiles were removed by distillation under reduced pressure. The residue was purified by preparative HPLC (method 2). The product thus obtained was dissolved in ethyl acetate and washed with saturated aqueous sodium carbonate solution. The organic layer was dried over anhydrous sodium sulfate, and the solvent was distilled off to give 30 mg (76% of th.) of the title compound.

LC-MS (method 6): $R_t$=0.59 min; MS (ESIpos): m/z (%)=372 (10) [M+H]$^+$, MS (ESIneg): m/z (%)=370 (100) [M−H]$^-$.

$^1$H NMR (400 MHz, DMSO-d$_6$): δ (ppm)=1.50-2.08 (m, 4H), 2.94 (m, 2H), 3.17-3.30 (m, 3H), 3.85 (s, 3H), 4.51 (m, 2H), 4.82 (t, 1H), 6.60 (s, 1H), 6.84 (d, 1H), 6.89 (s, 1H), 7.90 (s, 1H).

Example 31

{4-[4-Amino-7-(piperidin-3-yl)pyrrolo[2,1-f][1,2,4]triazin-5-yl]-2-fluoro-6-methylphenyl}-methanol

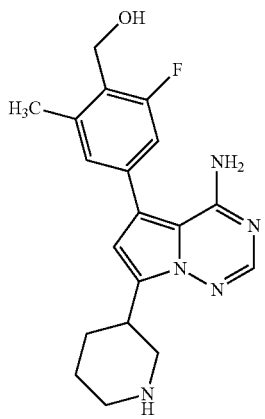 [SMILES: Cc1cc(-c2cc(C3CCCNC3)n3ncnc(N)c23)cc(F)c1CO]

Intermediate 64A (110 mg, 0.21 mmol) was dissolved in a 30% solution of trifluoroacetic acid in dichloromethane (5.0 mL) at 0° C. The reaction mixture was stirred at this temperature for 30 min, then all volatiles were removed by distillation under reduced pressure. The residue was purified by preparative HPLC (method 2). The product thus obtained was dissolved in ethyl acetate and washed with saturated aqueous sodium carbonate solution. The organic layer was dried over anhydrous sodium sulfate, and the solvent was distilled off to give 59 mg (78% of th.) of the title compound.

LC-MS (method 4): $R_t$=1.10 min; MS (ESIpos): m/z (%)=356 (40) [M+H]$^+$, MS (ESIneg): m/z (%)=354 (100) [M−H]$^-$.

$^1$H NMR (400 MHz, DMSO-d$_6$): δ (ppm)=1.44-2.08 (m, 4H), 2.42 (s, 3H), 2.94 (m, 2H), 3.17-3.27 (m, 3H), 4.53 (m, 2H), 4.98 (t, 1H), 6.54 (s, 1H), 7.06 (d, 1H), 7.11 (s, 1H), 7.90 (s, 1H).

Example 32

{4-[4-Amino-7-(pyrrolidin-3-yl)pyrrolo[2,1-f][1,2,4]triazin-5-yl]-2-fluoro-6-methylphenyl}-methanol

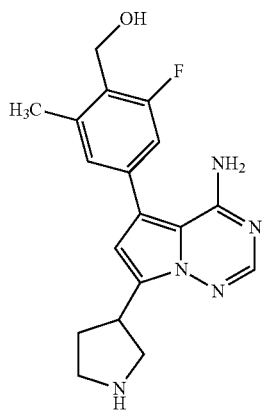 [SMILES: Cc1cc(-c2cc(C3CCNC3)n3ncnc(N)c23)cc(F)c1CO]

Intermediate 65A (90 mg, 0.17 mmol) was dissolved in a 30% solution of trifluoroacetic acid in dichloromethane (5.0 mL) at 0° C. The reaction mixture was stirred at this temperature for 30 min, then all volatiles were removed by distillation under reduced pressure. The residue was purified by preparative HPLC (method 2). The product thus obtained was dissolved in ethyl acetate and washed with saturated aqueous sodium carbonate solution. The organic layer was dried over anhydrous sodium sulfate, and the solvent was distilled off to give 27 mg (47% of th.) of the title compound.

LC-MS (method 4): $R_t$=1.03 min; MS (ESIpos): m/z (%)=342 (100) [M+H]$^+$, MS (ESIneg): m/z (%)=340 (100) [M−H]$^-$.

$^1$H NMR (400 MHz, DMSO-d$_6$): δ (ppm)=1.80-2.21 (m, 2H), 2.43 (s, 3H), 2.78-2.81 (m, 1H), 2.85-3.02 (m, 2H), 3.22-3.27 (m, 1H), 3.63 (m, 1H), 4.55 (br. s, 2H), 4.98 (t, 1H), 6.63 (s, 1H), 7.06 (d, 1H), 7.11 (s, 1H), 7.90 (s, 1H).

Example 33

1-{4-Amino-5-[3,5-difluoro-4-(hydroxymethyl)phenyl]pyrrolo[2,1-f][1,2,4]triazin-7-yl}cyclohexanol trifluoroacetate

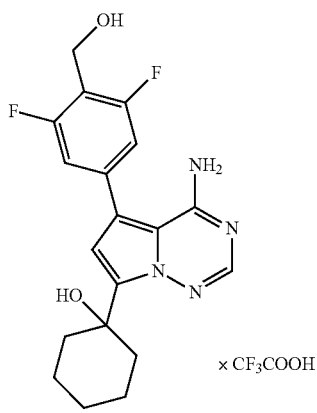 [SMILES: Nc1ncnn2c(C3(O)CCCCC3)cc(-c3cc(F)c(CO)c(F)c3)c12]

× CF₃COOH

Intermediate 61A (95 mg, 0.31 mmol) and Intermediate 1A (87 mg, 0.32 mmol) were dissolved in DMF (2.0 mL) in a microwave reactor vessel and flushed with argon. Tetrakis(triphenylphosphine)palladium(0) (35 mg, 0.03 mmol) and 2.0 M aq. sodium carbonate solution (0.5 mL) were added, and the mixture was heated to 150° C. for 1 h in a single-mode microwave device. After cooling, the mixture was filtered, and the filtrate was directly purified by preparative HPLC (method 2) to give 6 mg (4% of th.) of the title compound.

LC-MS (method 6): $R_t$=1.05 min; MS (ESIpos): m/z (%)=375 (100) [M+H]⁺, MS (ESIneg): m/z (%)=373 (100) [M−H]⁻.

¹H NMR (400 MHz, DMSO-$d_6$): δ (ppm)=1.20-1.33 (m, 1H), 1.42-1.51 (m, 2H), 1.60-1.82 (m, 5H), 2.17-2.28 (m, 2H), 4.51 (s, 2H), 6.76 (s, 1H), 7.17 (m, 2H), 8.02 (s, 1H).

Example 34

(4-[4-Amino-7-[2-(aminomethyl)-1,3-thiazol-4-yl]pyrrolo[2,1-f][1,2,4]triazin-5-yl]-2,6-difluorophenyl)methanol

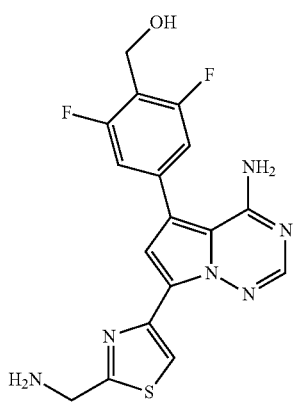

Intermediate 62A (67 mg, 0.16 mmol), Intermediate 1A (51 mg, 0.19 mmol), tetrakis(triphenylphosphine)palladium (0) (18 mg, 0.02 mmol) and 2.0 M aq. sodium carbonate solution (0.94 mL) were dissolved in 1,4-dioxane (2.50 mL) in a microwave reactor vial. The vial was crimp-capped, and the mixture was heated to 140° C. for 3 h in a single-mode microwave device. Then, the reaction mixture was filtered, and the filtrate was diluted with acetonitrile and treated with diethyl ether. The resulting precipitate was collected and purified by preparative HPLC (method 2). The product thus obtained (15 mg) was subsequently treated with a 20% solution of trifluoroacetic acid in dichloromethane (2 mL) for 20 min. The volatiles were removed by distillation, and the residue was treated with conc. aqueous sodium carbonate solution and extracted with ethyl acetate. The organic extract was dried over anhydrous sodium sulfate, and the solvent was distilled off to give the title compound (10 mg, 13% of th.) as a colorless solid.

LC-MS (method 4): $R_t$=1.12 min; MS (ESIpos): m/z (%)=389 (25) [M+H]⁺, MS (ESIneg): m/z (%)=387 (100) [M−H]⁻.

¹H NMR (400 MHz, $d_6$-DMSO): δ (ppm)=4.24 (s, 2H), 4.53 (m, 2H), 5.30 (t, 1H), 7.18-7.23 (m, 3H), 8.11 (s, 1H), 8.40 (s, 1H).

Example 35 ent-{4-[4-Amino-7-(pyrrolidin-3-yl)pyrrolo[2,1-f][1,2,4]triazin-5-yl]-2,6-difluorophenyl}methanol (enantiomer 1)

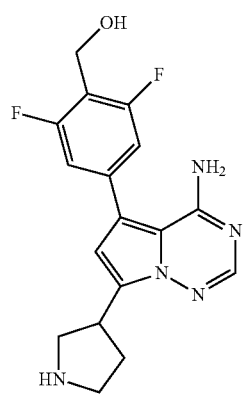 [SMILES: Nc1ncnn2c(C3CCNC3)cc(-c3cc(F)c(CO)c(F)c3)c12]

The title compound was obtained by separation of racemic Example 8 (54 mg) using preparative chiral HPLC [column: Daicel Chiralpak AD-H, 250 mm×20 mm; eluent: isohexane/ethanol 35:65; flow rate: 20 mL/min; UV detection: 220 nm]. Yield: 12.5 mg.

Analytical chiral HPLC [column: Daicel Chiralpak AD-H, 5 μm, 250 mm×4.6 mm; eluent: isohexane/ethanol 50:50+0.2% diethylamine; flow rate: 1.0 mL/min; temperature: 40° C.; UV detection: 220 nm]: $R_t$=9.452 min, e.e. >99%.

HPLC (method 9): $R_t$=0.70 min;

LC-MS (method 10): $R_t$=0.42 min; MS (ESIpos): m/z (%)=346.1 (100) [M+H]⁺, MS (ESIneg): m/z (%)=344.0 (100) [M−H]⁻.

Example 36 ent-{4-[4-Amino-7-(pyrrolidin-3-yl)pyrrolo[2,1-f][1,2,4]triazin-5-yl]-2,6-difluorophenyl}methanol (enantiomer 2)

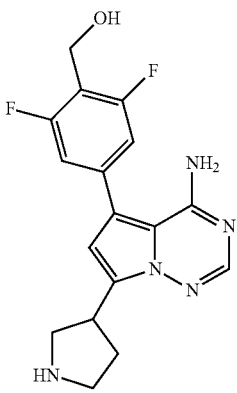 [SMILES: Nc1ncnn2c(C3CCNC3)cc(-c3cc(F)c(CO)c(F)c3)c12]

The title compound was obtained by separation of racemic Example 8 (54 mg) using preparative chiral HPLC [column: Daicel Chiralpak AD-H, 250 mm×20 mm; eluent: isohexane/ethanol 35:65; flow rate: 20 mL/min; UV detection: 220 nm]. Yield: 14 mg.

Analytical chiral HPLC [column: Daicel Chiralpak AD-H, 5 μm, 250 mm×4.6 mm; eluent: isohexane/ethanol 50:50+0.2% diethylamine; flow rate: 1.0 mL/min; temperature: 40° C.; UV detection: 220 nm]: $R_t$=13.695 min, e.e. >99%.

HPLC (method 9): $R_t$=0.71 min;

LC-MS (method 10): $R_t$=0.42 min; MS (ESIpos): m/z (%)=346.1 (100) [M+H]$^+$, MS (ESIneg): m/z (%)=344.0 (100) [M−H]$^−$.

Example 37 rac-{4-[4-Amino-7-(pyrrolidin-3-yl)pyrrolo[2,1-f][1,2,4]triazin-5-yl]-2-ethyl-6-fluorophenyl}-methanol

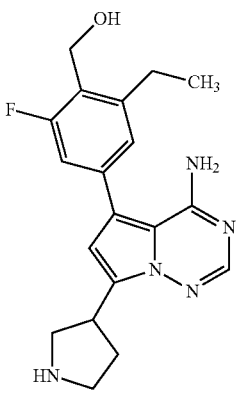 [SMILES: CCc1cc(-c2cc(C3CCNC3)n3ncnc(N)c23)cc(F)c1CO]

Intermediate 66A (72 mg, 0.158 mmol) was dissolved in dichloromethane (3.8 mL) at 0° C. and trifluoroacetic acid (1.0 mL) was added. The reaction mixture was stirred at 0° C. for 40 min, then all volatiles were removed under reduced pressure. The residue was purified by preparative HPLC (method 6). The combined product containing fractions were adjusted to basic pH using saturated aqueous sodium carbonate solution and concentrated to dryness. The resulting residue was suspended in ethyl acetate (50 mL) and filtered. The organic layer was washed with brine (5 mL), dried over anhydrous sodium sulfate, and the solvent was distilled off to give 31 mg (56% of th.) of the title compound.

HPLC (method 9): $R_t$=0.81 min;

LC-MS (method 10): $R_t$=0.55 min; MS (ESIpos): m/z (%)=356.3 (50) [M+H]$^+$, MS (ESIneg): m/z (%)=354.2 (100) [M−H]$^−$.

$^1$H NMR (400 MHz, d$_6$-DMSO): δ (ppm)=1.23 (t, 3H), 1.84-2.24 (m, 1H), 2.81 (q, 2H), 2.80-2.99 (m, 1H), 3.00-3.72 (m, 1H), 4.56 (d, 2H), 5.00 (t, 1H), 6.68 (s, 1H), 7.09 (d, 1H), 7.14 (m, 2H), 7.92 (s, 1H).

Example 38 rac-{4-[4-Amino-7-(piperidin-3-yl)pyrrolo[2,1-f][1,2,4]triazin-5-yl]-2-ethyl-6-fluorophenyl}-methanol

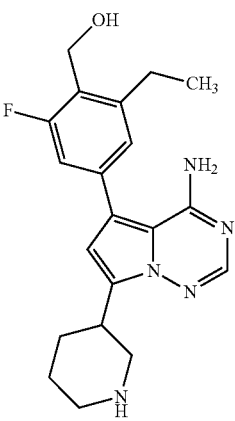 [SMILES: CCc1cc(-c2cc(C3CCCNC3)n3ncnc(N)c23)cc(F)c1CO]

Intermediate 67A (108 mg, 0.230 mmol) was dissolved in dichloromethane (5.2 mL) at 0° C. and trifluoroacetic acid (1.4 mL) was added. The reaction mixture was stirred at 0° C. for 40 min, then all volatiles were removed under reduced pressure. The residue was purified by preparative HPLC (method 6). The combined product containing fractions were adjusted to basic pH using saturated aqueous sodium carbonate solution and concentrated to dryness. The resulting residue was suspended in ethyl acetate (50 mL) and filtered. The organic layer was washed with brine (5 mL), dried over anhydrous sodium sulfate, and the solvent was distilled off to give 83 mg (85% of th.) of the title compound.

HPLC (method 9): $R_t$=0.81 min;

LC-MS (method 10): $R_t$=0.58 min; MS (ESIpos): m/z (%)=370.3 (50) [M+H]$^+$, MS (ESIneg): m/z (%)=368.3 (100) [M−H]$^−$.

$^1$H NMR (400 MHz, d$_6$-DMSO): δ (ppm)=1.22 (t, 3H), 1.51-1.72 (m, 2H), 2.00-2.10 (m, 1H), 2.51-2.65 (m, 2H), 2.81 (q, 2H), 2.95-3.03 (m, 1H), 3, 20-3.27 (m, 1H), 4.56 (d, 2H), 5.00 (t, 1H), 6.60 (s, 1H), 7.07 (d, 1H), 7.14 (m, 2H), 7.91 (s, 1H).

Example 39 rac-{4-Amino-5-[3-ethyl-5-fluoro-4-(hydroxymethyl)phenyl]pyrrolo[2,1-f][1,2,4]triazin-7-yl}-(cyclopropyl)methanol

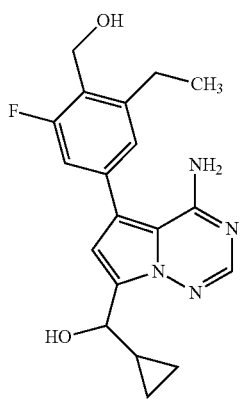 [SMILES: CCc1cc(-c2cc(C(O)C3CC3)n3ncnc(N)c23)cc(F)c1CO]

Intermediate 17A (83 mg, 0.29 mmol), Intermediate 58A (98 mg, 0.35 mmol) and tetrakis(triphenylphosphine)palladium(0) (17 mg, 0.015 mmol) were dissolved in a mixture of acetonitrile (2.3 mL) and 2 M aqueous sodium carbonate solution (0.53 mL) in a microwave reactor vial. After degassing for 5 min using argon, the reaction vessel was crimp-capped, and the mixture was heated to 150° C. for 1 h in a single-mode microwave device. After cooling to room temperature, saturated aqueous sodium bicarbonate solution was added, and the mixture was extracted three times with ethyl acetate. The combined organic layers were dried over sodium sulfate, filtered and concentrated. The residue was purified by preparative HPLC (method 5) to give the title compound. Yield: 63 mg (61% of th.).

HPLC (method 9): $R_t$=1.13 min;

LC-MS (method 10): $R_t$=0.78 min: MS (ESIpos): m/z (%)=357.3 (100) [M+H]$^+$, MS (ESIneg): m/z (%)=355.3 (100) [M−H]$^-$.

$^1$H NMR (400 MHz, d$_6$-DMSO): δ (ppm)=0.39 (m, 3H), 0.48 (m, 1H), 1.23 (t, 3H), 1.35 (m, 1H), 2.81 (q, 2H), 4.56 (d, 2H), 4.68 (m, 1H), 5.01 (m, 1H), 5.21 (m, 1H), 6.76 (s, 1H), 7.09 (d, 1H), 7.14 (s, 1H), 7.90 (s, 1H).

Example 40 rac-{4-Amino-5-[4-(hydroxymethyl)-3-methoxyphenyl]pyrrolo[2,1-f][1,2,4]triazin-7-yl}(cyclopropyl)methanol

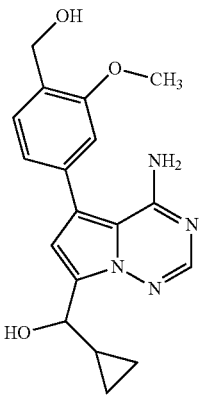 [SMILES: COc1cc(-c2cc(C(O)C3CC3)n3ncnc(N)c23)ccc1CO]

Intermediate 68A (130 mg, 0.353 mmol) was dissolved in tetrahydrofuran (6.9 mL) and cooled to 0° C. Lithium aluminium hydride solution (1 M in diethylether, 0.78 mL) was added dropwise, and the reaction mixture was allowed to warm to room temperature overnight. The reaction mixture was then quenched with water and filtered. The filtrate was concentrated, and the residue was purified by preparative HPLC (method 8) to give the title compound. Yield: 63 mg (51% of th.).

LC-MS (method 10): $R_t$=0.62 min; MS (ESIpos): m/z (%)=341.2 (100) [M+H]$^+$, MS (ESIneg): m/z (%)=339.1 (100) [M−H]$^-$.

Example 41 ent-4-Amino-5-[4-(hydroxymethyl)-3-methoxyphenyl]pyrrolo[2,1-f][1,2,4]triazin-7-yl}(cyclopropyl)methanol (enantiomer 1)

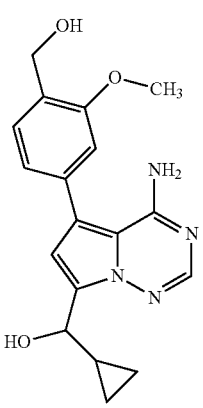 [SMILES: COc1cc(-c2cc(C(O)C3CC3)n3ncnc(N)c23)ccc1CO]

The title compound was obtained by separation of racemic Example 40 (63 mg) using preparative chiral HPLC [column: Daicel Chiralpak IC, 5 μm, 250 mm×20 mm; eluent: tert-butyl methyl ether/methanol 85:15; flow rate: 15 mL/min; temperature: 40° C.; UV detection: 220 nm]. Yield: 17 mg.

Analytical chiral HPLC [column: Daicel Chiralpak IC, 5 μm, 250 mm×4.6 mm; eluent: tert-butyl methyl ether/methanol 85:15; flow rate: 1.0 mL/min; temperature: 40° C.; UV detection: 220 nm]: $R_t$=4.76 min, e.e. >99%.

LC-MS (method 10): $R_t$=0.67 min; MS (ESIpos): m/z (%)=341.2 (100) [M+H]$^+$, MS (ESIneg): m/z (%)=339.1 (100) [M−H]$^−$.

$^1$H NMR (400 MHz, $d_6$-DMSO): δ (ppm)=0.40 (m, 3H), 0.48 (m, 1H), 1.36 (m, 1H), 3.83 (s, 3H), 4.54 (d, 2H), 4.68 (m, 1H), 5.07 (t, 1H), 5.25 (d, 1H), 6.74 (s, 1H), 7.00 (s, 1H), 7.03 (d, 1H), 7.47 (d, 1H), 7.89 (s, 1H).

Example 42 ent-4-Amino-5-[4-(hydroxymethyl)-3-methoxyphenyl]pyrrolo[2,1-f][1,2,4]triazin-7-yl}(cyclopropyl)methanol (enantiomer 2)

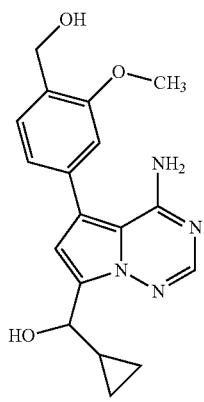 [SMILES: COc1cc(-c2cc(C(O)C3CC3)n3ncnc(N)c23)ccc1CO]

The title compound was obtained by separation of racemic Example 40 (63 mg) using preparative chiral HPLC [column: Daicel Chiralpak IC, 5 μm, 250 mm×20 mm; eluent: tert-butyl methyl ether/methanol 85:15; flow rate: 15 mL/min; temperature: 40° C.; UV detection: 220 nm]. Yield: 25 mg.

Analytical chiral HPLC [column: Daicel Chiralpak IC, 5 μm, 250 mm×4.6 mm; eluent: tert-butyl methyl ether/methanol 85:15; flow rate: 1.0 mL/min; temperature: 40° C.; UV detection: 220 nm]: $R_t$=6.37 min, e.e. >99%.

LC-MS (method 10): $R_t$=0.67 min; MS (ESIpos): m/z (%)=341.2 (100) [M+H]$^+$, MS (ESIneg): m/z (%)=339.1 (100) [M−H]$^−$.

$^1$H NMR (400 MHz, $d_6$-DMSO): δ (ppm)=0.40 (m, 3H), 0.48 (m, 1H), 1.36 (m, 1H), 3.83 (s, 3H), 4.54 (d, 2H), 4.68 (m, 1H), 5.07 (t, 1H), 5.25 (d, 1H), 6.74 (s, 1H), 7.00 (s, 1H), 7.03 (d, 1H), 7.47 (d, 1H), 7.89 (s, 1H).

Example 43

[4-(4-Amino-7-isopropylpyrrolo[2,1-f][1,2,4]triazin-5-yl)-2,6-difluorophenyl]methanol

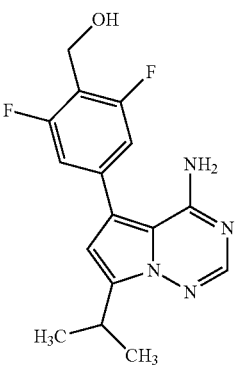 [SMILES: CC(C)c1cc(-c2cc(F)c(CO)c(F)c2)c2c(N)ncnn12]

Intermediate 71A (181 mg, 0.709 mmol), Intermediate 1A (239 mg, 0.887 mmol) and tetrakis(triphenylphosphine)palladium(0) (41 mg, 0.035 mmol) were dissolved in a mixture of N,N-dimethylformamide (12.5 mL) and 2 M aqueous sodium carbonate solution (1.42 mL) in a microwave reactor vial. The reaction vessel was crimp-capped, and the mixture was heated to 130° C. for 2 h in a single-mode microwave device. After cooling to room temperature, the reaction mixture was filtered through Celite and concentrated. The resulting residue was dissolved in ethyl acetate (100 mL) and washed with water and with brine (10 mL each). The organic layer was dried over sodium sulfate, filtered and concentrated. The residue was purified by flash chromatography (puriFlash, Interchim, cyclohexane/ethyl acetate 1:1 to 100% ethyl acetate gradient) followed by preparative HPLC (method 6). The product containing fractions were combined and adjusted to basic pH using saturated aqueous sodium carbonate solution. The acetonitrile solvent was removed, and the precipitated product was collected by filtration. Yield: 69 mg (31% of th.).

HPLC (method 9): $R_t$=1.35 min;

LC-MS (method 10): $R_t$=0.90 min; MS (ESIpos): m/z (%)=319.0 (100) [M+H]$^+$, MS (ESIneg): m/z (%)=317.0 (100) [M−H]$^−$.

$^1$H NMR (400 MHz, d$_6$-DMSO): δ (ppm)=1.30 (d, 6H), 3.42 (m, 1H), 4.54 (s, 2H), 5.26 (s, 1H), 6.65 (s, 1H), 7.14 (m, 2H), 7.94 (s, 1H).

Example 44 rac-1-{4-Amino-5-[3,5-difluoro-4-(hydroxymethyl) phenyl]pyrrolo[2,1-f][1,2,4]triazin-7-yl}-ethanol

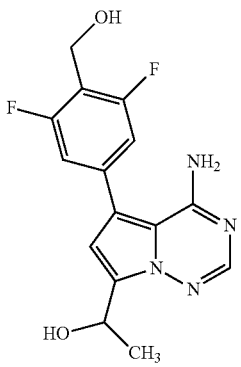 [SMILES: CC(O)c1cc(-c2cc(F)c(CO)c(F)c2)c2c(N)ncnn12]

Intermediate 72A (230 mg, 0.743 mmol), Intermediate 2A (192 mg, 0.89 mmol) and tetrakis(triphenylphosphine)palladium(0) (86 mg, 0.074 mmol) were dissolved in a mixture of 1,4-dioxane (4.6 mL) and 2 M aqueous sodium carbonate solution (1.16 mL) in a microwave reactor vial. The reaction vessel was crimp-capped, and the mixture was heated to 140° C. for 1 h in a single-mode microwave device. After cooling to room temperature, the reaction mixture was purified by preparative HPLC (method 8) to yield 48 mg of material which was further purified by preparative HPLC (method 9). Yield: 11 mg (4.6% of th.).

LC-MS (method 5): R$_t$=0.89 min; MS (ESIpos): m/z (%)=321.3 (100) [M+H]$^+$, MS (ESIneg): m/z (%)=319.3 (100) [M−H]$^−$.

$^1$H NMR (400 MHz, d$_6$-DMSO): δ (ppm)=1.47 (d, 3H), 4.54 (m, 2H), 5.16-5.39 (m, 2H), 6.74 (s, 1H), 6.88 (m, 1H), 7.14 (m, 2H), 7.94 (s, 1H).

B. Evaluation Of Biological Activity

Abbreviations and Acronyms
ATCC American Type Culture Collection
ATP adenosine triphosphate
Bq Bequerel
BrdU 5-bromo-2-deoxyuridine
BSA bovine serum albumin
CHO Chinese hamster ovary
cpm counts per minute
Ct cycle threshold
DMEM/F12 Dulbecco's modified Eagle's medium/Ham's F12 medium (1:1)
DMSO dimethyl sulfoxide
DNA deoxyribonucleic acid
DTT dithiothreitol
EDTA ethylenediamine-tetraacetic acid
ENGS MV microvascular endothelial cell culture medium
FAM carboxyfluorescein succinimidyl ester
FCS fetal calf serum
hBMP9 human bone morphogenic factor 9
HEPES 4-(2-hydroxyethyl)piperazine-1-ethanesulfonic acid
HMVEC human microvascular endothelial cell(s)
HPMC hydroxypropyl methyl cellulose
HTRF homogeneous time resolved fluorescence
HUVEC human vascular endothelial cell(s)
[I] inhibitor concentration
IC$_{50}$ concentration with 50% inhibitory effect
LDH lactate dehydrogenase
mRNA messenger ribonucleic acid
NADH nicotinamide adenine dinucleotide
Nonidet P40 4-ethylphenoxy-poly(ethyleneglycol)ether (n=11)
PBS phosphate buffered saline
PE polyethylene
PEG polyethylene glycol
PK pyruvate kinase
p.o. per os
qPCR quantitative polymerase chain reaction
RNA ribonucleic acid
RTL buffer RNeasy lysis buffer
SEQ ID NO sequence identity number
SFM serum free medium
TAMRA carboxytetramethylrhodamine
Tris 2-amino-2-hydroxymethylpropane-1,3-diol
Triton X-100 4-tert-octylphenoxy-poly(ethyleneglycol)ether (n=10)

Demonstration of the activity of the compounds of the present invention may be accomplished through in vitro, ex vivo, and in vivo assays that are well known in the art. For example, to demonstrate the activity of the compounds of the present invention, the following assays may be used.

B-1a. In Vitro Enzyme Inhibition Using Scintillation of Incorporated Radio Label (Flashplate Assay)

Test Principle:

Test compounds diluted in DMSO are mixed with a suitable substrate/co-substrate (here: biotinylated α-casein and $^{33}$P-ATP) in a corresponding assay buffer. Addition of the enzyme of interest (here: ALK1 kinase) starts the enzyme reaction. The enzyme-catalyzed incorporation of radio label into the substrate is measured via scintillation. Incorporated radio label is separated from free radio label via specific binding of the biotinylated substrate to strepavidin-coated microtiter plates (flashplates) and concomitant washing steps. The scintillation signal intensity (counts per minutes, cpm) is proportional to the enzyme activity. Enzyme inhibition results in a decreased signal intensity. IC$_{50}$ values of the test compounds are determined by cpm-versus-[I] plots.

Reaction Buffer:

Reaction buffer contains 50 mM Tris pH 8.0 (Sigma), 1 mM MnCl$_2$ (Sigma), 0.01% Nonidet P40 (Fluka), 0.5× Complete EDTA-free protease inhibitors (Roche; contains a mixture of several protease inhibitors for the inhibition of serine and cysteine (but not metallo-) proteases; 1 tablet contains protease inhibitors sufficient for a 50 ml cell extract; the concentration used in this assay corresponds to 1 tablet in 100 ml).

Other Buffers:

1.) Stop solution: Dulbecco's PBS (PAA, Pasching, Austria), 25 mM EDTA (Sigma), 25 μM ATP (Roche), 0.05% Triton X-100 (Sigma);
2.) Saturation buffer: Dulbecco's PBS (PAA, Pasching, Austria), 100 μM ATP (Roche), 0.2% Triton X-100 (Sigma);
3.) Wash buffer: Dulbecco's PBS (PAA, Pasching, Austria).

Enzyme Solution:

ALK1 (Invitrogen, Paisley, United Kingdom) stock solution (35.7 ng/μl) is diluted to 4 ng/μl; final concentration in the reaction is 1 ng/μl.

Substrate Solution:

Dephosphorylated α-casein (Sigma) is biotinylated according to the manufacturer's protocol (Pierce, Bonn, Germany) resulting in a stock solution of 61.6 µM. Briefly, EZ-Link® Biotin reagent (sulfosuccinimidyl-6-(biotinamido) hexanoate; Pierce, Bonn, Germany) is added in equal molarity to α-casein and incubated on ice for 2 h. Afterwards, the biotin reagent is removed by dialysis (2×2 h and overnight).

A 100 mM solution of cold (unlabelled) ATP (Roche) is diluted 1:100 before each test. For the substrate mix, α-casein is diluted to 2.22 µM resulting in a final concentration of 1 µM α-casein in the reaction. Additionally, cold ATP is added to give a 1.11 µM solution which results in a final concentration of 500 nM in the reaction.

Radioactive ATP Solution:

The stock solution (9.25 MBq/25 µl of $^{33}$P-ATP; Perkin Elmer, Rodgau, Germany) is diluted to 651.2 Bq/µl. This corresponds to a final concentration of 162.8 Bq/µl.

Compound Solution:

Compounds are dissolved in 100% DMSO (10 mM stock solution) and diluted to 2 mM. Further dilutions are made stepwise 1:3.16 in DMSO.

Step-by-Step Protocol:

A volume of 9 µl substrate solution is provided into each well of a 384 well microliter plate (Greiner Bio-One, Solingen, Germany), 1 µl compound solution and 5 µl of the radioactive ATP solution are added. Enzyme reaction starts with addition of 5 µl of enzyme solution. The mixture is incubated for 60 minutes at room temperature and then stopped by addition of 10 µl stop solution. The 384 well microliter flashplates (Perkin Elmer, Rodgau, Germany) are saturated with 50 µl saturation buffer per well for at least 60 minutes. Subsequently, a volume of 20 µl is discarded and replaced with 20 µl of the stopped ALK1 reaction mixture. Binding of biotinylated substrate to the flashplate is allowed for by overnight incubation at room temperature. Bound substrate is separated from unbound components through repeated washing steps (3×50 µl washing buffer per well). Finally, 50 µl washing buffer is added, and the scintillation signal (cpm) is measured in a suitable counter (Perkin Elmer, Rodgau, Germany).

$IC_{50}$ values for individual compounds of the present invention are listed in Table 1 below:

TABLE 1

| Example No. | ALK1 IC$_{50}$ [nM] |
|---|---|
| 1 | 2.0 |
| 2 | 2.8 |
| 3 | 4.0 |
| 4 | 1.0 |
| 5 | 1.3 |
| 6 | 40 |
| 7 | 2.0 |
| 8 | 4.4 |
| 9 | 5.7 |
| 10 | 8.0 |
| 11 | 1.9 |
| 12 | 5.9 |
| 13 | 4.0 |
| 14 | 5.3 |
| 15 | 60 |
| 16 | 2.6 |
| 17 | 2.0 |
| 18 | 80 |
| 19 | 19 |
| 20 | 30 |
| 21 | 25 |
| 22 | 17 |
| 23 | 30 |

TABLE 1-continued

| Example No. | ALK1 IC$_{50}$ [nM] |
|---|---|
| 24 | 140 |
| 25 | 65 |
| 26 | 30 |
| 27 | 70 |
| 28 | 170 |
| 29 | 1.0 |
| 30 | 2.0 |
| 31 | 4.0 |
| 32 | 4.0 |
| 33 | 15 |
| 34 | 4.1 |
| 40 | 3.2 |
| 41 | 3.5 |
| 42 | 1.2 |
| 43 | 1.9 |
| 44 | 3.8 |

B-1b. ALK1 Kinase Assay (ProQinase Protocol)

ALK1 (Invitrogen, Carlsbad, Calif., USA) kinase activity was measured at ProQinase GmbH (Freiburg, Germany) in a radiometric assay using γ-$^{33}$P-ATP and casein (Sigma, St. Louis, Mo., USA) as substrate in 96-well PerkinElmer Flash-Plates™ (Boston, Mass., USA). The compounds were tested at 10 concentrations in the range of $1\times10^{-4}$ M to $3\times10^{-9}$ M in a total volume of 50 µl with a final DMSO concentration of 1% each. The assay components were mixed in the order:

20 µl assay buffer (70 mM HEPES-NaOH, pH 7.5, 3 mM MgCl$_2$, 3 mM MnCl$_2$, 2 µM sodium orthovanadate, 1.2 mM DTT);

5 µl γ-$^{33}$P-ATP (1.0 µM in water, approx. $6\times10^5$ cpm per well);

5 µl test compound solution (in 10% DMSO);

10 µl substrate (200 µg/ml, 1.0 µg/50 µl final concentration)/enzyme (4 µg/ml, 20 ng/50 µl=5.5 nM final concentration) solution (1:1 mixture).

The reaction mixtures were incubated at 30° C. for 60 minutes and stopped by adding 50 µl 2% (v/v) phosphoric acid. The plates were aspirated and washed twice with 200 µl 0.9% (w/v) sodium chloride. Incorporation of $^{33}$P$_i$ was determined with a microplate scintillation counter (Microbeta, Wallac). All assays were performed using a Becicman-Coulter/SAGIAN™ Core System.

Median values obtained from unspecific substrate binding of labelled. ATP were set as background level, while median values measured in the absence of any inhibitor were considered to reflect full activity of ALK1 kinase. The background activity (ba) was subtracted from the full activity (fa) value as well as from the values obtained from the test compound containing samples (test compound activity, tca). The residual activity in the latter was calculated as follows:

residual activity (%)=100×[(tca−ba)/(fa−ba)]

The residual activities for each concentration and the compound IC$_{50}$ values were calculated using Quattro Workflow V3.1.0 (Quattro Research GmbH, Munich, Germany). The fitting model for the IC$_{50}$ determinations was "Sigmoidal response (variable slope)" with parameters "top" fixed at 100% and "bottom" at 0%. The fitting method used was a least-squares fit.

Representative IC$_{50}$ values from this assay are listed in Table 2 below:

TABLE 2

| Example No. | ALK1 IC$_{50}$ [nM] |
|---|---|
| 7 | 6.7 |
| 11 | 3.0 |
| 28 | 124 |
| 35 | 6.9 |
| 36 | 21 |
| 37 | <3 |
| 38 | 4.0 |
| 39 | 5.7 |

B-2a. Smad7 Target Gene Induction: HMVEC Cell Assay and TaqMan Expression Analysis Activation of ALK1 receptors by BMP9 induces the Smad1/5 signalling pathway and enhances expression of target genes Smad6, Smad7 and Id-1. Induction of Smad7-mRNA in BMP9-stimulated endothelial cells was determined to monitor the cellular potency of ALK1 kinase inhibitors.

Human microvascular endothelial cells (HMVECadult, Cell Systems, St. Katharinen) were seeded in complete ENGS MV medium with all supplements (LifeLine Cell Technology) in 96 well plates with 10 000 cells per well. After 4 h incubation at 37° C. and 7.5% CO$_2$ in a humidified incubator, medium was replaced with minimal medium (ENGS MV without supplements containing 0.02% FCS). After 16 h, test compounds or medium (controls) were added to the cultures, followed 30 min later by addition of hBMP9 (R&D Systems). Medium was removed 1 to 4 h later, plates were gently washed with phosphate-buffered saline, and cells were lysed with 150 µl per well of ice-cold RLT buffer (Qiagen).

Total cellular RNA was isolated with the Trizol® reagent protocol according to the manufacturer's specifications (Invitrogen, USA) and treated with DNAseI to remove genomic DNA contamination.

For relative quantitation of the mRNA distribution of hSmad7, total RNA from each sample was first reverse-transcribed using the ImProm-II Reverse Transcription System (Promega, USA) according to the manufacturer's protocol. The final volume was adjusted to 200 µl with water.

For relative quantitation of selected mRNA, the Applied Bioscience ABI 7900HT Sequence Detection System was used according to the manufacturer's specifications and protocols. PCR reactions were set up to quantitate hSmad7- and the housekeeping gene L32-mRNA. Forward and reverse primers and probes for hSmad7 and L32 were designed using the Applied Bioscience ABI Primer Expressim software and were synthesized by Eurogentec (Belgium). The hSmad7 forward primer sequence was: Primer 1 (SEQ ID NO 1). The hSmad7 reverse primer sequence was: Primer 2 (SEQ ID NO 2). Probe 1 (SEQ ID NO 3), labelled with FAM as the reporter dye and TAMRA as the quencher, was used as a probe for hSmad7. The L32 forward primer sequence was: Primer 3 (SEQ ID NO 4). The L32 reverse primer sequence was: Primer 4 (SEQ ID NO 5). Probe 2 (SEQ ID NO 6), labelled with FAM as the reporter dye and TAMRA as the quencher, was used as a probe for L32.

| SEQ ID list: | | 5' to 3' |
|---|---|---|
| SEQ ID NO 1 | hSmad7 primer 1 (forward primer) | CCCTCCTTACTCCAGATACCC |
| SEQ ID NO 2 | hSmad7 primer 2 (reverse primer) | GGAGGAAGGCACAGCATCT |
| SEQ ID NO 3 | hSmad7 probe 1 | TTTTCTCAAACCAACTGCA GACTGTCC |
| SEQ ID NO 4 | L32 primer 3 (forward primer) | AAGTTCATCCGGCACCAGTC |
| SEQ ID NO 5 | L32 primer 4 (reverse primer) | TGGCCCTTGAATCTTCTACGA |
| SEQ ID NO 6 | L32 probe 2 | CCCAGAGGCATTGACAACAGGG |

The following reagents were prepared in a total of 20 µl added per well: 1× qPCR-MasterMix (Eurogentec, Belgium) and hSmad7 forward and reverse primers each at 200 nM, 200 nM hSmad7 FAM/TAMRA-labelled probe 1 (SEQ ID NO 3), and 5 µl of template cDNA. Correspondingly, a second mix in a total of 20 µl was prepared using L32 FAM/TAMRA-labelled probe 2 (SEQ ID NO 6) and L32 forward and reverse primers added per well in parallel samples.

Thermal cycling parameters were 2 min at 50° C., followed by 10 min at 95° C., followed by 40 cycles of melting at 95° C. for 15 sec and annealing/extending at 60° C. for 1 min.
Calculation of Relative Expression:

The Ct (cycle threshold) values were calculated from the turning point of PCR product quantity curves by the ΔΔCt method (delta-delta Ct):

$$\Delta Ct = Ct_{hSmad7} - Ct_{L32}; \text{ relative expression} = 2^{(15-\Delta Ct)}.$$

IC$_{50}$ values of test compounds were calculated on basis of relative Smad7 expressions at different compound concentrations. Representative values are listed in Table 3 below:

TABLE 3

| Example No. | hSmad7 IC$_{50}$ [nM] |
|---|---|
| 1 | 100 |
| 2 | 125 |
| 3 | 180 |
| 5 | 150 |
| 7 | 130 |
| 8 | 60 |
| 11 | 90 |
| 17 | 120 |
| 20 | 4400 |
| 21 | 6000 |
| 22 | 800 |

B-2b. Smad7 Target Gene Induction: HUVEC Cell Assay and TaqMan Expression Analysis The in vitro potency of ALK1 inhibitors was tested in a cell-based assay. Bone morphogenetic protein 9 (BMP9) induces Smad7 mRNA expression in human vascular endothelial cells (HUVEC) via activation of ALK1.

1.5×10$^4$ passage 2 HUVECs (Lonza, Basel, Switzerland) per well were seeded in a 96-well plate in EBM-2 medium containing EGM-2 additives and growth factors (Lonza, CC-3156 and CC-4176). After 4 h, the medium was changed to EBM-2 with 0.2% fetal calf serum (FCS) and the cells were starved for 20 h in a humidified incubator at 37° C., 5% CO$_2$. Test compounds were added at 11 different concentrations between 0 and 10 000 nM one hour prior to stimulation of the cells for 3 h with recombinant human BMP9 protein at 1 ng/ml (dissolved in 4 mM hydrochloric acid, 0.1% BSA at 10 µg/ml; R&D Systems, Minneapolis, Minn., USA, 3209BP). Medium was removed, and the cells were lysed in 100 µl RLT buffer (Qiagen, Hilden, Germany). RNA was isolated using the Qiagen RNeasy 96 Kit (order-No. 74182) according to manufacturer's instructions and eluted from the columns with 65 µl RNAse-free water. Reverse transcription for quantitative RT-PCR was carried out with the Omniscript Kit (Qiagen, 205113) in RNAse-free 96-well round-bottom plates. Per well, 6.8 µl of a reaction master mix containing 2 µl 10×RT-buffer, 2 µl dNTPs (5 mM each), 1.6 µl random primer N6 (125 µM), 0.25 µl Rnase Out (40 U/µl) and 1 µl Omniscript Reverse Transcriptase were added. After addition of 13.2 µl of the RNA/water mixture, plate contents were mixed, incubated for 1 h at 37° C. and the total volume adjusted to 100 µl in each well by addition of 80 µl RNAse-free water.

The quantification of human Smad7 mRNA was carried out on a TaqMan using the Eurogentec qPCR Mastermix Plus (RT-QP2X-03-075+; Cologne, Germany) and employing human L32 as housekeeping reference mRNA. Per qPCR reaction, 2.8 µl primer mix, 10 µl master mix, 2.2 µl water and 5 µl cDNA were added. Thermal cycling parameters were 2 min at 50° C., followed by 10 min at 95° C., followed by 40 cycles of melting at 95° C. for 15 sec and annealing/extending at 60° C. for 1 min.

Smad7 mRNA levels induced by 1 ng/ml BMP9 without the addition of any inhibitor were set at 100% induction, and % inhibition was calculated for each test compound with this value. For each test compound, every value was determined in quadruplicate. The $IC_{50}$ values were determined using Microsoft Excel. The fitting method used was a weighted, unconstrained ML-fit.

Representative $IC_{50}$ values from this assay are listed in Table 4 below:

TABLE 4

| Example No. | hSmad7 $IC_{50}$ [nM] |
|---|---|
| 1 | 94 |
| 2 | 160 |
| 3 | 120 |
| 5 | 290 |
| 7 | 140 |
| 11 | 180 |
| 17 | 290 |
| 20 | 5900 |
| 21 | 790 |
| 22 | 3100 |
| 30 | 51 |
| 37 | 330 |
| 39 | 500 |
| 40 | 62 |
| 41 | 77 |
| 42 | 6.6 |
| 43 | 27 |

B-3. Systemic Efficacy in the Laser-Induced Choroidal Neovascularization (CNV) Model The aim of this study was to determine whether once daily systemic administration (i.p.) of a test compound resulted in a decrease of vascular leakage and/or choroidal neovascularization in a rat model of laser-induced choroidal neovascularisation.

For this purpose, 16 pigmented Brown-Norway rats with no visible sign of ocular defects were selected and randomly divided into two groups of eight animals each. On day 0, the animals were anaesthetized by an intraperitoneal injection (15 mg/kg xylazine and 80 mg/kg ketamine). After instillation of one drop of 0.5% tropicamide to dilate the pupils, choroidal neovascularisation was induced by executing six 75 µm-sized choroidal burns around the optic disc of the right eyes using a 532 nm argon laser photocoagulation at 150 mW for 100 ms. The test compound and vehicle control (10% ethanol, 90% PEG 400) were administered once daily by intraperitoneal (i.p.) injections with dosing of the test compound at 50 mg/kg on days 0 and 1, and then continuing with 20 mg/kg from day 2 to day 23. The body weight of all animals was recorded before the start and once daily during the study.

An angiography was performed on day 21 using Heidelberg's Retinal Angiograph (HRA). After anaesthesia and pupillary dilation, 10% sodium fluorescein dye was injected subcutaneously, and images were recorded 10 min after dye injection. The vascular leakage of the fluorescein on the angiograms was evaluated by two examiners in a masked fashion and scored with 0 (no leakage) to 3 (strongly stained).

After euthanasia on day 23, the eyes were harvested and fixed in 4% paraformaldehyde solution for 1 hour at room temperature. After washing, the retina was carefully peeled, and the sclera-choroid was flat-mounted and incubated after blocking with a FITC-isolectine B4 antibody. The flat-mounted preparations were examined under a fluorescence microscope (Apotom) at 488 nm excitation wavelength. The volume of choroidal neovascularisation was scored by morphometric analysis of images using Axiovision 4.6 software.

For Example 11 as a representative of the compounds of the present invention, the following results were obtained in this model:

| | vascular leakage [angiography score] | choroidal neovascularisation lesion volume [$\mu m^3$ × 100 000] |
|---|---|---|
| Example 11 | 0.68 ± 0.35 | 3.48 ± 0.40 |
| vehicle control | 1.7 ± 0.32 | 5.83 ± 0.55 |

B-4. Topical Efficacy in the Laser-Induced Choroidal Neovascularization (CNV) Model The aim of this study was to determine whether twice daily topical administration (eye drops) of a test compound resulted in a decrease of vascular leakage and/or choroidal neovascularization in a rat model of laser-induced choroidal neovascularisation.

For this purpose, 65 pigmented Brown-Norway rats with no visible sign of ocular defects were selected and randomly assigned to six different groups (for n-numbers, see table below). On day 0, the animals were anaesthetized by an intraperitoneal injection (15 mg/kg xylazine and 80 mg/kg ketamine). After instillation of one drop of 0.5% tropicamide to dilate the pupils, choroidal neovascularisation was induced by burning six holes into the retina (disruption of Bruch's membrane) of one eye per animal using a 532 nm argon laser (lesion size: 50 µm; laser intensity: 150 mW; stimulus duration: 100 ms). Test compounds and vehicle controls were topically administered twice daily by instilling respective eye drops into the affected eye. The test compounds were dosed as follows: 10 µl of an eye drop formulation containing 20 mg/ml of the respective test compound suspended either in 100% liquid paraffin or in an aqueous vehicle (HPMC 15 cP 3.5%, polysorbate 80 0.5%, NaCl 0.9% in water) were applied to the affected eye twice daily at a 10 to 14 hour interval during the complete observation period of 23 days. Control animals received the respective vehicle (100% liquid paraffin or aqueous vehicle) topically twice daily. The body weight of all animals was recorded before the start and once daily during the study.

An angiography was performed on day 21 using a fluorescence fundus camera (Kowe). Here, after anaesthesia and pupillary dilation, 10% sodium fluorescein dye was injected subcutaneously, and images were recorded 2 and 10 min after dye injection. The vascular leakage of the fluorescein on the angiograms was evaluated by three different examiners who were blinded for group allocation (test compound versus vehicle), and scored with 0 (no leakage) to 3 (strongly stained).

On day 23, animals were sacrificed, and eyes were harvested and fixed in 4% paraformaldehyde solution for 1 hour at room temperature. After washing, the retina was carefully peeled, washed, blocked and stained with a FITC-isolectine B4 antibody in order to visualize the vasculature. Then, the sclera-choroids were flat-mounted and examined under a fluorescence microscope (Keyence Biozero) at 488 nm excitation wavelength. The area (in $\mu m^2$) of choroidal neovascularization was measured using ImageTool software.

For Examples 7 and 11 as representative compounds of the present invention, the following results were obtained in this model:

|  | vascular leakage [HRA score] | choroidal neovascularisation lesion size [$\mu m^2$ × 10 000] |
|---|---|---|
| Example 7 (aqueous vehicle; n = 9) | 1.49 ± 0.24 | 6.14 ± 1.60 |
| Example 7 (paraffin vehicle; n = 8) | 1.52 ± 0.21 | 6.21 ± 0.99 |
| Example 11 (aqueous vehicle; n = 7) | 1.66 ± 0.29 | 5.50 ± 1.38 |
| Example 11 (paraffin vehicle; n = 12) | 1.41 ± 0.29 | 6.45 ± 1.63 |
| aqueous vehicle control (n = 12) | 1.87 ± 0.27 | 7.84 ± 1.09 |
| paraffin vehicle control (n = 17) | 1.97 ± 0.19 | 7.00 ± 1.00 |

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. Examples Relating To Pharmaceutical Compositions

Pharmaceutical compositions according to the present invention can be illustrated as follows:

Sterile i.v. Solution:
A 5 mg/mL solution of the desired compound of the invention can be made using sterile, injectable water, and the pH is adjusted if necessary. The solution is diluted for administration to 1-2 mg/mL with sterile 5% dextrose and is administered as an i.v. infusion over about 60 minutes.

Lyophilized Powder for i.v. Administration:
A sterile preparation can be prepared with (i) 100-1000 mg of the desired compound of the invention as a lyophilized powder, (ii) 32-327 mg/mL sodium citrate, and (iii) 300-3000 mg Dextran 40. The formulation is reconstituted with sterile, injectable saline or 5% dextrose to a concentration of 10 to 20 mg/mL, which is further diluted with saline or 5% dextrose to 0.2 to 0.4 mg/mL, and is administered either as i.v. bolus or by i.v. infusion over 15-60 minutes.

Intramuscular Suspension:
The following solution or suspension can be prepared for intramuscular injection:
50 mg/mL of the desired, water-insoluble compound of the invention; 5 mg/mL sodium carboxymethylcellulose; 4 mg/mL Tween 80; 9 mg/mL sodium chloride; 9 mg/mL benzyl alcohol.

Hard Shell Capsules:
A large number of unit capsules are prepared by filling standard two-piece hard gelatin capsules each with 100 mg of the desired, powdered compound of the invention, 150 mg of lactose, 50 mg of cellulose and 6 mg of magnesium stearate.

Soft Gelatin Capsules:
A mixture of the desired compound of the invention in a digestible oil, such as soybean oil, cotton-seed oil or olive oil, is prepared and injected by means of a positive displacement pump into molten gelatin to form soft gelatin capsules containing 100 mg of the active ingredient. The capsules are washed and dried. The desired compound of the invention can be dissolved in a mixture of polyethylene glycol, glycerin and sorbitol to prepare a water-miscible medicine mix.

Tablets:
A large number of tablets are prepared by conventional procedures so that the dosage unit is 100 mg of the desired compound of the invention, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

Solution or Suspension for Topical Application to the Eye (Eye Drops):
A sterile formulation can be prepared with 100 mg of the desired compound of the invention as a lyophilized powder reconstituted in 5 mL of sterile saline. As preservative, benzalkonium chloride, thimerosal, phenylmercuric nitrate, or the like may be used in a range of about 0.001% to 1% by weight.

We claim:
1. A compound of formula (I)

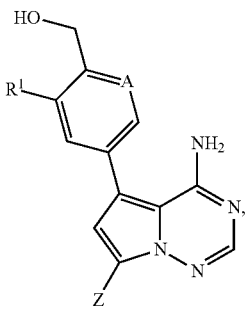

wherein
A is N or C—R², wherein
  R² represents hydrogen, fluoro or chloro,
R¹ represents hydrogen, fluoro, chloro, methyl, ethyl or methoxy,
and
Z represents $(C_1$-$C_4)$-alkyl or $(C_3$-$C_6)$-cycloalkyl each of which may be substituted with hydroxy,
or
Z represents a heterocyclic group of the formula

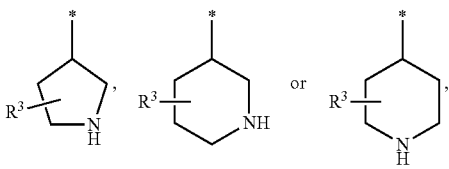

wherein * indicates the point of attachment to the pyrrolotriazine moiety,
and
R³ represents hydrogen or hydroxy,
  with the proviso that when R³ is hydroxy, this hydroxy is not attached to a ring carbon atom located adjacent to the ring nitrogen atom,
or
Z represents a thiazole group of the formula

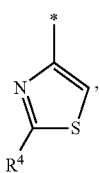

wherein * indicates the point of attachment to the pyrrolotriazine moiety,
and
R⁴ represents hydrogen, methyl, ethyl, amino or aminomethyl,
or
Z represents a group of the formula

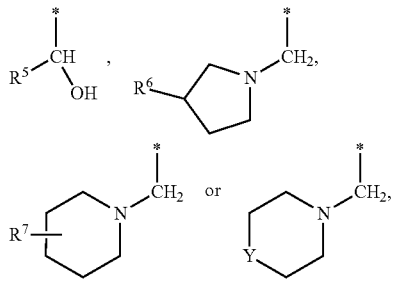

wherein * indicates the point of attachment to the pyrrolotriazine moiety,
R⁵ represents $(C_3$-$C_6)$-cycloalkyl, oxetanyl, tetrahydrofuranyl or tetrahydropyranyl,
R⁶ represents hydrogen or hydroxy,
R⁷ represents hydrogen or hydroxy,
  with the proviso that when R⁷ is hydroxy, this hydroxy is not attached to a ring carbon atom located adjacent to the ring nitrogen atom,
and
Y is O, NH or NCH₃,
or a pharmaceutically acceptable salt, hydrate and/or solvate thereof.

2. The compound of formula (I) according to claim 1, wherein
A is C—R², wherein
  R² represents hydrogen or fluoro,
R¹ represents hydrogen, fluoro, chloro, methyl, ethyl or methoxy,
and
Z represents n-propyl, n-butyl or cyclohexyl each of which may be substituted with hydroxy,
or
Z represents a heterocyclic group of the formula

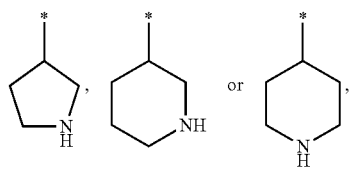

wherein * indicates the point of attachment to the pyrrolotriazine moiety,
or
Z represents a thiazole group of the formula

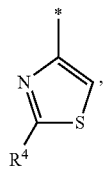

wherein * indicates the point of attachment to the pyrrolotriazine moiety, and

R⁴ represents methyl, ethyl, amino or aminomethyl, or

Z represents a group of the formula

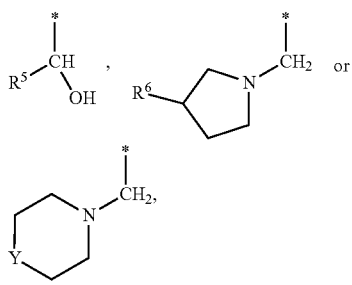

wherein * indicates the point of attachment to the pyrrolotriazine moiety,

R⁵ represents cyclopropyl or tetrahydropyran-4-yl,

R⁶ represents hydroxy, and

Y is O, or a pharmaceutically acceptable salt, hydrate and/or solvate thereof.

3. The compound of formula (I) according to claim 1, wherein

A is C—R², wherein

R² represents hydrogen or fluoro,

R¹ represents hydrogen, fluoro, methyl, ethyl or methoxy, and

Z represents 4-hydroxybutyl or 4-hydroxycyclohexyl, or

Z represents a heterocyclic group of the formula

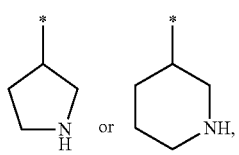

wherein * indicates the point of attachment to the pyrrolotriazine moiety, or

Z represents a thiazole group of the formula

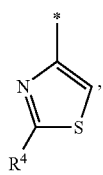

wherein * indicates the point of attachment to the pyrrolotriazine moiety, and

R⁴ represents methyl, ethyl, amino or aminomethyl, or

Z represents a group of the formula

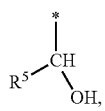

wherein * indicates the point of attachment to the pyrrolotriazine moiety, and

R⁵ represents cyclopropyl, or a pharmaceutically acceptable salt, hydrate and/or solvate thereof.

4. A process for preparing a compound of formula (I) as defined in claim 1, characterized in that a bromopyrrolotriazine of formula (II)

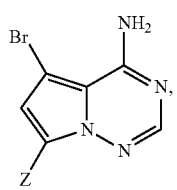

wherein Z has the meaning indicated in claim 1, is either

[A] coupled with an arylboronic acid or ester of formula (III)

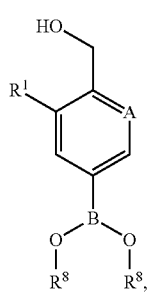

wherein A and R¹ have the meanings indicated in claim 1, and

R⁸ represents hydrogen or (C₁-C₄)-alkyl, or both R⁸ residues are linked together to form a —(CH₂)₂—, —C(CH₃)₂—C(CH₃)₂—, —(CH₂)₃— or —CH₂—C(CH₃)₂—CH₂— bridge, in the presence of a suitable palladium catalyst and a base to yield the target compound of formula (I)

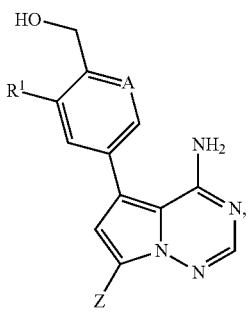

(I)

wherein A, Z and R¹ have the meanings indicated in claim 1, or

[B] first converted into the corresponding boronic acid or ester derivative of formula (IV)

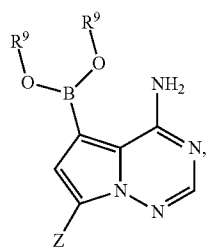

(IV)

wherein Z has the meaning indicated in claim 1, and

R⁹ represents hydrogen or (C₁-C₄)-alkyl, or both R⁹ residues are linked together to form a —(CH₂)₂—, —C(CH₃)₂—C(CH₃)₂—, —(CH₂)₃— or —CH₂—C(CH₃)₂—CH₂— bridge, which is then coupled with an aryl bromide of formula (V)

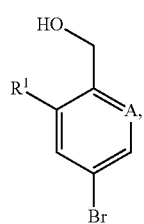

(V)

wherein A and R¹ have the meanings indicated in claim 1, in the presence of a suitable palladium catalyst and a base to also give the target compound of formula (I)

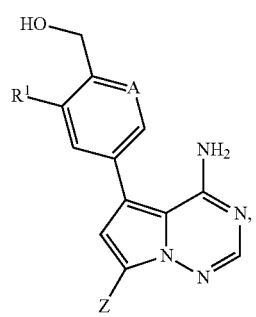

(I)

wherein A, Z and R¹ have the meanings indicated in claim 1, optionally followed, where appropriate, by (i) separating the compounds of formula (I) into their respective enantiomers and/or diastereomers, and/or (ii) converting the compounds of formula (I) into their respective hydrates, solvates, salts and/or hydrates or solvates of the salts by treatment with the corresponding solvents and/or acids.

5. A pharmaceutical composition comprising a compound as defined in claim 1, or a pharmaceutically acceptable salt, hydrate and/or solvate thereof, and one or more pharmaceutically acceptable excipients.

6. The pharmaceutical composition of claim 5 further comprising one or more additional therapeutic agents.

7. A method of treating age-related macular degeneration (AMD), choroidal neovascularisation (CNV), diabetic retinopathy and diabetic macula edema (DME) in a mammal, comprising administering to a mammal in need thereof a therapeutically effective amount of one or more compounds as defined in claim 1.

8. A method of treating age-related macular degeneration (AMD), choroidal neovascularisation (CNV), diabetic retinopathy and diabetic macula edema (DME) in a mammal, comprising administering to a mammal in need thereof a therapeutically effective amount of a pharmaceutical composition as defined in claim 5.

\* \* \* \* \*

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
ccctccttac tccagatacc c                    21

```
<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
ggaggaaggc acagcatct                                                  19

<210> SEQ ID NO 3
<211> LENGTH: 27
<212> TYPE: DNA
<213> ORGANISM: Artificial Sequence
<220> FEATURE:
<223> OTHER INFORMATION: Probe

<400> SEQUENCE: 3
ttttctcaaa ccaactgcag actgtcc                                         27

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aagttcatcc ggcaccagtc                                                 20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tggcccttga atcttctacg a                                               21

<210> SEQ ID NO 6
<211> LENGTH: 22
<212> TYPE: DNA
<213> ORGANISM: Artificial Sequence
<220> FEATURE:
<223> OTHER INFORMATION: Probe

<400> SEQUENCE: 6
cccagaggca ttgacaacag gg                                              22
```